(12) United States Patent
Stupp et al.

(10) Patent No.: US 8,062,219 B2
(45) Date of Patent: *Nov. 22, 2011

(54) APPARATUS FOR DETERMINING ASSOCIATION VARIABLES

(75) Inventors: Steven Elliot Stupp, San Carlos, CA (US); Lawrence Newman, Katonah, NY (US); Gert Lanckriet, San Diego, CA (US)

(73) Assignee: Trigeminal Solutions, San Carlos, CA (US)

( * ) Notice: Subject to any disclaimer, the term of this patent is extended or adjusted under 35 U.S.C. 154(b) by 1174 days.

This patent is subject to a terminal disclaimer.

(21) Appl. No.: 11/496,755

(22) Filed: Jul. 31, 2006

(65) Prior Publication Data

US 2006/0270918 A1 Nov. 30, 2006

Related U.S. Application Data

(63) Continuation-in-part of application No. 11/177,063, filed on Jul. 8, 2005, now Pat. No. 7,223,234, and a continuation-in-part of application No. 11/178,044, filed on Jul. 8, 2005, now Pat. No. 7,311,666.

(60) Provisional application No. 60/601,480, filed on Aug. 14, 2004, provisional application No. 60/591,300, filed on Jul. 27, 2004, provisional application No. 60/587,003, filed on Jul. 10, 2004.

(51) Int. Cl.
*A61B 5/00* (2006.01)

(52) U.S. Cl. ........ 600/300; 600/301; 600/534; 600/544; 600/545; 340/539.12; 705/2

(58) Field of Classification Search .................. None
See application file for complete search history.

(56) References Cited

U.S. PATENT DOCUMENTS

| 5,307,263 A | 4/1994 | Brown ........................ 600/301 |
| 5,331,549 A | 7/1994 | Crawford .................... 600/513 |
| 5,357,427 A | 10/1994 | Langen et al. ............... 600/300 |

(Continued)

FOREIGN PATENT DOCUMENTS

WO  WO 03/063684  8/2003

(Continued)

OTHER PUBLICATIONS

Supplemental European Search Report for European Patent Application 05769217.0 (dated Apr. 17, 2009).

(Continued)

*Primary Examiner* — Sam Yao
*Assistant Examiner* — Bobby Soriano

(57) ABSTRACT

An apparatus, and related method, for determining one or more association variables is described. The apparatus includes at least one processor, at least one memory, and at least one program module stored in the memory configured to be executed by the processor. The program module includes instructions for selecting a subset of temporal onsets in a set of temporal onsets, instructions for determining a statistical relationship between the subset of temporal onsets and a pattern of occurrence of a variable, and instructions for identifying the variable as a migraine variable in accordance with the statistical relationship. The subset of temporal onsets includes one or more onsets corresponding to one or more migraines experienced by at least one individual, and the set of temporal onsets includes the subset of temporal onsets and one or more temporal onsets corresponding to one or more additional headaches experienced by at least the one individual.

20 Claims, 23 Drawing Sheets

U.S. PATENT DOCUMENTS

| | | | |
|---|---|---|---|
| 5,434,611 A | 7/1995 | Tamura | 725/116 |
| 5,437,278 A | 8/1995 | Wilk | 600/425 |
| 5,441,047 A | 8/1995 | David et al. | 600/483 |
| 5,772,586 A | 6/1998 | Heinonen | 600/300 |
| 5,897,493 A | 4/1999 | Brown | 600/300 |
| 5,911,132 A | 6/1999 | Sloane | 705/3 |
| 5,950,632 A | 9/1999 | Reber et al. | 128/898 |
| 5,960,403 A | 9/1999 | Brown | 705/2 |
| 5,995,077 A | 11/1999 | Wilcox et al. | 715/841 |
| 5,997,476 A | 12/1999 | Brown | 600/300 |
| 6,101,478 A | 8/2000 | Brown | 705/2 |
| 6,122,351 A | 9/2000 | Schlueter, Jr. et al. | 379/106.02 |
| 6,139,494 A | 10/2000 | Cairnes | 600/300 |
| 6,151,586 A | 11/2000 | Brown | 705/14 |
| 6,168,563 B1 | 1/2001 | Brown | 600/301 |
| 6,234,964 B1 | 5/2001 | Iliff | 600/300 |
| 6,270,455 B1 | 8/2001 | Brown | 600/300 |
| 6,278,999 B1 | 8/2001 | Knapp | 707/9 |
| 6,290,646 B1 | 9/2001 | Cosentino et al. | 600/300 |
| 6,317,700 B1 | 11/2001 | Bagne | 702/181 |
| 6,334,778 B1 | 1/2002 | Brown | 434/258 |
| 6,364,834 B1 | 4/2002 | Reuss et al. | 600/300 |
| 6,368,273 B1 | 4/2002 | Brown | 600/300 |
| 6,381,577 B1 | 4/2002 | Brown | 705/2 |
| 6,409,662 B1 | 6/2002 | Lloyd et al. | 600/300 |
| 6,440,068 B1 | 8/2002 | Brown et al. | 600/300 |
| 6,450,955 B1 | 9/2002 | Brown et al. | 600/300 |
| 6,454,705 B1 | 9/2002 | Cosentino et al. | 600/300 |
| 6,458,080 B1 | 10/2002 | Brown et al. | 600/300 |
| 6,527,712 B1 | 3/2003 | Brown et al. | 600/300 |
| 6,569,094 B2 | 5/2003 | Suzuki et al. | 600/300 |
| 6,602,191 B2 | 8/2003 | Quy | 600/300 |
| 6,616,613 B1 | 9/2003 | Goodman | 600/504 |
| 6,641,532 B2 | 11/2003 | Iliff | 600/300 |
| 6,669,631 B2 | 12/2003 | Norris | 600/300 |
| 6,712,763 B2 | 3/2004 | Abraham-Fuchs et al. | 600/300 |
| 6,755,783 B2 | 6/2004 | Cosentino et al. | 600/300 |
| 6,825,332 B1 | 11/2004 | Frants et al. | 536/23.5 |
| 7,223,234 B2 | 5/2007 | Stupp | 600/300 |
| 7,311,666 B2 | 12/2007 | Stupp | 600/300 |
| 7,613,619 B1 | 11/2009 | Harter et al. | 705/2 |
| 7,676,384 B2 | 3/2010 | Baker et al. | 705/3 |
| 2001/0056229 A1 | 12/2001 | Cosentino et al. | 600/300 |
| 2002/0035486 A1 | 3/2002 | Huyn et al. | 705/3 |
| 2002/0128866 A1* | 9/2002 | Goetzke et al. | 705/2 |
| 2002/0173991 A1 | 11/2002 | Avitall | 705/2 |
| 2003/0009088 A1 | 1/2003 | Korth et al. | 600/300 |
| 2003/0144829 A1* | 7/2003 | Geatz et al. | 703/22 |
| 2003/0212313 A1 | 11/2003 | Harrison | 600/300 |
| 2004/0102685 A1 | 5/2004 | Cosentino et al. | 600/300 |
| 2004/0122706 A1 | 6/2004 | Walker et al. | 705/2 |
| 2004/0130450 A1 | 7/2004 | Kleinschmidt | 340/573.1 |
| 2004/0186746 A1 | 9/2004 | Angst et al. | 705/3 |
| 2004/0210458 A1 | 10/2004 | Evans et al. | 705/2 |
| 2004/0210459 A1 | 10/2004 | Kirchhoff et al. | 705/2 |
| 2005/0236004 A1 | 10/2005 | Magnuson et al. | 128/898 |
| 2006/0104995 A1 | 5/2006 | Turkel et al. | 424/239.1 |
| 2006/0257946 A1* | 11/2006 | Ding et al. | 435/7.9 |
| 2007/0179354 A1 | 8/2007 | Stupp | 600/300 |
| 2007/0179363 A1 | 8/2007 | Stupp | 600/300 |
| 2007/0219433 A1 | 9/2007 | Stupp | 600/300 |
| 2008/0108881 A1 | 5/2008 | Stupp | 600/300 |

FOREIGN PATENT DOCUMENTS

WO  WO 2004/027676 A2  4/2004

OTHER PUBLICATIONS

Office Action for U.S. Appl. No. 11/704,735 (dated May, 29, 2009).
Reply to Supplemental European Search Report (dated Jul. 13, 2009).
Reply to Office Action for U.S. Appl. No. 11/704,735, (dated Aug. 28, 2009).
Stephan Dreiseitl and Lucila Ohno-Machado, Logistics Regression and Artificial Neural Network Classification Models: A Methodology Review, J. of Biomedical Informatics, vol. 35, pp. 352-359 (2002).
PCT Search Report and Written Opinion for PCT Application PCT/US05/24205, dated Jan. 5, 2007.
Notice of Allowability (including Reasons for Allowance) for U.S. Appl. No. 11/177,063 (now U.S. Patent 7,223,234), dated Aug. 28, 2006.
Comment on Statement of Reasons for Allowance for U.S. Appl. No. 11/177,063 (now U.S. Patent 7,223,234), dated Sep. 27, 2006.
Michele Sharp, "The Migraine Cookbook" (Marlow & Company, New York, 2001) pp. v-xi and 1-25, 29, and 53.
Katharina Dalton, "Food Intake Prior to Migraine Attacks-Study of 2,313 Spontaneous Attacks," Headache 15, pp. 188-193 (1975).
J. B. Brainard, "Salt Load as a Trigger for Migraine," Minn. Med. 59(4), pp. 232-233 (1976).
G. Nappi et al., "Headache Temporal Patterns: Towards a Chronobiological Model," Cephalalgia 3 suppl. 1, pp. 21-30 (1983).
R. C. Peatfield et al., "The Prevalence of Diet-Induced Migraine," Cephalalgia 4, pp. 179-183 (1984).
J. Blau, "Pathogenesis of Migraine Attack: Initiation," J R Coll Physicians Lond 19, pp. 166-168 (1985).
S. Diamond et al., "Diet and Headache: Is There a Link?" Postgrad. Med. 79(14), pp. 279-286 (1986).
Vic van den Bergh et al., "Trigger Factors in Migraine: A Study Conducted by the Belgian Migraine Society," Headache 27(4), pp. 191-196 (1987).
J. N. Blau et al., "Preventing Migraine: A Study of Precipitating Factors," Headache 28, pp. 481-483 (1988).
R. B. Lipton et al., "Aspartame as a Dietary Trigger of Headache," Headache 29(2), pp. 90-92 (1989).
V. Glover et al., "The biochemical basis of migraine predisposition," in "Migraine: A Spectrum of Ideas," Sandler, M. and Collins, G.M., eds. (Oxford University Press. Oxford, 1990), pp. 228-241.
T. Köhler et al., "Daily Stress as a Trigger of Migraine Attacks: Results of Thirteen Single-Subject Studies," J. Consult. Clin. Psychol. 58(6), pp. 870-872 (1990).
G. de Matteis et al., "Geomagnetic Activity, Humidity, Temperature and Headache: Is There Any Correlation?" Headache 34(1), pp. 41-43 (1994).
B. G. Buchanan et al., "An Intelligent Interactive System for Delivering Individualized Information to Patients," Artificial Intelligence in Medicine 7, pp. 117-154 (1995).
M. Sandler et al., "Diet Migraine: Recent Progress in the Red (and White) Wine Story," Cephalalgia 15(2), pp. 101-103 (1995).
L. C. Turner et al., "Migraine Trigger Factors in Non-Clinical Mexican-American Population in San Deigo County: Implications for Etiology," Cephalalgia 15(6), pp. 523-530 (1995).
R. Leira et al., "Diet and Migraine," Rev. Neurol. 24(129), pp. 534-538 (1996).
D. A. Marcus et al., "A Double-Blind Provocative Study of Chocolate as a Trigger of Headache," Cephalalgia 17(8), pp. 855-862 (1997).
E. M. William et al., "Guidelines for the Nonpharmacologic Management of Migraine in Clinical Practice," Canadian Medical Association Journal 159(1), pp. 47-54 (1998).
"Two by Two Tables," Simple Interactive Statistical Analysis, http://home.clara.net/sisa/two2h1p.htm, Feb. 18, 1999.
"Correlation," Creative Research Systems, http://www.surveysystem.com/correlation.htm, Feb. 21, 1999.
H. Chabriat et al., "Precipitating Factors of Headache: A Prospective Study in a National Control-Matched Survey in Migraineurs and Nonmigraineurs," Headache 39(5), pp. 335-338 (1999).
"Diet," http://www.painforum.com/en/1/hcpmigprediet.html, Nov. 11, 1999.
L. J. Cooke et al., "Chinook Winds and Migraine Headaches," Neurology 54(2), pp. 302-307 (2000).
"Fisher Exact," Simple Interactive Statistical Analysis, http://home.clara.net/sisa/fishrhlp.htm, Mar. 9, 2000.
Headache Diary, http://www.pancare.net/html/head-ache_diary.asp, PainCare, Inc., Aug. 24, 2000.
"7.3.3. How Can We Determine Whether Two Processes Produce the Same Proportion of Defectives?" NIST Engineering Statistics Handbook, http://www.itl.nist.gov/div898/handbook/prc/section3/prc33.htm, Oct. 4, 2000.

S. D. Silberstein et al., "Migraine: Diagnosis and Treatment," "Wolff's Headache and Other Head Pain," Seventh Edition, Silberstein, S.D., Lipton, R.B., and Dalessio, D.J., eds. (Oxford University Press, New York, 2001), pp. 135-140 and 210-237.

V. T. Martin et al., "Toward a Rational Understanding of Migraine Trigger Factors," Med Clin North Am. 85(4), pp. 911-941 (2001).

"Migraine," Merck Medicus Modules, http://www.merckmedicus.com/pp/hcp/diseasemodules/migraine/default.jsp, Jul. 16, 2001.

R. A. Davidoff, "Initiators, Precipitators, and Triggers," in "Migraine: Manifestations, Pathogenesis and Management," Chapter 5 (Oxford, University Press, 2002).

P. J. Goadsby et al., "Migraine—Current Understanding and Treatment," N. Engl. J. Med. 346(4), pp. 257-268 (2002).

Dang Quang A et al., "Correlation Analysis," http://www.netnam.vn/unescocourse/statistics/11_6.htm, Mar. 26, 2002.

John Wasson, "Ed 602 —Lesson 14 —Chi-Square," http://www.mnstate.edu/wasson/ed601esson14.htm, Jun. 26, 2002.

John Wasson, "Ed 602—Lesson 15—Testing the Significance of Correlation Coefficients, Choosing the Proper Statistical Test," http://www.mnstate.edu/wasson/ed620lesson15.htm, Jun. 26, 2002.

R. Lerusalimschy et al., "Precipitating Factors of Migraine Attacks in Patients With Migraine Without Aura," Arq Neutropsiquiatr. 60(3-A), pp. 609-613 (2002).

J. G. Millichap et al., "The Role of Diet in Migraine Headaches," http://www.nutrition4health.org/NOHAnews/NNS02DietMigraineHeadaches.htm, Oct 29, 2002.

J. Connor-Linton, "Chi Square Tutorial," http://www.georgetown.edu/faculty/ballc/webtools/web_chi_tut.html, Dec. 22, 2002.

J. G. Millichap et al., "The Diet Factor in Pediatric and Adolescent Migraine," Pediatric Neurology 28 (1), pp. 9-15 (2003).

S. Borgatti, "Distance and Correlation," Analytic Technologies, http://www.analytictech.com/mb813/handouts/distance_and_correlation.htm, Jan. 24, 2003.

"MedSearch Technologies, Inc. Develops a Revolutionary Home-Care Wireless Technology Utilizing PDAs—Personal Organizers—as Patient Monitors," MedSearch Technologies, http://www.mobic.com/oldnews/2000/09/medsearch_technologies.htm, May 18, 2003.

R. Zivadinov et al., "Migraine and Tension-Type Headaches in Croatia: A Population-Based Survey of Precipitation Factors," Cephalalgia 23(5), pp. 336-343 (2003).

"Managing Migraine: Translating Research into Clinical Practice," Medscape, http://www.medscape.com/viewprogram/2644_pnt, Sep. 26, 2003.

PDA Migraine Manager, TIS Software, http://www.tissoftware.net/products.htm, Dec. 14, 2003.

iMetrikus, Products and Markets, http://www.imetrikus.com/products.asp, iMetrikus, Feb. 28, 2004.

"The International Classification of Headache Disorders," $2^{nd}$ Edition, Cephalalgia 24 suppl. 1, pp. 9-160 (2004).

K. E. Gordon et al., "Self-Reported Headache Frequency and Features Associated with Frequent Headaches in Canadian Young Adolescents," Headache 44, pp. 555-561 (2004).

P. B. Prince et al., "The Effect of Weather on Headache," Headache 44, pp. 596-602 (2004).

J. Ressner, "Push-Button Medicine," Time Magazine, Aug. 9, 2004, p. 101.

R. Baraniuk, "Angle Between Vectors: Inner Products," http://cnx.rice.edu/content/m12101/latest/, Oct. 24, 2004.

C. Hermann et al., "Use of Hand-Held Computers for Symptom-Monitoring: The Case of Chronic Headache," Min/Body Medicine 1(2), pp. 59-69 (1995).

P.C. Honkoop et al., "High-Density Assessment of the IHS Classification Criteria for Migraine Without Aura: A Prospective Study," Cephalalgia 19, pp. 201-206 (1999).

K.A. Holroyd et al., "A Hand-Held Computer Diary," presented at the American Headache Society Convention, Montreal, Canada (2000). The "Palm Diary Manual" that this presentation was based on is enclosed.

V. Yaremchuk, "Artificial Neural Networks and the Treatment of Migraine," M.S. thesis, Apr. 30, 2002, http://www.cs.alberta.ca/~jonathan/Grad/vanessa.msc.ps.

L.A. Lenert et al., "Potential Validity of Conducting Research on Headache in Internet Populations," Headache 42, pp. 200-203 (2002).

K.A. Holroyd, "Assessment and Psychological Management of Recurrent Headache Disorders," J. Consulting and Clinical Psychology 70(3), pp. 656-677 (2002).

R.A. Nicholson et al., "Moderators and Mediators of Behavior in Treatment for Headache," Headache 45, pp. 513-519 (2005).

Office Action for U.S. Appl. No. 11/704,735 (dated Oct. 28, 2009).

Reply to Office Action for U.S. Appl. No. 11/704,735 (dated Nov. 24, 2009).

Office Action for U.S. Appl. No. 11/604,494 (dated Jan. 8, 2010).

Reply to Office Action for U.S. Appl. No. 11/604,494 (dated Apr. 7, 2010).

Office Action for U.S. Appl. No. 11/704,735 (dated Apr. 13, 2010).

Reply to Office Action for U.S. Appl. No. 11/704,735 (dated Jul. 9, 2010).

Office Action for U.S. Appl. No. 11/809,807 (dated Mar. 30, 2010).

Reply to Office Action for U.S. Appl. No. 11/809,807 (dated Jul. 9, 2010).

C.M. Bishop, "Neural Networks for Pattern Recognition," Oxford University Press, pp. 1-23, 1995.

G.E. Hinton et al., "Reducing the Dimensionality of Data with Neural Networks," Science, vol. 313, No. 5786, pp. 504-507, 2006.

P.B. Prince et al., "The Effect of Weather on Headache," Headache vol. 44, pp. 596-602, 2004.

M. Connelly et al., "Electronic Momentary Assessment of Weather Changes as a Trigger of Headaches in Childtren," Headache vol. 50, pp. 779-789, 2010.

* cited by examiner

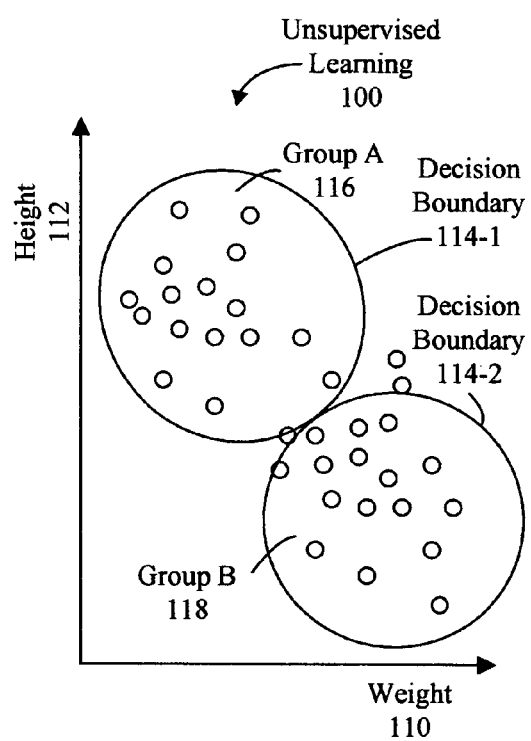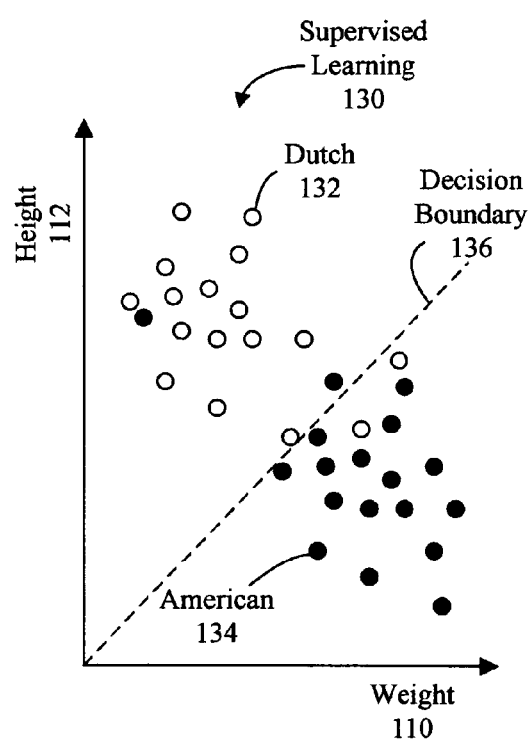
Figure 1A
(Prior Art)
Figure 1B
(Prior Art)

APPARATUS FOR DETERMINING ASSOCIATION VARIABLES

CROSS REFERENCE TO RELATED APPLICATIONS

This application claims priority under 35 U.S.C. 120 as a Continuation-in-Part Patent Application of U.S. Patent application Ser. No. 11/177,063, "Apparatus for Determining Association Variables," filed on Jul. 8, 2005 (now U.S. Pat. No. 7,223,234), and as a Continuation-in-Part Patent Application of U.S. patent application Ser. No. 11/178,044, "Apparatus for Collecting Information," filed on Jul. 8, 2005 (now U.S. Pat. No. 7,311,666), both of which claim priority under 35 U.S.C. 119(e) to U.S. Provisional Application Ser. No. 60/601,480, "Medical Informatics System," filed on Aug. 14, 2004, to U.S. Provisional Application Ser. No. 60/591,300, entitled "Healthcare Provider-Patient Interaction Management System," filed on Jul. 27, 2004, and to U.S. Provisional Application Ser. No. 60/587,003, entitled "Medical Informatics System," filed on Jul. 10, 2004, the contents of each of which are herein incorporated by reference.

This application is also related to U.S. patent application Ser. No. 11/529,054, "Apparatus for Determining Association Variables," filed on Sep. 27, 2006, to U.S. patent application Ser. No. 11/604,494, "Apparatus for Determining Association Variables," filed on Nov. 27, 2006, to U.S. patent application Ser. No. 11/704,735, "Apparatus for Providing Information Based on Association Variables," filed on Feb. 9, 2007, and to U.S. patent application Ser. No. 11/809,807, "Apparatus for Aggregating Individuals Based on Association Variables," filed on May 31, 2007.

FIELD OF THE INVENTION

The present invention relates generally to an apparatus, and related methods, for processing data, and more specifically, for determining statistical relationships.

BACKGROUND OF THE INVENTION

Statistical learning problems may be categorized as supervised or unsupervised. In supervised learning, the goal is to predict an output based on a number of input factors or variables (henceforth, referred to as variables), where a prediction rule is learned from a set of examples (referred to as training examples) each showing the output for a respective combination of variables. In unsupervised learning, the goal is to describe associations and patterns among a set of variables without the guidance of a specific output. An output may be predicted after the associations and patterns have been determined. These categories are illustrated in FIGS. 1A and 1B, which show data points as a function of weight 110 and height 112. In unsupervised learning 100 in FIG. 1A, the data may be described by input variables weight 110 and height 112 without any additional information (e.g., labels) that could help to find patterns in the data. Patterns in the data may be found by learning that there are two distinguished "clusters" of data points (represented by circles or decision boundaries 114 around them). Within each cluster, data in group A 116 or group B 118 are highly similar (i.e., close) and between clusters data are highly dissimilar (i.e., further away). When a new data point, i.e., combination of the input variables becomes available, it may be categorized as similar to and thus a potential member of one of the clusters that have been discovered, or as an outlier or as a member of a new cluster.

In supervised learning 130 in FIG. 1B, additional information about the data is available. The data points are labeled as Dutch 132 (white circles) or American 134 (filled-black circles). This extra information is exactly the output one wants to predict for future data. Having it available for the training data or examples allows predictive decision boundary 136 to be determined. In general, statistical learning involves finding a statistical model that explains the observed data that may be used to analyze new data, e.g., learning a weighted combination of numerical variables from labeled training data to predict a class or classification for a new combination of variables. Determining a model to predict quantitative outputs (continuous variables) is often referred to as regression. Determining a model to predict qualitative data (discrete categories, such as 'yes' or 'no') is often referred to as classification.

Developing models for statistical learning problems involving longitudinal data, in which a time series of observations are collected over a period of time, poses several challenges, including those associated with collecting the data efficiently and accurately. Analysis of the data may also be problematic, in particular, for a class of problems where variables associated with time-varying phenomena that have discrete events or epochs, each epoch having a characteristic onset time (henceforth referred to as a temporal onset), are sought. For example, in such problems there may be limited data and a plurality of potential variables to be screened. The analysis, therefore, may be underdetermined. In addition, the potential variables may not be independent from one another and/or samples of the potential variables may not have a corresponding probability distribution (for example, a normal distribution).

There is a need, therefore, for an analysis technique to address the challenges described above and to determine variables associated with time-varying phenomena having discrete epochs.

SUMMARY OF THE INVENTION

An apparatus, and related method, for determining one or more association variables is described. The apparatus may include at least one processor, at least one memory, and at least one program module. The program module may be stored in the memory and may be configured or configurable to be executed by the processor. The program module may include instructions for selecting a subset of temporal onsets in a set of temporal onsets; instructions for determining a statistical relationship between the subset of temporal onsets and a pattern of occurrence of a variable; and instructions for identifying the variable as a migraine variable in accordance with the statistical relationship. The subset of temporal onsets may include one or more onsets corresponding to one or more migraines experienced by at least one individual, and the set of temporal onsets may include the subset of temporal onsets and one or more temporal onsets corresponding to one or more additional headaches experienced by at least the one individual. The determining may include contributions from presence and absence information in the pattern of occurrence of the variable.

The one or more additional headaches may include one or more rebound migraines, one or more recurrence migraines and/or one or more tension headaches.

The pattern of occurrence of the variable may be during a set of time intervals. A respective time interval in the set of time intervals may precede a corresponding respective temporal onset in the subset of temporal onsets. Time intervals in the set of time intervals may be offset in time from temporal onsets in the subset of temporal onsets.

In some embodiments, the program module further includes instructions for excluding at least one of the temporal onsets in the set of temporal onsets from the subset of temporal onsets due to missing data in the pattern of occurrence of the variable.

In some embodiments, the pattern of occurrence of the variable includes categorical data. In some embodiments, a respective entry in a pattern of occurrence of the variable is considered present if the respective entry approximately exceeds a threshold.

In some embodiments, the pattern of occurrence of the variable includes one or more entries corresponding to at least a time interval after at least a respective temporal onset in the subset of temporal onsets. A respective migraine corresponding to at least the respective temporal onset may have a duration including at least the time interval. The one or more entries may be excluded when the statistical relationship is determined.

The determining may use a non-parametric statistical analysis technique, including a chi-square analysis technique, a log-likelihood ratio analysis technique and/or a Fisher's exact probability analysis technique. The determining may use a supervised learning technique including a support vector machines (SVM) analysis technique and a classification and regression tree (CART) analysis technique. The statistical relationship may at least in part be determined using a filter, such as an analog filter and/or a digital filter.

In some embodiments, the program module further includes instructions for receiving information including the set of temporal onsets and the pattern of occurrence of the variable. In some embodiments, the program module further includes instructions for providing recommendations to one or more individuals in accordance with the migraine variable.

In some embodiments, the program module further includes instructions for determining statistical relationships for a plurality of variables. In some embodiments, the program module further includes instructions for determining a first ranking of the plurality of variables in accordance with the statistical relationships and/or for subtracting a second ranking from the first ranking. This second ranking may correspond to a background, such as noise or interference signals.

The migraine variable may be a migraine trigger that at least in part induces a migraine in at least the one individual if at least the one individual is exposed to the migraine trigger. In some embodiments, the program module further includes instructions for associating at least the one individual with one or more groups of migraine triggers in accordance with the identified migraine trigger.

In another embodiment, the method may be implemented as a computer-program product for use in conjunction with a computer system. The computer-program product may include a computer-readable storage medium and a computer-program mechanism embedded therein for determining one or more migraine variables associated with migraines.

In another embodiment, a process for determining one or more migraine variables associated with migraines is described. A first data stream including a set of temporal onsets corresponding to one or more migraines and a pattern of occurrence of a variable are transmitted. A second data stream including information that identifies the variable as a migraine variable is received. The information may be determined in accordance with a statistical relationship between a subset of temporal onsets in the set of temporal onsets and a pattern of occurrence of the variable. The subset of temporal onsets may include one or more onsets corresponding to one or more migraines experienced by at least one individual. The set of temporal onsets may include the subset of temporal onsets and one or more temporal onsets corresponding to one or more additional headaches experienced by at least the one individual. The statistical relationship may include contributions from presence and absence information in the pattern of occurrence of the variable.

In another embodiment, a graphical user interface and related method are described. The graphical user interface includes a first window to receive and display information corresponding to a first item consumed by an individual during a first time interval, and a second window to display selectable second items consumed by the individual during a second time interval. At least a portion of the second time interval precedes the first time interval.

In another embodiment, an apparatus, and related method, for determining items that include a variable is described. The apparatus may include at least one processor, at least one memory, and at least one program module. The program module may be stored in the memory and may be configured or configurable to be executed by the processor. The program module may include instructions for determining first instances of the variable in a data structure, and instructions for identifying one or more items that include at least one of these first instances of the variable. In some embodiments, the program module may further include instructions for defining the one or more identified items as subsequent versions or the variable and for repeating the operations of identifying and determining until a number of iterations are performed, a probability associated with items identified in a given iteration is less than a pre-determined value, or no instances of items are identified in a given iteration.

The variable may be an ingredient and the one or more identified items in the operations of identifying and determining may be foods that contain the ingredient.

In another embodiment, a method for providing food products is described. In the method, a first set of food products that contains a first amount of at least some migraine triggers in a first set of migraine triggers is provided, and a second set of food products that contains a second amount of at least some migraine triggers in a second set of migraine triggers is provided. The first amount is less than a first pre-determined value and the second amount is less than a second pre-determined value. The first set of food products may be intended for consumption by members of a first group of individuals that respond to the first set of migraine triggers and the second set of food products may be intended for consumption by members of a second group of individuals that respond to the second set of migraine triggers. Response to a migraine trigger in a respective set of migraine triggers may include at least one individual having a migraine if at least the one individual is exposed to a respective amount of the migraine trigger greater than a respective pre-determined value.

The respective food product may include beverages. In some embodiments, the respective set of food products may contain a third amount of one or more items associated with one or more of the migraine triggers in the respective set of migraine triggers. The third amount may be less than a third pre-determined value. The one or more items may include foods in a food group corresponding to one or more of the migraine triggers in the respective set of migraine triggers. In some embodiments, at least one of the sets of food products includes a fourth amount of one or more compounds that chemically react with one or more of the migraine triggers in the corresponding set of migraine triggers thereby reducing an efficacy of the one or more migraine triggers to induce a migraine in at least the one individual. The fourth amount may be greater than a fourth pre-determined value.

In another embodiment, a data structure includes a first variable and a corresponding first set of time intervals, and a second variable and a corresponding second set of time intervals. The first variable and the second variable may be associated with a medical condition in at least the one individual. A severity of at least one symptom associated with the medical condition may be increased if at least the one individual is exposed to the first variable during at least one time interval in the first set of time intervals and the second variable during at least one time interval in the second set of time intervals. In some embodiments, the first variable and the second variable are migraine triggers. In some embodiments, the first variable and the second variable further include corresponding threshold quantities, in which quantities greater than the threshold quantities induce a migraine in at least the one individual.

In another embodiment, an apparatus, and related method, is described. The apparatus may include at least one processor, at least one memory, and at least one program module. The program module may be stored in the memory and may be configured or configurable to be executed by the processor. The program module may include instructions for associating one or more migraine triggers, which have been determined for an individual, with a set of pre-determined migraine triggers that are associated with a group of individuals. The one or more migraine triggers that have been determined for the individual may at least in part induce a migraine in at least the individual if at least the individual is exposed to the one or more migraine triggers. In some embodiments, the one or more migraine triggers are determined in accordance with presence and/or absence of one or more markers in a set of markers in a biological sample from the individual.

In another embodiment, an apparatus, and related method, is described. The apparatus may include at least one processor, at least one memory, and at least one program module. The program module may be stored in the memory and may be configured or configurable to be executed by the processor. The program module may include instructions for recommending one or more medicines to an individual in accordance with one or more migraine triggers that have been determined for the individual. The one or more migraine triggers may at least in part induce a migraine in at least the individual if at least the individual is exposed to the one or more determined migraine triggers. The one or more medicines may include an acute medicine that is taken during a migraine and/or a preventive medicine that is taken during migraine attacks and between migraine attacks. In some embodiments, the one or more migraine triggers are determined in accordance with presence and/or absence of one or more markers in a set of markers in a biological sample from the individual.

The disclosed embodiments reduce or eliminate the problems described above and provide an analysis technique for determining association variables associated with time-varying phenomena having discrete epochs.

BRIEF DESCRIPTION OF THE DRAWINGS

Additional objects and features of the invention will be more readily apparent from the following detailed description and appended claims when taken in conjunction with the drawings.

FIG. 1A is a block diagram illustrating an existing unsupervised learning technique.

FIG. 1B is a block diagram illustrating an existing supervised learning technique.

Like reference numerals refer to corresponding parts throughout the several views of the drawings.

DETAILED DESCRIPTION

Figure 2:
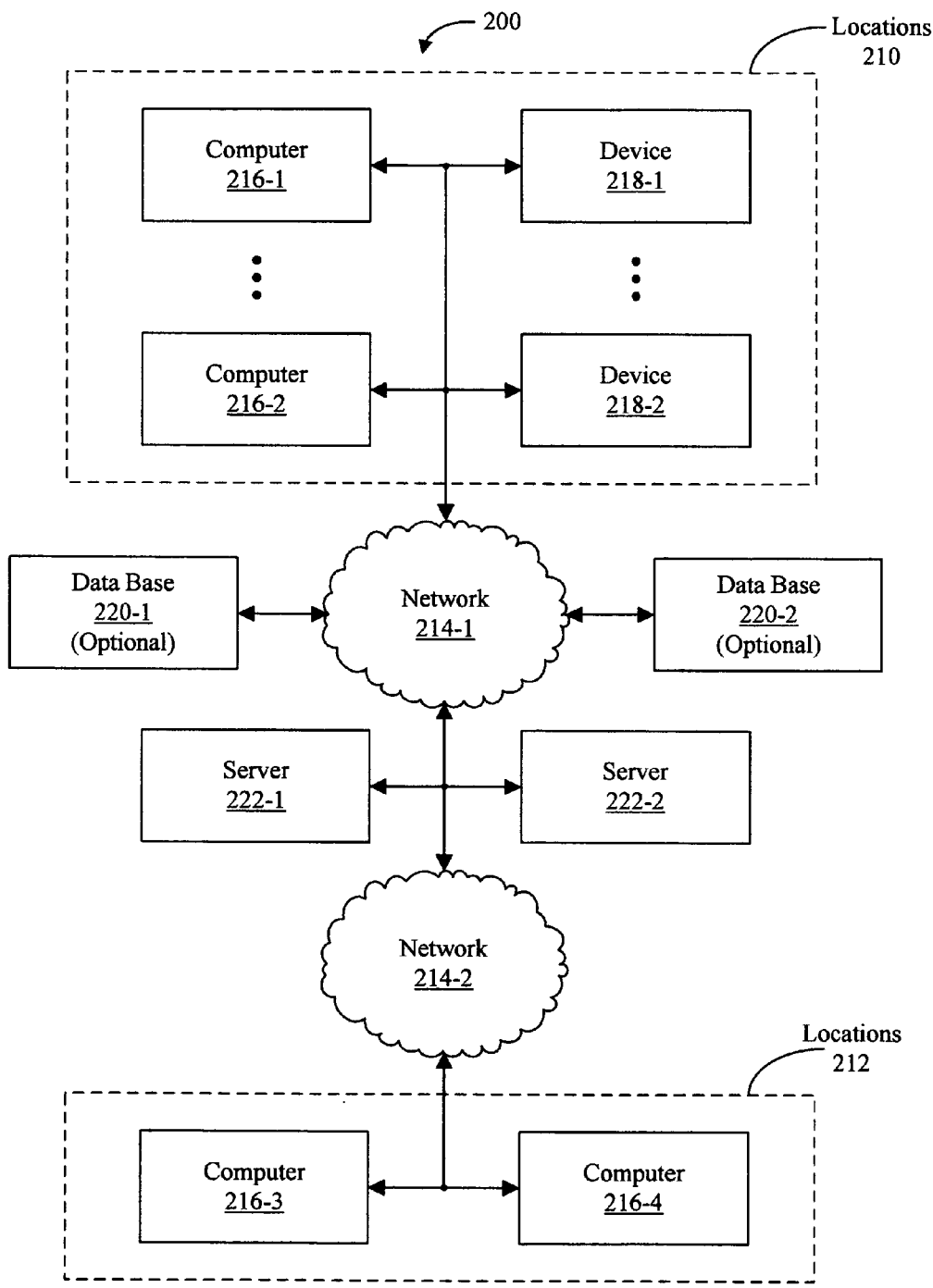
FIG. 2 is a block diagram illustrating an embodiment of a system for collecting and analyzing data, and for providing recommendations.

Reference will now be made in detail to embodiments, examples of which are illustrated in the accompanying drawings. In the following detailed description, numerous specific details are set forth in order to provide a thorough understanding of the present invention. However, it will be apparent to one of ordinary skill in the art that the present invention may be practiced without these specific details. In other instances, well-known methods, procedures, components, and circuits have not been described in detail so as not to unnecessarily obscure aspects of the embodiments.

Embodiments of one or more apparatuses, and related methods, for collecting information and determining one or more association variables are described. The information may be collected by asking a subset of pre-determined questions in a set of pre-determined questions one or more times during a data-collection time interval using the one or more apparatuses.

The subset of pre-determined questions may be varied during the data-collection time interval in accordance with configuration instructions received by the one or more apparatuses. In some embodiments, the configuration instructions correspond to non-executable instructions. The configuration instructions may be transmitted to the one or more apparatuses and answers to a subset of the pre-determined questions, selected in accordance with the configuration instructions, may be received from the one or more apparatuses, for example, using SMS messages and/or email messages.

The subset of pre-determined questions may include pre-selected answers that may be displayed for each question in at least a plurality of pre-determined questions in the subset of pre-determined questions. In some embodiments, answering a respective pre-determined question only involves selection if the respective answer to the respective pre-determined question is different than the respective pre-selected answer. The pre-selected answers may be selected in accordance with an answer history for one or more individuals and/or one or more groups of individuals. In some embodiments, the pre-selected answers may correspond to one or more default answers.

In some embodiments, at least one apparatus or device, such as a personal digital assistant, a tablet computer, a Blackberry, a cellular telephone, and/or a hand-held computer, containing the set of pre-determined questions may be provided to at least one individual. In some embodiments, at least the one individual may be provided a memory card (such as a smart card, a subscriber identity module or SIMS card, and/or a card having ROM, FLASH or other memory) containing the set of pre-determined questions. In some embodiments, at least one server may transmit instructions corresponding to the subset of pre-determined questions to at least one computer. A browser in at least the one computer may render the instructions corresponding to the subset of pre-determined questions. Communication with apparatuses, devices, computers, and/or servers may occur via a network, such as the Internet (also known as the World Wide Web), an Intranet, a local area network (LAN), a wide area network (WAN), a metropolitan area network (MAN), and/or a wireless network.

The one or more association variables may be determined and/or identified, using one or more apparatuses, and/or the related methods, in accordance with one or more statistical relationships between one or more temporal onsets corresponding to one or more events and patterns of occurrence of one or more variables and/or one or more compound variables. The one or more compound variables may be determined using one or more variables in a set of variables. The one or more temporal onsets may include one or more onset times and/or one or more onsets during one or more time intervals.

A respective compound variable may correspond at least to a pattern of occurrence of a first variable during a first time interval preceding the one or more temporal onsets and a pattern of occurrence of a second variable during a second time interval preceding the one or more temporal onsets. The first time interval and/or the second time interval may be offset in time from the one or more temporal onsets. The first time interval may be different than the second time interval. In some embodiments, the respective compound variable may correspond to patterns of occurrence of three of more variables during corresponding time intervals preceding the one or more temporal onsets.

Contributions from presence and absence information in the pattern of occurrence of the one or more compound variables may be included when determining the one or more statistical relationships. The pattern of occurrence of the respective compound variable, such as the pattern of occurrence of the first variable and the pattern of occurrence of the second variable, may include presence and absence information.

The one or more statistical relationships may be determined using a non-parametric analysis technique (which makes few assumptions about an existence of a probability distribution function, such as a normal distribution, corresponding to a population from which samples are obtained, or regarding independence of the variables and/or the compound variables), an unsupervised learning analysis technique, and/or a supervised learning analysis technique. The analysis may perform hypothesis testing to determine if the one or more temporal onsets and the one or more compound variables and/or the one or more variables are statistically independent (or dependent) in accordance with a statistical significance criterion. In the process, the analysis may increase an effective signal-to-noise ratio in an underdetermined problem (i.e., sparse sampling in a multi-dimensional variable space) by restricting a number of local fitting neighborhoods (i.e., a number of relevant variables and/or compound variables).

The one or more compound variables may be ranked in accordance with the one or more statistical relationships. The variables in the set of variables may be ranked in accordance with a number of occurrences of the variables in the compound variables having respective statistical relationships that approximately exceed the statistical confidence threshold corresponding to a noise floor. The statistical confidence threshold may be selected such that at least a subset of the ranking is approximately stable. In some embodiments, a respective ranking may be corrected using a ranking of variables and/or compound variables for which there is no relationship and/or for which there is an inverse relationship between the corresponding pattern of occurrence and the temporal onsets corresponding to one or more events (which is sometimes referred to as a background). In some embodiments, the respective ranking may be corrected using a ranking of variables and/or compound variables that is determined using a random and/or a pseudorandom temporal pattern for the temporal onsets.

One or more variables, such as the first variable and the second variable in the one or more compound variables, may be identified as the one or more association variables. Additional association variables may be identified by associating the one or more association variables with one or more groups of association variables, including pre-determined groups of association variables. One or more recommendations may be provided to at least the one individual in accordance with the one or more association variables. In some embodiments, at least the one individual may be a healthcare provider (such as a physician, nurse, chiropractor, and/or an associated staff member), a parent, a guardian, and/or an individual that has a disease. The one or more recommendations may be included in one or more reports.

The one or more association variables may, at least in part, trigger, initiate, and/or precipitate the one or more events (henceforth referred to as trigger). The one or more association variables may directly or indirectly cause the one or more events. Alternatively, the one or more association variables may not directly or indirectly cause the one or more events. Instead, the one or more association variables may enable the one or more events. To make an analogy, in some embodiments the one or more association variables may function as keys in one or more locks (receptors), allowing a spring-loaded door (corresponding, for example, to a biochemical predisposition or reaction) to open.

In some embodiments, two or more association variables may work in conjunction with one another, i.e., at least the one individual may experience at least one event if at least the one individual is exposed to two or more association variables in close temporal proximity (for example, during a time interval), in a temporal sequence and/or in an ordered temporal sequence (i.e., a particular pattern of exposure to two or more association variables). An effect of the association variables may be cumulative. Exposure to a sufficient quantity of the respective association variable may trigger the one or more events, or exposure to quantities of two or more association variables may trigger the one or more events. Be it cumulative and/or cooperative, the respective association variable may correspond to 5%, 10% 25%, 50% or more of a total trigger for the one or more events. The one or more association variables may be specific to an individual and/or a group of two or more individuals. In some embodiments, the one or more events may correspond to an episodic increase in a severity of one or more symptoms associated with a medical condition, a disease, such as a chronic disease, and/or a disease condition in at least the one individual.

The disease may include a form of arthritis, rheumatoid arthritis, joint disease, an auto-immune disorder, an immune-related disorder, an inflammatory disease, lupus, thyroid disease, gout, diabetes, chronic fatigue syndrome, insomnia, depression, a psychological disease, gastrointestinal disease, colitis, ulcerative colitis, inflammatory bowel disease, Crohn's disease, candida, celiac disease, irritable bowel syndrome, one or more food allergies, one or more food sensitivities, morning sickness, menstrual cramps, chronic pain, back pain, facial pain, fibromyalgia, asthma, migraines, abdominal migraines, cyclic vomiting syndrome, cluster headaches, chronic headaches, tension headaches, another type of headaches, seizures, epilepsy, neurodermatitis, acne, psoriasis, adiposity, hypertonia, heart disease, hypertension, cardiovascular disease, arteriosclerosis, a form of cancer, and/or acquired immune deficiency syndrome. The system and method may also be applied to patients have multiple illnesses, such a geriatric patients.

The embodiments of the apparatuses, and related methods, may be used to collect and analyze information associated with time-varying phenomena having discrete epochs. The embodiments of the apparatuses, and related methods, may also be used to identify one or more association variables for such time-varying phenomena, thereby allowing remedial action to be taken (if appropriate). Technical effects for the embodiments of the apparatuses, and related methods, may include displaying one or more questionnaires, including a plurality of pre-selected answers, on at least one display, transmitting and receiving collected information (such as answers to at least a subset of the one or more questions) using a network, determining one or more statistical relationships in at least one apparatus, identifying one or more association variables in at least one apparatus, transmitting and receiving one or more recommendations and/or one or more reports using the network, and/or displaying the one or more recommendations and/or the one or more reports on at least one display.

The embodiments of the apparatuses, and related methods, may allow collected data or information to be converted into actionable information, such as one or more recommendations. In some embodiments, providing the recommendations to one or more healthcare providers and/or at least the one individual that has the disease may help convert this information into knowledge. The healthcare providers, who practice medicine, may use the knowledge to aid the one or more individuals that have the disease, including prescribing one or more diagnostic tests and/or one or more treatment modalities (for example, a medicine). In the hands of at least the one individual that has the disease, the information may motivate behavior modification that may mitigate or reduce a severity, duration and/or frequency of one or more symptoms associated with the disease.

Attention is now directed towards embodiments of apparatuses, devices, computers, servers, and systems that may be used to implement the collection of information, the statistical analysis and/or the providing of recommendations. FIG. 2 is a block diagram illustrating an embodiment of a system 200 for collecting data or information, analyzing the information, and/or for providing recommendations (for example, in one or more reports). A network 214 couples servers 222 and optional databases 220 (located in one or more additional computers, servers, and/or network attached storage devices) to first locations 210 and second locations 212. The network 214 may include the Internet (also known as the World Wide Web), an Intranet, a local area network (LAN), a wide area network (WAN), a metropolitan area network (MAN), and/or a wireless network (including one or more cellular telephone networks, Bluetooth networks, Wi-MAX networks, and/or Wi-Fi networks using IEEE 802.11a, 802.11b, 802.11g and/or 802.11n).

The first locations 210 may correspond to that of one or more individuals or humans beings. In some embodiments, the one or more individuals may have been diagnosed as having the disease. At least one of the one or more individuals (henceforth referred to as a first individual) may interact with at least one of computers 216 and devices 218. The devices 218 may include one or more personal digital assistants, one or more tablet computers, one or more cellular telephones, one or more hand-held computers, and/or a combination of two or more of these items. One or more of the servers 222 may provide the subset of pre-determined questions one or more times during the data-collection time interval. Pre-determined questions may include questions that are determined prior to the beginning of the data-collection time interval. In some embodiments, the pre-determined questions may be generated for at least the first individual prior to the beginning of the data-collection time interval, for example, in accordance with an optional initial survey and/or analysis of a biological sample taken from the first individual (as discussed further below with reference to FIG. 19). In exemplary embodiments, the data-collection time interval may be approximately a fraction of a day (such as 1, 3, 4 or 6 hours), a day, several days, a week, a month, 2 months, 3 months, 4 months, 6 months, 9 months, a year, several years, and/or a combination of one or more of these items.

In some embodiments, one or more of the servers 222 may provide instructions for a web page corresponding to the subset of pre-determined questions that is rendered in a browser. The instructions for the web page may include embedded JavaScript instructions that may be executed by one or more of the computers 216 and/or devices 218, i.e., the one or more computers 216 and/or devices 218 may function as a virtual machine. In some embodiments, one or more of the computers 216 and/or devices 218 may already contain the subset of pre-determined questions or the set of pre-determined questions. Configuration instructions, which may be non-executable, from the one or more servers 222 may select the subset of pre-determined questions. In other embodiments, at least the first individual may be asked one or more questions that are not pre-determined, such as one or more questions that may be dynamically generated in one or more of the servers 222. Such dynamically generated questions may be provided approximately in real-time during the data-collection time interval.

At least the first individual may provide answers to the subset of pre-determined questions one or more times during the data-collection time interval. The answers may be transmitted to one or more of the servers 222 and/or one or more of the optional databases 220. In some embodiments, the answers are transmitted at least in part using email messages and/or SMS messages, or only using email messages and/or SMS messages. The email messages and/or SMS messages may be compressed and/or encrypted. One or more of the servers 222, in conjunction with information stored in one or more of the optional databases 220, may analyze the answers to determine one or more statistical relations, the ranking of the variables, and/or to identify the one or more association variables. One or more of the servers 222 may revise the subset of pre-determined questions that are provided and/or provide revised configuration instructions, which may be non-executable, to at least one of the computers 216 and devices 218 in order to modify the subset of pre-determined questions for at least the first individual. In some embodiments, the configuration instructions may be provided at least in part using email messages and/or SMS messages, or only using email messages and/or SMS messages. The email messages and/or SMS messages may be compressed and/or encrypted. The configuration instructions may be determined in accordance with the answer history for at least a subset of the one or more individuals, one or more groups of individuals, and/or default answers to the subset of pre-determined questions that may be stored in at least one of the optional databases 220. In some embodiments, the configuration instructions may be in accordance with the analysis of the biological sample taken from the first individual (as discussed further below with reference to FIG. 19)

The second locations 212 may correspond to that of one or more healthcare providers (such as a physician, nurse, chiropractor, and/or an associated staff member), one or more parents, one or more guardians, and/or one or more additional individuals that have the disease (henceforth referred to as a second individual). In some embodiments, one or more of the servers 222, in conjunction with information stored in one or more of the optional databases 220, may provide one or more recommendations in accordance with the one or more determined association variables to at least the second individual. In some embodiments, one or more of the servers 222, in conjunction with information stored in one or more of the optional databases 220, may provide the one or more recommendations in accordance with the one or more determined association variables to at least the first individual at one or more of the first locations 210. The one or more recommendations may be in the form of one or more reports or documents, including soft or hard copies. In some embodiments, the recommendations may be provided by transmitting a data stream including the recommendations and/or transmitting a data stream including instructions corresponding to the recommendations (for example, the instructions may correspond to one or more web-pages) using techniques such as email, SMS, and/or by regular mail.

In other embodiments, at least the first individual may be asked one or more questions that are provided by at least the second individual. Such questions from at least the second individual may be dynamically generated and may be provided approximately in real-time during the data-collection time interval. Answers to these and/or other dynamically generated questions (such as those that may be provided by the one or more servers 222) may be provided to at least the second individual and/or one or more servers 222 approximately in real-time or after a time delay. In some embodiment, at least the second individual may provide feedback and/or instructions to one or more of the servers 222 that is based on the one or more recommendations. In some embodiments, the feedback and/or instructions may be used to revise the configuration instructions. In some embodiments, the feedback and/or instructions may be used to determine one or more additional pre-determined questions that are provided to at least the first individual.

While the system 200 has been shown with two computers 216 and two devices 218 at the first locations 210, and two computers 216 at the second locations 212, there may be fewer or additional computers 216 and/or devices 218. In addition, one or more individuals at the first locations 210 and/or the second locations 212 may share a computer, a device, a set of computers, and/or a set of devices. Similarly, there may be fewer or more servers 222 and/or optional databases 220. One or more functions of one or more of the computers 216, devices 218, servers 222, and/or optional databases 220 may be combined into a single item in the system 200 and/or may be performed at one or more remote locations in the system 200. One or more positions of one or more items in the system 200 may be changed. In some embodiments, the functions of the one or more servers 222 and/or optional databases 220 may be performed in one or more of the computers 216 and/or one or more of the devices 218, for example, using one or more applications programs or modules installed on one or more of the computers 216 or in one or more removable storage medium in one or more of the computers 216. In some embodiments, the one or more applications programs or modules installed on one or more of the computers 216 or in one or more removable storage medium in one or more of the computers 216 may be dedicated or stand-alone applications that function without interactions with one of the servers 222 or only occasionally interact with one or more of the servers 222.

Figure 3:
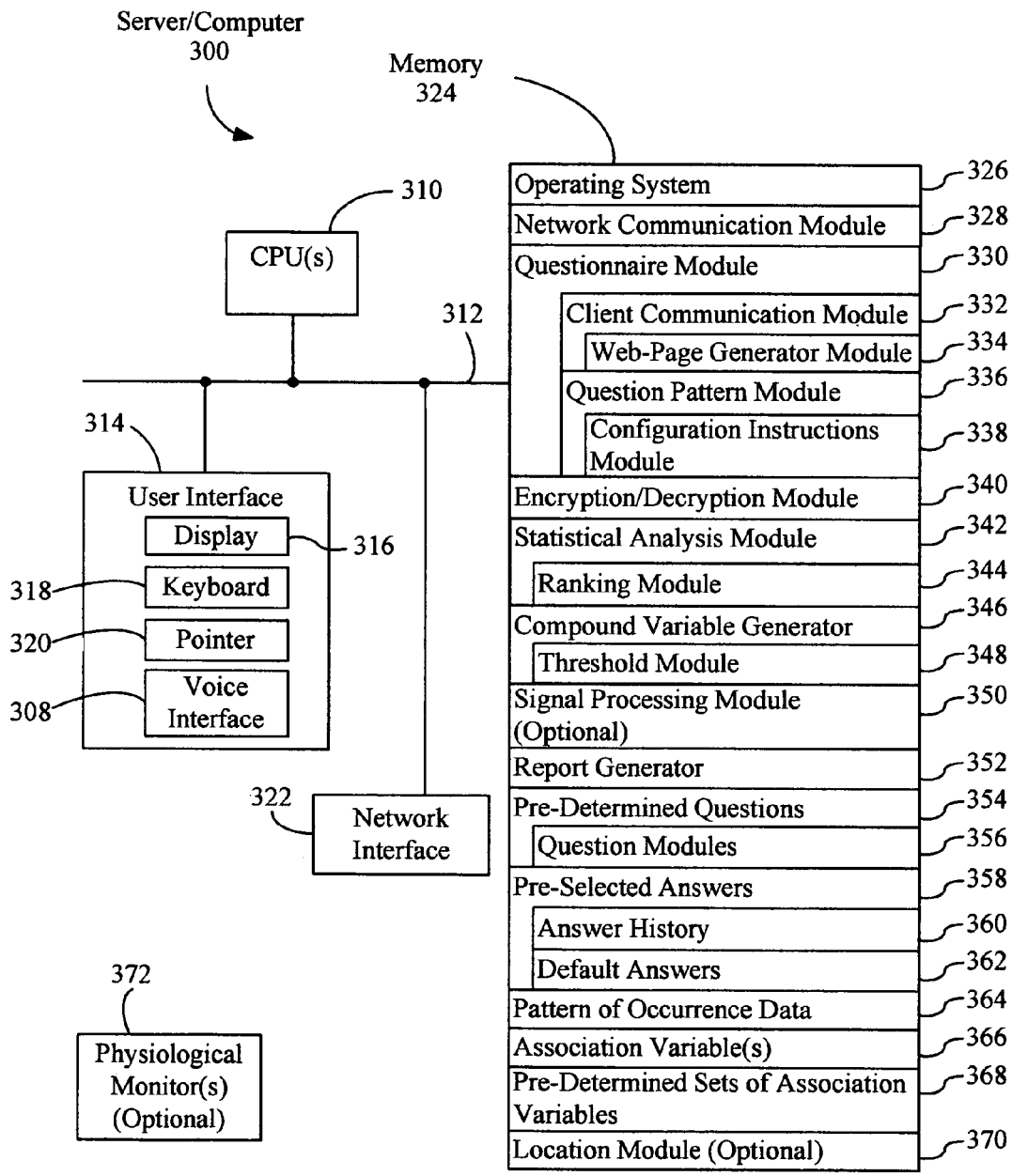
FIG. 3 is a block diagram illustrating an embodiment of a server or computer.

FIG. 3 is a block diagram illustrating an embodiment of a server or computer 300, such as one of the computers 216 and/or servers 222 in FIG. 2. The server or computer 300 includes one or more processing units (CPUs) 310 (which are each a means for computing), at least one network or communications interface 322 for communicating with other computers, servers, devices, and/or databases, a memory device 324 (which is a means for storage) with primary and secondary storage, at least one optional user interface 314, and one or more signal lines 312 for connecting these components. The one or more processing units (CPUs) 310 may support parallel processing and/or multi-threaded operation. The optional user interface 314 may have one or more displays 316, keyboards 318, pointers 320 (such as a mouse), a touchpad (not shown), and/or a voice interface 308, including one or more speakers and/or microphones. The one or more displays 316 may include a touch screen (which may combine the functionality of at least one of the keyboards 318 with at least one of the displays 316). The one or more signal lines 312 may constitute one or more communication buses. The network or communications interface 322 may have a persistent communication connection.

The memory device 324 may include high speed random access memory and/or non-volatile memory, including ROM, RAM, EPROM, EEPROM, FLASH, one or more smart cards, one or more magnetic disc storage devices, and/or one or more optical storage devices. The memory device 324 may store an operating system 326, such as LINUX, UNIX, OS X, or WINDOWS, that includes procedures (or a set of instructions) for handling various basic system services for performing hardware dependent tasks. The memory device 324 may also store procedures (or a set of instructions) in a network communications module 328. The communication procedures may be used for communicating with one or more computers 216 (FIG. 2), servers 222 (FIG. 2), optional databases 220 (FIG. 2), and/or devices 218 (FIG. 2). The communication procedures may include those for a parallel interface, a serial interface, an infrared interface, Bluetooth, Firewire (IEEE 1394A and/or IEEE 1394B), and/or a USB interface (for example, USB-1 and/or USB-2 or High-Speed USB). The communication procedures may include HyperText Transport Protocol (HTTP) to transport information using the Transmission Control Protocol/Internet Protocol (TCP/IP), as well as a secure or encrypted version of HTTP, such as Hypertext Transport Protocol over Secure Socket Layer (HTTPS), a Layer 2 Tunneling Protocol (L2TP), or another Internet Protocol Security, such as IPSEC.

The memory device 324 may also include the following elements, or a subset or superset of such elements, including a questionnaire module (or a set of instructions) 330, an encryption/decryption module (or a set of instructions) 340 (using, for example, pretty good privacy, symmetric encryption, and/or asymmetric encryption), a statistical analysis module (or a set of instructions) 342, a compound variable generator (or a set of instructions) 346, an optional signal processing module (or a set of instructions) 350, a report generator (or a set of instructions) 352 for formatting and providing recommendations and related information to at least one of the first individual and/or the second individual, pre-determined questions (or a set of instructions) 354, pre-selected answers (or a set of instructions) 358, pattern of occurrence data 364 corresponding to one or more events and/or one or more variables, association variable(s) 366, pre-determined sets of association variables 368, and/or an optional location module (or a set of instructions) 370 for determining a location of one or more computers 216 (FIG. 2) and/or one or more devices 218 (FIG. 2) (for example, using an IP address, a global positioning system, and/or remote localization capability associated with a portable device such as a cellular telephone).

The questionnaire module 330 may include a client communication module (or a set of instructions) 332 and/or a question pattern module (or a set of instructions) 336 for providing the subset of pre-determined questions to at least the first individual. The client communication module 332 may include a web-page generator module (or a set of instructions) 334 that generates instructions corresponding to one or more web pages, including HyperText Mark-up Language (HTML), extensible Mark-up Language (XML), Java, JavaScript, Perl, PHIP, and/or .NET. The question pattern module 330 may include a configuration instructions module (or a set of instructions) 338 for providing instructions that select the subset of pre-determined questions. The statistical analysis module 342 may include a ranking module (or a set of instructions) 344. The compound variable generator 346 may include a threshold module (or a set of instructions) 348 for determining if one or more entries in the pattern of occurrence data 364 for at least one variable correspond to a presence or an absence. The pre-determined questions 354 may include one or more question modules (or a set of instructions) 356. The pre-selected answers 358 may include answer history 360 for one or more individuals and/or one or more groups of individuals, and/or default answers (or a set of instructions) 362.

In some embodiments, the server or computer 300 may communicate with one or more optional physiological monitors 372. Communication may be via a cable (such as USB), infrared, Firewire and/or wireless (such as Wi-Fi or Bluetooth). In an alternate embodiment, at least the first individual may manually enter physiological data from the one or more optional physiological monitors 372 using one of the components in the optional user interface 314. In some embodiments, the physiological data may be entered using a binary search procedure corresponding to a series of questions, such as, "Is the physiological data value less than 0.5?," "Is the physiological data value less than 0.25?," "Is the physiological data value greater than 0.375?," and so on until a desired precision is obtained. (A similar binary search procedure may be used to answer one or more pre-determined questions in the subset of pre-determined questions.) Communication with the one or more optional physiological monitors 372 may be at discrete times or it may be continuous. The one or more optional physiological monitors 372 may include an electroencephalogram monitor (such as a Holter monitor), an electrocardiogram monitor (such as a Holter monitor), an electromyleogram monitor, an inflammatory response monitor, a respiratory monitor (such as the Air Watch II) of variables such as peak expiratory flow and/or a forced expiratory volume in 1 second, a blood glucose monitor, a blood pressure monitor, a thermometer, a vital sign monitor (such as those for pulse or respiration rate), a galvanometric response monitor, a psychomotor agitation monitor, and/or a reflex arc monitor.

Instructions in the modules in the memory device 324 may be implemented in a high-level procedural language, an object-oriented programming language, and/or in an assembly or machine language. The programming language may be complied or interpreted, i.e, configurable or configured to be executed by the one or more processing units 310. In addition, the server or computer 300 may include fewer or additional executable procedures, sub-modules, tables, and/or other data structures (not shown). In some embodiments, additional or different modules and data structures may be used and some of the modules and/or data structures listed above may not be used. In some embodiments, the functions of two or more modules may be combined in a single module. In some embodiments, implementation of functionality of the server or computer 300 may be implemented more in hardware and less in software, or less in hardware and more in software, as is known in the art.

Although the server or computer 300 is illustrated as having a number of discrete items, FIG. 3 is intended more as a functional description of the various features that may be present in the server or computer 300 rather than as a structural schematic of the embodiments described herein. In practice, and as recognized by those of ordinary skill in the art, the functions of the server or computer 300 may be distributed over a large number of servers or computers, with various groups of the servers or computers performing particular subsets of the functions. Items shown separately in the server or computer 300 may be combined, some items may be separated and/or additional items may be added. The apparatuses and methods disclosed may be implemented in hardware and/or software. In alternate embodiments, some or all of the functionality of the server or computer 300 may be implemented in one or more application specific integrated circuits (ASICs) and/or one or more digital signal processors (DSPs).

Figure 4:
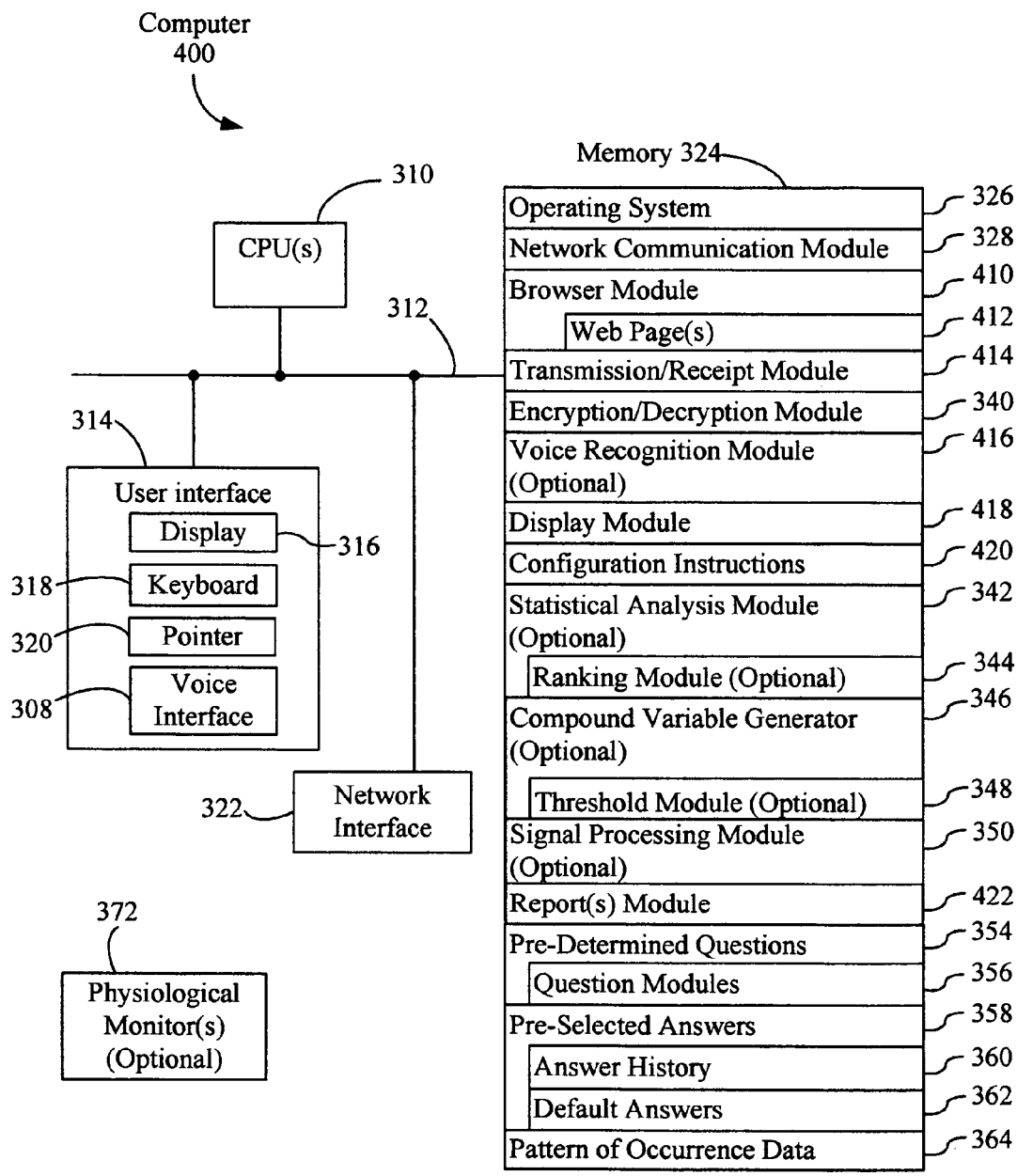
FIG. 4 is a block diagram illustrating an embodiment of a computer.

FIG. 4 is a block diagram illustrating an embodiment of a computer 400, such as one of the computers 216 (FIG. 2). The memory device 324 may include a browser module (or a set of instructions) 410 for rendering web-page instructions, a transmission/receipt module (or a set of instructions) 414 for handling information such the subset of pre-determined questions and corresponding answers, an optional voice recognition module (or a set of instructions) 416, a display module (or a set of instructions) 418 for displaying the subset of pre-determined questions and/or the pre-selected answers to at least the first individual, configuration instructions 420, and/or a report(s) module (or a set of instructions) 422 for formatting and presenting recommendations and related information to at least one of the first individual and the second individual. The browser module 410 may include instructions corresponding to one or more web pages 412. The computer 400 may optionally perform at least a portion of the analysis, such as the determining at least some of the statistical relationships. The computer 400 may store pattern of occurrence data 364 corresponding to one or more events and/or one or more variables. The pattern of occurrence data 364 may be stored temporarily as the subset of pre-determined questions are answered over at least a portion of the data-collection time interval. For example, answers for a respective day may be transmitted at night. In some embodiments, the pattern of occurrence data 364 may be communicated to one or more of the servers 222 (FIG. 2) and/or optional databases 220 (FIG. 2) approximately in real-time, for example, as respective pre-determined questions are answered. In some embodiments, the computer 400 may communicate with one or more optional physiological monitors 372.

Although the computer 400 is illustrated as having a number of discrete items, FIG. 4 is intended more as a functional description of the various features that may be present in the server or computer 400 rather than as a structural schematic of the embodiments described herein. In practice, and as recognized by those of ordinary skill in the art, the functions of the server or computer 400 may be distributed over a large number of servers or computers, with various groups of the servers or computers performing particular subsets of the functions. Items shown separately in the computer 400 may be combined, some items may be separated and/or additional items may be added. The apparatuses and methods disclosed may be implemented in hardware and/or software. In alternate embodiments, some or all of the functionality of the server or computer 400 may be implemented in one or more ASICs and/or one or more DSPs.

Figure 5:
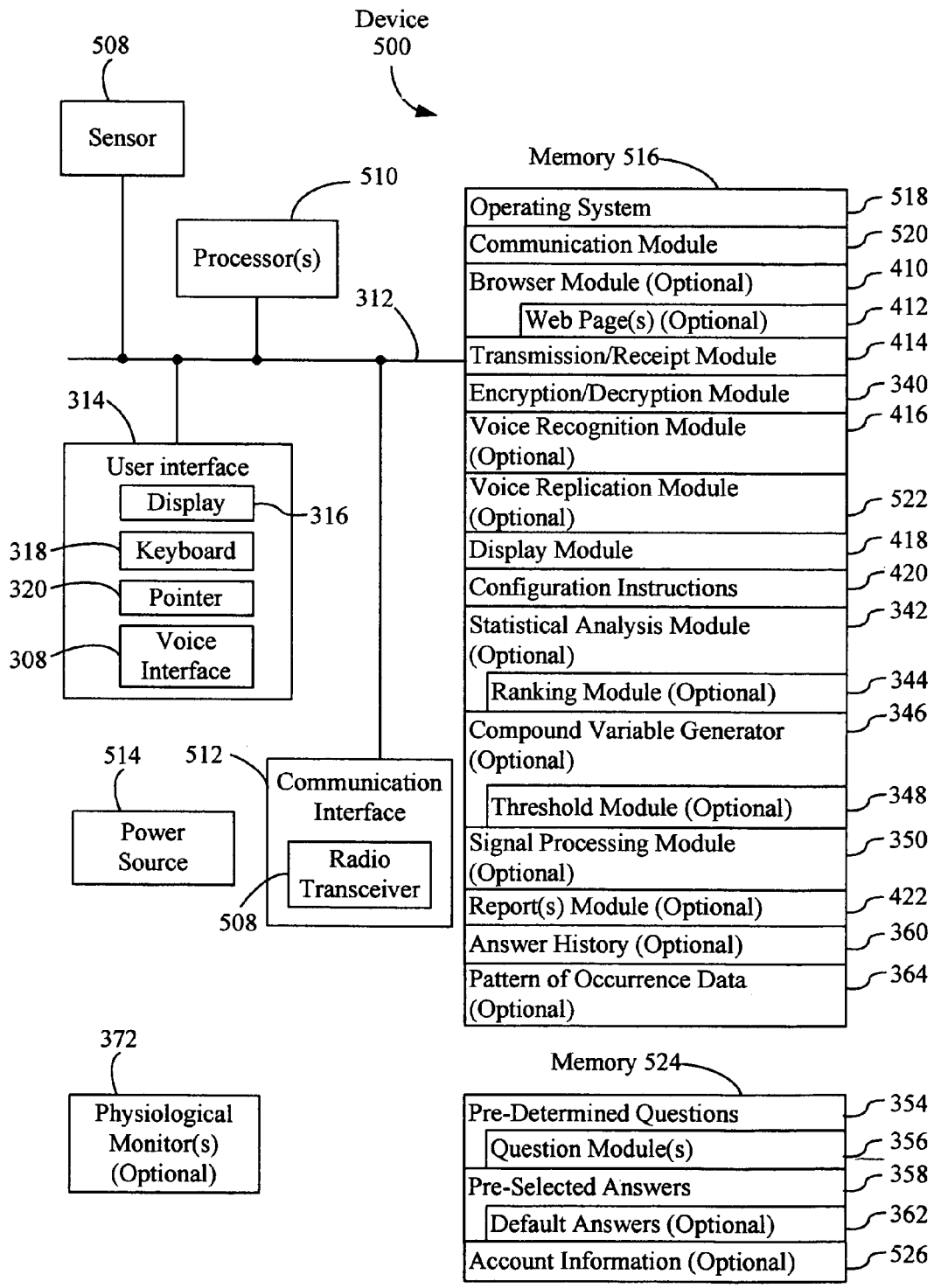
FIG. 5 is a block diagram illustrating an embodiment of a device.

FIG. 5 is a block diagram illustrating an embodiment of a device 500, such as one of the devices 218 (FIG. 2). The device 500 may include a cellular telephone, a personal digital assistant, a tablet computer, a Blackberry, a hand-held computer, and/or a combination of two or more of these items. In some embodiments, the device 500 may be an implantable medical device that collects and communicates data for at least the first individual. The device 500 may include one or more data processors, video processors and/or processors 510 (which are each a means for computing), at least one communications interface 512 for communicating with other computers, servers, devices and/or databases, a first memory device 516 (which is a means for storage) with primary and/or secondary storage, a second optional memory device 524 that may be removable (and which is also a means for storage), at least the one user interface 314, a sensor 508, and one or more signal lines 312 for connecting these components. The one or more data processors, video processors and/or processors 510 may support parallel processing and/or multi-threaded operation. The user interface may have one or more displays 316, keyboards 318, pointers 320 (such as a mouse or a stylus), a touchpad (not shown), and/or a voice interface 308 including one or more speakers and/or microphones. The one or more displays 316 may include a touch screen (which may combine functionality of at least one of the keyboards 318 with at least one of the displays 316). The one or more signal lines 312 may constitute one or more communication buses. The communications interface 512 may include a radio transceiver 508 for converting signals from baseband to one or more carrier bands and/or from one or more carrier bands to baseband. The communications interface 512 may have a persistent communication connection. The device 500 may include a power source 514, such as a battery or a rechargeable battery, for supplying power to one or more of these components. The sensor 508 may be an imaging element, such as CCD array, for capturing one or more images (such as pictures).

The memory device 516 may include high speed random access memory and/or non-volatile memory, including ROM, RAM, EPROM, EEPROM, FLASH, one or more smart cards, one or more magnetic disc storage devices, and/or one or more optical storage devices. The memory device 516 may store an embedded operating system 518, such as LINUX, UNIX, OS X, PALM, Simbian or WINDOWS, or a real-time operating system (such as VxWorks by Wind River System, Inc.) suitable for use in industrial or commercial devices. The operating system 518 may includes procedures (or a set of instructions) for handling various basic system services for performing hardware dependent tasks, including password, token and/or biometric security authentication. The memory device 516 may also store procedures (or a set of instructions) in a communications module 520.

The communication procedures in the communications module 520 may be used for communicating with one or more computers 216 (FIG. 2), servers 222 (FIG. 2), optional databases 220 (FIG. 2), and/or devices 218 (FIG. 2). The communication procedures may include those for a parallel interface, a serial interface, an infrared interface, Bluetooth, Firewire (IEEE 1394A and/or IEEE 1394B), and/or a USB interface (for example, USB-1 and/or USB-2 or High-Speed USB). The communication procedures may include one or more protocols corresponding to a Global System for Mobile Telecommunications (GSM), Code Division Multiple Access (CDMA), a Short Message Service (SMS), an Enhanced Messaging Service (EMS), a Multi-media Message Service (MMS), a General Packet Radio Service (GPRS), a Wireless Application Protocol (WAP), instant messaging, email, TCP/IP, and/or a voice over internet protocol (VoIP). Note that SMS supports communication of up to 160 characters using, for example, text messaging. Email may utilize an email address corresponding to a subscriber's 10-digit telephone number, such as 1234567890@messaging.carrier.com, where 'carrier' may be a cellular telephone provider such as Cingular. EMS includes text formatting, and supports communication of simple black and white images, as well as sound tones. MMS supports communication of a wide variety of media from text to video.

The memory device 516 may also include the following elements, or a subset or superset of such elements, including the optional browser module (or a set of instructions) 410, the transmission/receipt module (or a set of instructions) 414, the encryption/decryption module (or a set of instructions) 340, the optional voice recognition module (or a set of instructions) 416, an optional voice replication module (or a set of instructions) 522 for asking at least some of the subset of pre-determined questions using the voice interface 308, the display module (or a set of instructions) 418, the configuration instructions 420, the optional statistical analysis module (or a set of instructions) 342, the optional compound variable generator (or a set of instructions) 346, the optional signal processing module (or a set of instructions) 350, the optional report(s) module (or a set of instructions) 422, the optional answer history 360, and/or the optional pattern of occurrence data 364.

The optional browser module 410 may include instructions corresponding to one or more web pages 412. The optional statistical analysis module 342 may include the optional ranking module (or a set of instructions) 344. The optional compound variable module 346 may include the optional threshold module (or a set of instructions) 348. The device 500 may optionally perform at least a portion of the analysis, such as determining at least some of the statistical relationships. The encryption/decryption module 340 may include encryption/decryption that is supported in the GSM and/or CDMA protocols. In some embodiments, the encryption/decryption module 340 may include a virtual private network (VPN) tunneling application.

The optional pattern of occurrence data 364 may be stored temporarily as the subset of pre-determined questions are answered over at least a portion of the data-collection time interval. For example, answers for a respective day may be transmitted at night (when communication fees are lower). In some embodiments, the optional pattern of occurrence data 364 may be communicated to one or more of the servers 222 (FIG. 2) and/or optional databases 220 (FIG. 2) approximately in real-time, for example, as respective pre-determined questions are answered.

In an exemplary embodiment, the configuration instructions 420 and the answers to the subset of predetermined questions may be communicating using one or more SMS text messages and/or email messages. In some embodiments, only SMS text messages and/or email messages are used. The use of SMS text messaging and/or email messaging may result in cost savings associated with establishing accounts and/or with the communication. Receipt of a respective SMS text message by an end destination, such as one of the servers 222 (FIG. 2), may be confirmed using a handshake message (such as another SMS message). Upon receipt of such a handshake message, the device 500 may erase and/or delete information that was transmitted in the original SMS text message (such as one or more answers to the subset of pre-determined questions or at least a portion of the optional pattern of occurrence data 364).

In some embodiments, at least the first individual may use the device 500 to collect information that may be subsequently used to answer one or more of the subset of pre-determined questions. For example, the sensor 508 may be used to take a picture of a menu, a table of contents, and/or one or more medicines consumed. Or an audio file listing items consumed during a meal or snack may be recorded. The collected information may be processing in the device 500, or in one or more remote computers and/or one or more servers, using image processing, text recovery/identification, and/or speech recognition (using, for example, the optional voice recognition module 416). In some embodiments, the device 500 may communicate with one or more optional physiological monitors 372.

In some embodiments, the device 500 may provide at least the first individual with at least one reminder (such as a reminder to take a medicine at a respective time) using one or more messages transmitted to the device 500 and/or using one or more pre-stored messages in the device 500 that may be enabled by the configuration instructions 420. At least the one reminder may be provided using the voice replication module 522 and the voice interface 308.

The optional memory device 524 may include one or more FLASH drives, ROMs, memory sticks, optical storage media (such as rewritable or ROM CDs and/or DVDs), smart cards, SIMS cards, secure digital (SD) cards (compatible with devices that use a PALM embedded operating system), multimedia cards (MMCs), magnetic disc storage devices (such as disc drives), and/or magnetic media (such as floppy discs). The optional memory device 524 may also include the following elements, or a subset or superset of such elements, including the pre-determined questions (or a set of instructions) 354, the pre-selected answers 358 (or a set of instructions), and/or the optional account information 526. The pre-determined questions 354 may include the one or more question modules (or a set of instructions) 356. The pre-selected answers 358 may include optional default answers (or a set of instructions) 362. The optional account information 526 may include at least one carrier account number (for an Internet service provider, a cellular telephone provider, and/or a wireless services provider) and/or at least one telephone number that may enable at least the first individual to receive the configuration instructions 420 and to transmit the answers to the subset of pre-determined questions. The optional account information 526 may allow at least the first individual to communicate with one or more providers of services that determine one or more association variables.

In some embodiments, at least first individual is provided with the optional memory device 524, which may be installed in the device 500. One or more additional optional memory devices may also be provided to at least the first individual at later times during the data-collection time interval. The one or more additional optional memory devices may include revised pre-determined questions 354 and/or revised pre-selected answers 358.

In some embodiments, the optional memory device 524 is a SIMS card, an SD card, and/or a memory card and the device 500 includes a cellular telephone. By including the optional account information 526, communication using at least the one carrier account number and/or at least the one telephone number may avoid the so-called SIMS card lock that prevents modification of such information in a cellular telephone that is issued by a cellular telephone provider to a subscriber. This may allow one or more modules or applications to be installed and/or executed on the cellular telephone independently of the cellular telephone provider. Address book and/or additional telephone numbers (such as a list of frequently used telephone numbers) on an existing SIMS card, SD card, and/or memory card for at least the first individual may be copied on to the optional memory device 524. Alternatively, at least the first individual may at least temporarily provide the existing SIMS card, SD card, and/or memory card, which may allow the address book and/or the additional telephone numbers to be copied on to a new optional memory device 524 that may be provided to at least the first individual.

In some embodiments, the pre-determined questions 354 and/or the pre-selected answers 358 may be copied on to the optional memory device 524 or the existing SIMS card, SD card, and/or memory card in a cellular telephone. Service, such as collecting the information, may be provided in conjunction with or separately from one or more cellular telephone service providers. In some embodiments, revised pre-determined questions 354 and/or revised pre-selected answers 358 may be transmitted to and stored on the optional memory device 524 on one or more occasions during the data-collection time interval.

In some embodiments, at least the first individual owns or rents the device 500, thereby reducing a cost associated with collecting information, as well as a cost and complexity associated with supporting and maintaining hardware in the field. In some embodiments, at least the first individual is provided, either temporarily or permanently, with the device 500. Furthermore, in some embodiments memory 524 is included in the device 500 when it is provided to the first individual. Thus, the device 500 is pre-configured or pre-loaded with the pre-determined questions 354.

The modules and/or some components in the memory device 516 may be arranged in a protocol stack, including a physical layer, a link layer, a network layer, a transport layer, and/or an application layer. In an alternate embodiment, the protocol stack may include the network layer, the transport layer, a security layer, a session transaction layer, and/or the application layer. Instructions in the modules in the memory device 516 may be implemented in a high-level procedural language, an object-oriented programming language, and/or in an assembly or machine language. The programming language may be complied or interpreted, i.e, configurable or configured to be executed by one or more processors 510. In addition, the device 500 may include fewer or additional executable procedures, sub-modules, tables and other data structures (not shown). In some embodiments, additional or different modules and data structures may be used and some of the modules and/or data structures listed above may not be used. In some embodiments, the functions of two or more modules may be combined in a single module. In some embodiments, implementation of functionality of the device 500 may be implemented more in hardware and less in software, or less in hardware and more in software, as is known in the art.

Although the device 500 is illustrated as having a number of discrete items, FIG. 5 is intended more as a functional description of the various features which may be present in the device 500 rather than as a structural schematic of the embodiments described herein. In practice, and as recognized by those of ordinary skill in the art, the functions of the device 500 may be distributed over a large number of servers or computers, with various groups of the servers or computers performing particular subsets of the functions. Items shown separately in the device 500 may be combined, some items may be separated and/or additional items may be added. One or more items or modules in the memory device 516, such as the configuration instructions 420, may be stored in the optional memory device 524 and vice versa. The apparatuses and methods disclosed may be implemented in hardware and/or software. In alternate embodiments, some or all of the functionality of the device 500 may be implemented in one or more ASICs and/or one or more DSPs.

Figure 6A:
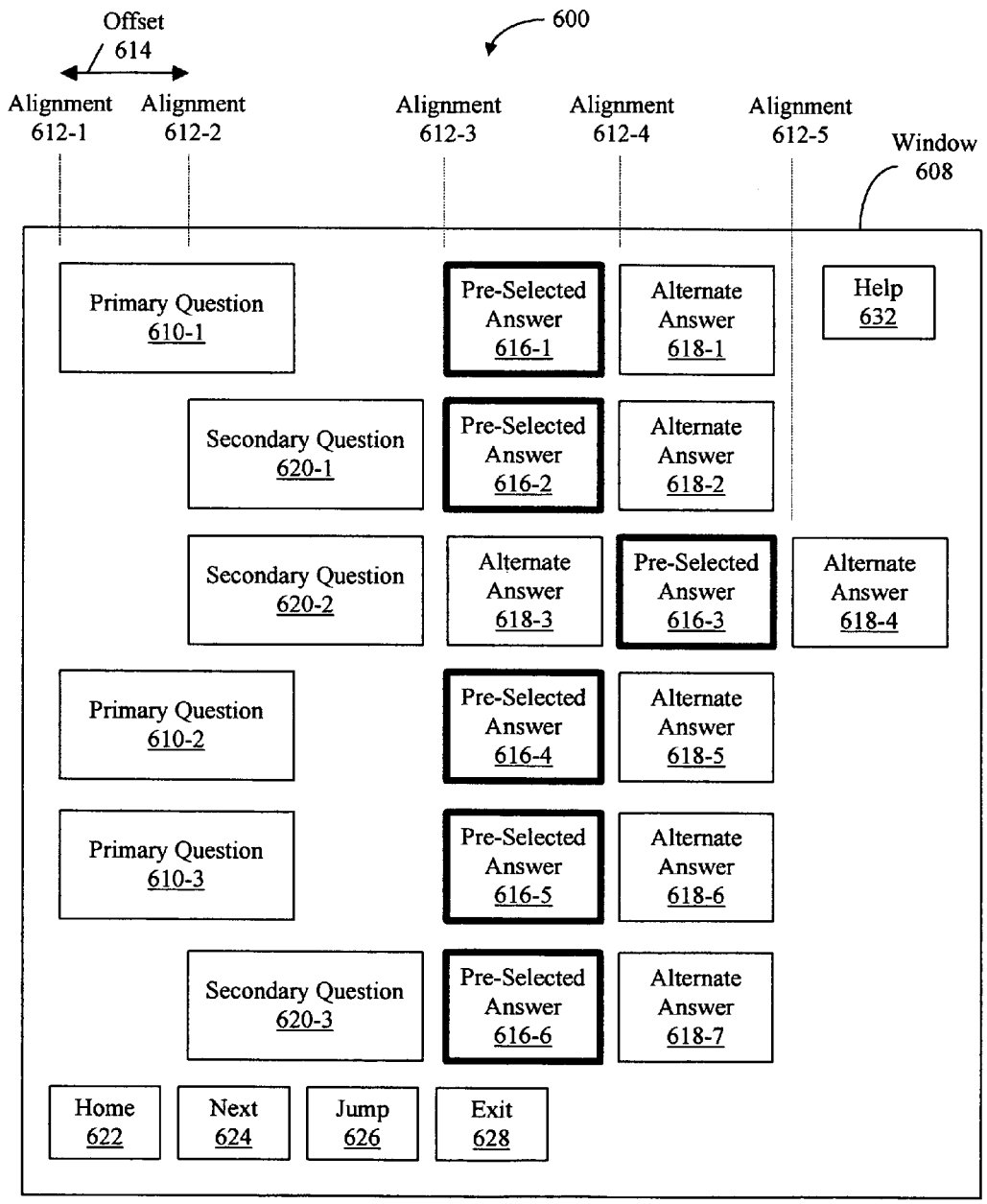
FIG. 6A is a block diagram illustrating an embodiment of a user interface.
Figure 6B:
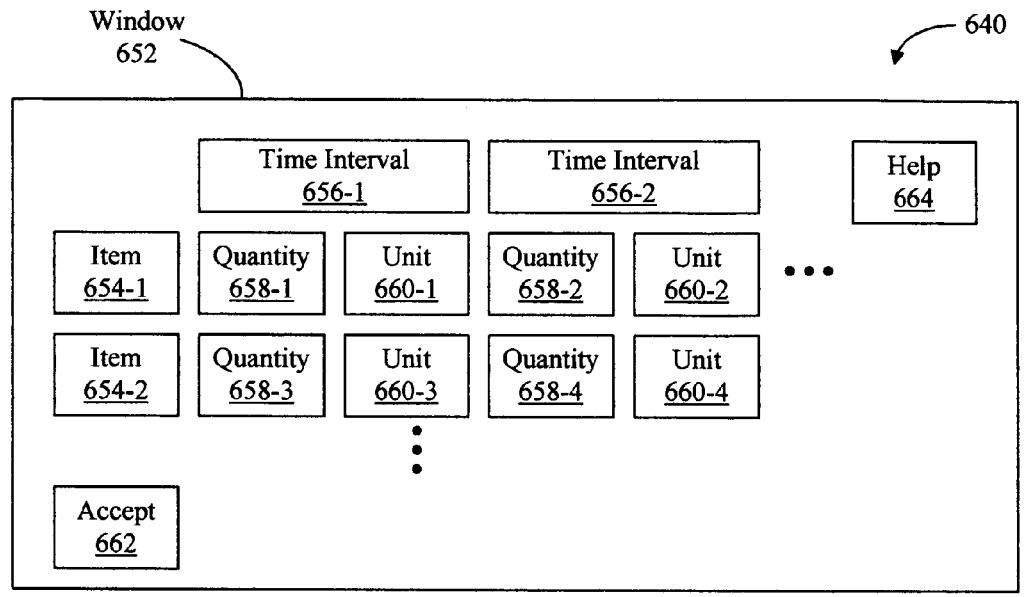
FIG. 6B is a block diagram illustrating an embodiment of a user interface.
Figure 6D:
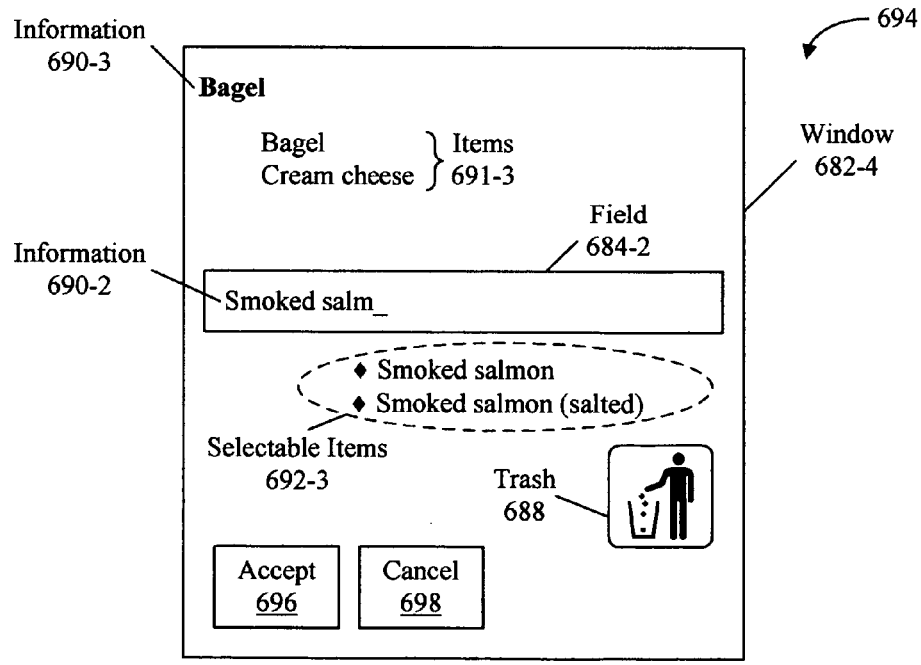
FIG. 6D is a block diagram illustrating an embodiment of a user interface.
Figure 6C:
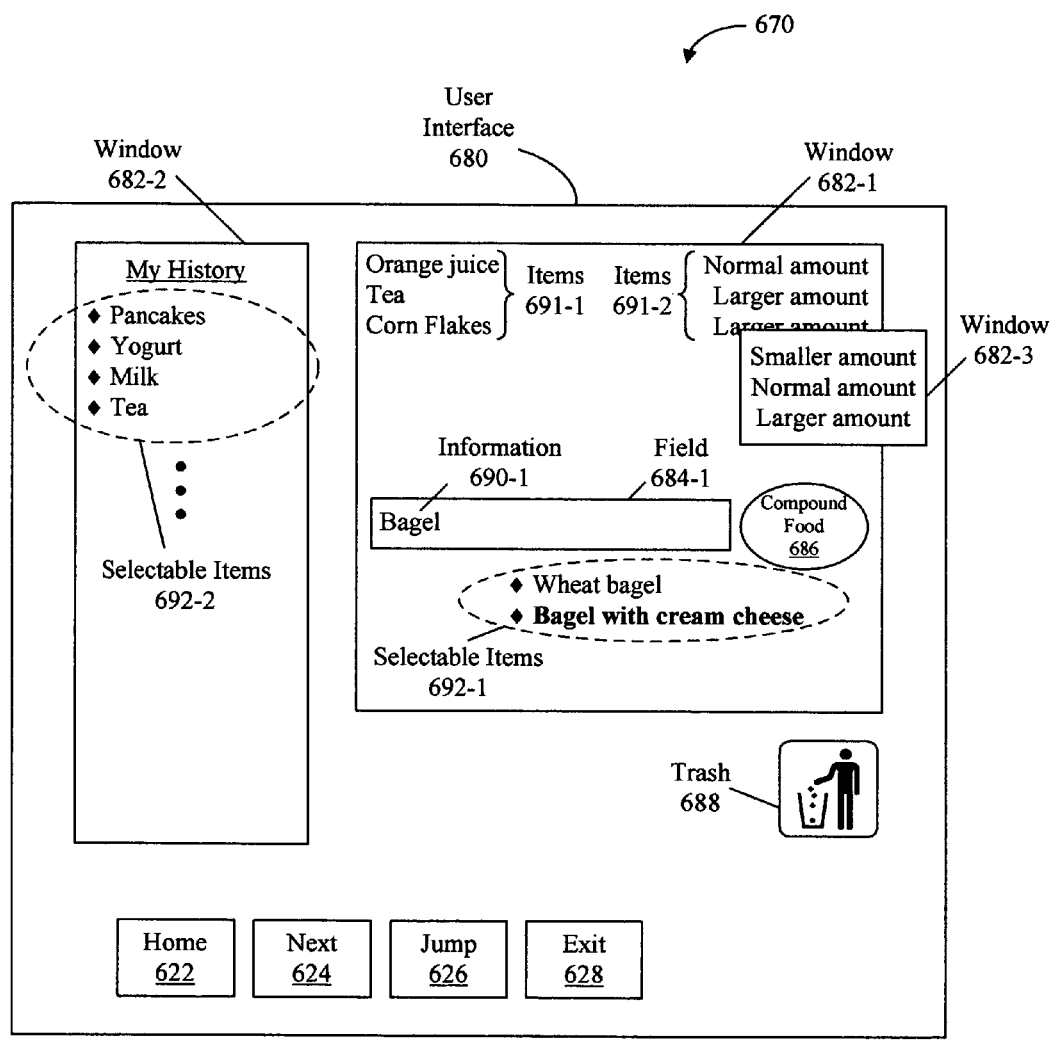
FIG. 6C is a block diagram illustrating an embodiment of a user interface.

Attention is now directed towards embodiments of the questionnaire and formats, including graphical user interfaces, for displaying information contained in embodiments of the questionnaire. As noted previously, the subset of pre-determined questions may be provided (for example, displayed) to at least the first individual along with respective pre-selected answers for each question in at least a plurality of the pre-determined questions in the subset of pre-determined questions. In this way, answering a respective pre-determined question may involve selection if a respective answer to the respective pre-determined question is different than a respective pre-selected answer. The pre-selected answers may be selected in accordance with an answer history, such as the answer history 360 (FIG. 3), and/or default answers, such as the default answers 362 (FIG. 3). FIGS. 6A-6B illustrate embodiments of user interfaces that include pre-determined questions and pre-selected answers. FIGS. 6C-6D illustrate embodiments of user interfaces for receiving information corresponding to foods and beverages that were consumed by the first individual during a meal, a snack, and/or during a time interval.

FIG. 6A is a block diagram illustrating an embodiment of a questionnaire 600, such as a questionnaire module (which may contain related questions in a category of questions). Questionnaire modules are discussed further below with reference to FIGS. 8A and 8B. In the questionnaire 600, several primary questions 610, including pre-selected answers 616 and alternate answers 618, are displayed in a window 608. The window may be a graphical user interface, such as a dialog box or window, and it may be displayed on a display, such as the display 316 (FIG. 4). A left edge of at least a plurality of the primary questions 610 may be aligned with alignment 612-1 such that the primary questions 610 are arranged in a column. A left edge of at least a plurality of the pre-selected answers 616 may be aligned with alignment 612-3 such that the pre-selected answers 616 are arranged in a column. A left edge of at least a plurality of the alternate answers 618 may be aligned with alignment 612-4 such that the alternate answers 618 are arranged in a column. In other embodiments, a right-edge, a center or another position in the primary questions 610, the pre-selected answers 616 and/or the alternate answers 618 may be used for purposes of alignment.

If the pre-selected answers 616 are correct, at least the first individual may select a next 624 icon at the bottom of the window 608 (for example, by positioning a cursor over the accept 624 icon and left clicking on a mouse, or by touching or making a gesture on a touch screen) to accept the pre-selected answers 616 and request another window (unless the questionnaire 600 is completed) with additional pre-determined questions and/or pre-selected answers. Selection of one or more of the alternate answers 618, such as alternate answer 618-1, may occur if a corresponding pre-selected answer 616-1 is not the correct answer for a corresponding primary question, such as primary question 610-1.

If one or more of the alternate answers 618 are selected, secondary questions 620 may be displayed and/or enabled (i.e., at least the first individual may be able to modify the answer to a secondary question, such as secondary question 620-1). In some embodiments, when an alternate answer, such as alternate answer 618-1 is selected, a displayed color of one or more of one or more previously displayed secondary questions 620 may be changed, for example, from grey to black or from white to black. Note that some primary questions 610 may not have one or more associated secondary questions 620 associated with them. The secondary questions 620 may dependent on or may be conditional on the answers to corresponding primary questions 610. A left edge of at least a plurality of the secondary questions 620 may be aligned with alignment 612-2 such that the secondary questions 620 are arranged in a column. In other embodiments, a right-edge, a center or another position in the secondary questions 620 may be used for purposes of alignment. The alignment 612-2 may be offset 614 from the alignment 612-1.

In the questionnaire 600, the primary questions 610 may be categorical or discrete questions, i.e., having answers such as 'yes' or 'no'. In some embodiments, the pre-selected answers

616 may include both 'yes' and 'no' responses. As a consequence, the pre-selected answers 616 may alternate between 'yes' and 'no' for different primary questions 610. In an alternate embodiment, 'yes' answers may be arranged in a first column and 'no' answers may be arranged in a second column, such that a position for the pre-selected answers 616 and the alternate answers 618 may varying between the first column and the second column depending on the primary questions 610. In the questionnaire 600, the secondary questions 620 may include categorical questions as well as one or more ordered categorical secondary question 620-2. (A left edge of the alternate answer 618-4 may be aligned with alignment 612-5. In other embodiments, a right-edge, a center or another position in the alternate answer 618-4 may be used for purposes of alignment.) In an ordered categorical question, there is an ordering between values (such as answers of 'small', 'medium,' or 'large') but a scale or metric value may vary (a difference between 'medium' and 'small' may be different than a difference between 'large' and 'medium'). In some embodiments, an ordered categorical question may have a pre-selected answer, such as pre-selected answer 616-3, that is in a different column than other pre-selected answers 616. This may be useful when the ordered categories are time intervals (such as 3 and/or 6 hours, or morning and/or afternoon, etc.), and the pre-selected answer is not the left-most ordered category. Rather than rearranging the ordered categories, the pre-selected answer 616-3 may be in a different column.

In some embodiments, the primary questions 610 and the secondary questions 620 may include categorical, ordered categorical and/or quantitative questions. Quantitative questions have answers that are continuous variables. Answers to quantitative questions may be partitioned, for example using one or more thresholds or threshold values, to generate categorical or ordered categorical answers. In some embodiments, answers to one or more quantitative questions may be band limited prior to partitioning to reduce or eliminate aliasing. Categorical or ordered categorical answers may be converted into continuous answers using interpolation (such as minimum bandwidth interpolation), subject to the limitations associated with the Nyquist sampling criterion.

In the questionnaire 600, the window 608 may include one or more help icons 632, a home icon 622 to return to a master page in the questionnaire 600, a jump icon 626 to save answers and skip to another window, an exit icon 628 to save answers and exit the questionnaire 600. While the questionnaire 600 includes three primary questions 610 and three secondary questions 620, there may be fewer or more of either type of question. In some embodiments, a respective question may have one or more answers. In some embodiments, one or more additional questions may be included on some occasions when the questionnaire 600 is displayed in order to keep the questionnaire from becoming predictable, and thus less interesting, to the first individual. The one or more additional questions may be displayed with a different color and/or font than the other questions in the questionnaire 600.

FIG. 6B is a block diagram illustrating an embodiment of a questionnaire 640. Selection of a respective alternate answer, such as alternate answer 618-6 (FIG. 6A), to one of the primary questions 610 (FIG. 6A) or secondary questions 620 (FIG. 6A) may lead to window 652 being displayed. The window 652 may include one or more help icons 664, and one or more items 654 with one or more quantities 658 and units 660 (henceforth collectively referred to as entries) during corresponding time intervals 656. At least the first individual may accept the entries using an accept icon 662 after making modifications (if any). Modifications may be made to one or more entries by positioning a cursor over an entry and manually typing one or more new values and/or by left clicking on the mouse with the cursor over the entry and selecting a new value from a list box (a static object in the window 652) that appears when the mouse is positioned over it and/or a content-dependent list or menu (a dynamic object) that may appear as a separate window when the mouse is positioned over it. A list box and/or a content-dependent list or menu may include related objects and/or items, such as those corresponding to a category of items. In some embodiments, the entries in the window 652 may blink to indicate that at least the first individual may modify one or more of them. In an exemplary embodiment, the items 654 may include pharmacological agents, prescription drugs, vitamins, herbs, supplements and/or recreational or illicit drugs (henceforth referred to as pharmacological agents). The quantities 658 and units 660 may correspond to dosages. The time intervals 656 may be a fraction of a day, such as approximately 1, 2, 3, 4, 6, 8, and/or 12 hours. Thus, 50 mg of a drug taken in the morning (such as between 6 AM and 11.59 AM), may correspond to a quantity 658-1 of '50' and a unit 660-1 of 'mg'. The entries in the window 652 may be pre-selected based on the answer history, default answers, and/or answers to one or more questions in the optional initial survey, which may include information about pharmacological agents (such as times taken and dosages) that are prescribed to and/or used by at least the first individual. The optional initial survey may be conducted prior to or at the beginning of the data-collection time interval during which the subset of pre-determined questions corresponding to the questionnaire are asked.

FIG. 6C is a block diagram illustrating an embodiment 670 of a user interface 680, such as a graphical user interface. The user interface 680 includes a first window 682-1 to receive and display information corresponding to a first item consumed by an individual during a first time interval. The first time interval may correspond to a snack or a meal, such as lunch. In some embodiments, snacks eaten between meals may be included in the nearest previous meal and/or the nearest subsequent meal. For example, a snack after dinner and before breakfast may be included with the entries for dinner. A user, such as the first individual, may provide information 690-1 that is displayed in a field 684-1. In an exemplary embodiment, the first individual provides the information 690-1 using an entry device, such as a keyboard, or verbally (in which case voice recognition module 416 in FIG. 4 may be used). The information 690-1 may correspond to one or more foods and/or one or more beverages consumed by the first individual. The information 696-1 may include brand information, such as a manufacturer or a restaurant, corresponding to the one or more foods and/or the one or more beverages consumed by the first individual.

One or more selectable items 692-1 may be determined and displayed in accordance with at least a portion of the information 690-1, such as one or more characters in the information 690-1. In some embodiments, the one or more selectable items 692-1 may be determined using a search vector. The search vector may include one or more synonyms for one or more characters in at least the portion of the information 690-1. Furthermore, the search vector may include one or more alternative spellings for one or more characters in at least the portion of the information 690-1. The search vector may also include a reordering of and/or may exclude one or more characters in at least the portion of the information 690-1.

In some embodiments, the one or more selectable items 692-1 may be determined in accordance with a match score between the search vector and one or more of the one or more selectable items 692-1. The match score may correspond to a weighted summation of terms. A respective term and a respective weight in the summation may correspond to agreement between an item in the search vector (such as a synonym for one or more characters in at least the portion of the information 690-1) and a food or beverage in a list of foods and/or beverages. In some embodiments, the one or more selectable items 692-1 may be determined in accordance with natural language processing.

The first individual may select one of the select items 692-1, for example, by positioning a mouse over a respective item and clicking the left button, or by touching or making a gesture on a touch screen. A respective item that is selected or provided (such as the information 690-1) may be displayed along with other items 691-1 that have been previously selected and/or provided. For example, the respective item may be at the top or the bottom of the other items 691-1.

The items 691-2 may also be displayed along with items 691-1. The items 691-2 may correspond to food amounts or quantities for the corresponding items 691-1. The items 691-2 may include one or more default quantities, such as a normal amount or a usual amount consumed by the first individual. The default quantity for each of the selected items 691-1 may be in accordance with the answer history. The first individual may change a respective default quantity, for example by positioning a mouse over a respective item and clicking the right button, or by touching or making a gesture on a touch screen. In response to such an action by the first individual, a window 682-3 may be displayed. The window 682-3 may include other categorical answers for food quantities, such as smaller amount ('less than usual') and/or larger amount ('more than usual'). The first individual may select one of these quantities using a mouse, or by touching or making a gesture on a touch screen.

The user interface 680 may also include a second window 682-2. The second window 682-2 may include one or more selectable items 692-2 that correspond to one or more foods and/or beverages consumed by the first individual during a second time interval. In some embodiments, the second time interval precedes and/or at least partially overlaps the first time interval. In some embodiments, the second time interval includes the first time interval. In an exemplary embodiment, one or more selectable items 692-2 may correspond to foods and/or beverages consumed by the first individual during previous meals and/or snacks. The one or more selectable items 692-2 may include the most common foods (for example, a top-10 list) consumed by at least the first individual, for example, during a given meal. The first individual may select one or more of the one or more selectable items 692-2 using a mouse, or by touching or making a gesture on a touch screen. Selected items in the one or more selectable items 692-2 may be displayed in the first window 682-1 along with the items 691-1.

The first individual may correct errors in the items 691-1 (for example, if a respective item was selected by accident) by clicking on the respective item using a mouse or by touching the respective item and maintaining contact (in embodiments with a touch screen) and dragging the respective item to a trash icon 688. When the respective item is removed from the items 691-1, the corresponding item in the items 691-2 is no longer displayed.

In some embodiments, the first individual may define a compound food by selecting a compound food icon or button 686 (for example, using a mouse, or by touching or making a gesture on a touch screen). A compound food item, for example, a dish such as lasagna, includes one or more ingredients and may be displayed along with the other selectable items 692-1 and/or 692-2. A user interface for defining such a compound food is described below with reference to FIG. 6D.

The user interface 680 may be implemented as a method and/or as a computer-program product that is to be used in conjunction with a computer system and/or a device. In embodiments where windows in the user interface 680 are provided in one or more web pages, instructions included with the one or more web pages may allow the first window 682-1 to be updated without blinking the displayed user interface 680, i.e., without transmitting revised web page instructions from a remote server or computer, such as the server computer 300 (FIG. 3). The user interface 680 may include one or more help icons (not shown), the home icon 622, the next icon 624, the jump icon 626 and/or the exit icon 628. In some embodiments, the user interface 680 may include additional or fewer elements, such as windows 682, two or more elements may be combined into a single element, and/or a relative position of one or more elements may be changed.

FIG. 6D is a block diagram illustrating an embodiment of a user interface 694, such as a graphical user interface, for receiving two or more ingredients in a respective compound food. A window 682-4 includes information 690-3 corresponding to a name for the respective compound food. The information 690-3 may have been provided by the first individual while interacting with the user interface 680 (FIG. 6C). The window 682-4 may include a field 684-2 that displays information 690-2 provided by the first individual. In an exemplary embodiment, the first individual provides the information 690-2 using an entry device, such as a keyboard, or verbally (in which case voice recognition module 416 in FIG. 4 may be used). The information 690-2 may correspond to one or more ingredients in the respective compound food. One or more selectable items 692-3 may be displayed in accordance with at least a portion of the information 690-2, such as one or more characters in the information 690-2, in a fashion similar to that described above for the user interface 680 (FIG. 6C).

The first individual may select one of the select items 692-3, for example by positioning a mouse over a respective item and clicking the left button, or by touching or making a gesture on a touch screen. A respective item that is selected or provided (such as the information 690-2) may be displayed along with other items 691-3 that have been previously selected and/or provided.

The first individual may correct errors in the items 691-3 (for example, if a respective item that selected by accident) by clicking on the respective item using a mouse or by touching the respective item and maintaining contact (in embodiments with a touch screen) and dragging the respective item to the trash icon 688.

The user interface 694 may be implemented as a method and/or as a computer-program product that is to be used in conjunction with a computer system and/or a device. In embodiments where windows in the user interface 694 are provided in one or more web pages, instructions included with the one or more web pages may allow the window 682-4 to be updated without blinking the displayed user interface 694, i.e., without transmitting revised web page instructions from a remote server or computer, such as the server computer 300 (FIG. 3). The user interface 694 may include an accept icon 696 and a cancel icon 698. Activating and/or selecting the cancel icon 698 may close the user interface 694 without defining a compound food. Activating and/or selecting the accept icon 696 may close the user interface 694 and define a compound food. Compound foods may be highlighted (for example, using a different font and/or a different color than other text) and/or shown in bold in the user interface 680 (FIG. 6C).

In some embodiments, the user interface 694 may include additional or fewer elements, a relative position of one or more elements may be changed, and/or two or more elements may be combined into a single element.

A better understanding of the questionnaire and the determining of one or more association variables (described further below with reference to FIGS. 9-14) may be provided by considering application to a class of problems, such as those associated with one or more diseases. Migraines are used as an illustrative example. In this example, at least the first individual may be a migraine patient. In some embodiments, migraines may include probable migraine, also referred to as migrainous, in which patients exhibit migraines minus one migraine symptom (which are discussed below).

Migraine is a neurovascular disorder characterized by a family of symptoms that often include severe, recurring headache usually on one-side of the head. Migraine attacks are debilitating and have a duration that may last from several hours to days. During attacks, many patients also exhibit sensitivity to environmental stimuli, such as light and sound, and/or experience nausea or vomiting. Some characteristics of migraines, with and without aura, are summarized in Tables I and II. Migraines typically follow a cycle, including an initial or prodrome phase during which premonitory symptoms (discussed further below with reference to FIG. 8A) may be present, an aura phase (for patients that have migraine with aura) during which visual disturbances may be present, a resolution or recovery phase, and a normal (i.e., non-migraine) phase.

TABLE I

Some characteristics of migraine without aura.

A. Headache attacks lasting 4-72 hours (untreated or unsuccessfully treated).
B. Headache has at least two of the following characteristics:
    1. Unilateral location;
    2. Moderate or severe pain intensity;
    3. Pulsating quality;
    4. Aggravated by or causing avoidance of routine physical activity (for example, walking or climbing stairs).
C. During headache at least one of the following:
    1. Nausea and/or vomiting;
    2. Light sensitivity (photophobia) and sound sensitivity (phonophobia).

TABLE II

Some characteristics of migraine with aura.

A. Aura consisting of at least one of the following, but no motor weakness:
    1. Fully reversible visual symptoms including positive features (for example, flickering lights, spots or lines) and/or negative features (such as, loss of vision);
    2. Fully reversible sensory symptoms including positive features (such as, pins and needles) and/or negative features (such as, numbness);
    3. Fully reversible dysphasic speech disturbance.
B. At least two of the following:
    1. Homonymous visual symptoms and/or unilateral sensory symptoms;
    2. At least one aura symptom develops gradually over ≧5 minutes and/or different aura symptoms occur in succession over ≧5 minutes;
    3. Each symptom lasts ≧5 and ≦60 minutes.

TABLE II-continued

Some characteristics of migraine with aura.

C. Headache fulfilling criteria A-C for migraine without aura (Table I) begins during the aura or follows aura within 60 minutes.

The medical approach to managing migraine headaches is typically three-pronged, including acute therapy, preventive therapy, and identification and avoidance of migraine triggers. Acute therapy includes administering acute or prophylactic pharmacological agents, such as painkillers or analgesics, (for example, aspirin, acetaminophen or naproxen), ergotamine, dihydroergotamine, and/or a new class of medications known as "triptans" (selective serotonin 5-hydroxytryptamine or 5-HT receptor agonists, such as imitrex and maxalt), which are migraine-specific medications that may treat the entire migraine complex, relieving the head pain, nausea, vomiting, and associated light and sound sensitivity, typically within 1-2 hours. Most patients with migraine are prescribed one or more forms of acute therapy.

Preventive therapy includes pharmacological agents or medications taken on a daily basis to reduce migraine headache frequency (a number of headaches during a time period), duration and/or severity (for example, a rating of headache pain by a patient such as the first individual). These pharmacological agents may be taken whether a migraine headache is present or not. Prevention strategies are typically employed for patients who suffer from one or more migraine headaches per week. Only a minority of patients require this form of therapy.

Identification and avoidance of migraine triggers is typically a mainstay in the treatment of patients suffering from migraine. If patients successfully avoid their migraine triggers, migraine headache frequency, duration and/or severity may be improved. (Note that some migraine triggers, such as certain hormones, may be intrinsic or internal to the patient. As such, the patient may still have spontaneous migraine attacks even if he or she successfully avoids his or her dominant migraine triggers.) Identifying migraine triggers, however, remains challenging and is often a source of frustration for patients and healthcare providers. This is partly an outgrowth of the apparent complexity of migraine triggers. A myriad of probable or putative migraine triggers are thought to exist. It has been hypothesized that the migraine triggers may vary significantly from one patient to another, may vary within a respective patient (as discussed below with reference to FIG. 7, the respective patient's sensitivity threshold for a respective trigger may vary as a function of time), may depend on a quantity of exposure, and/or may depend on exposure to two or more triggers in close temporal proximity, i.e., during a time interval.

In addition, current approaches for screening for migraine triggers may pose challenges. Typically, patients are given paper diaries and are asked to list what they think may have triggered an attack on a respective day. This approach may rely on the patients' recall of events, as diaries are often filled in days after a migraine attack, and may therefore miss an exposure to migraine triggers. Patients may also assign a cause when one may not exist, or patients may assign blame to an incorrect variable(s). The apparent complexity of migraine triggers may compound these difficulties.

Figure 7:
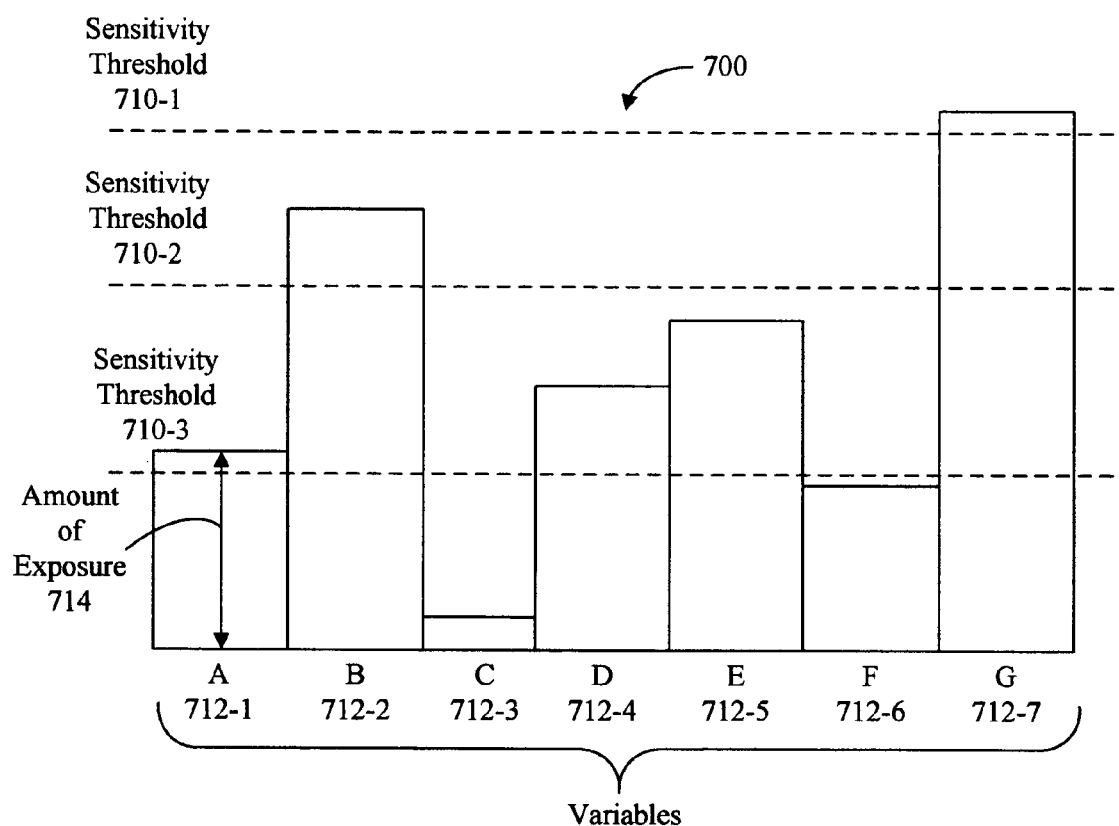
FIG. 7 is a block diagram illustrating an embodiment of migraine triggers and sensitivity thresholds.

FIG. 7 is a block diagram illustrating an embodiment 700 of migraine triggers and sensitivity thresholds. A plurality of variables 712, corresponding to migraine triggers, each having a length corresponding to an amount of exposure 714 during a time interval are illustrated. Sensitivity thresholds 710 illustrate several effective sensitivities for at least the first individual. At any given time, one or more of the sensitivity thresholds 710 may be operative for one or more of the variables 712. The sensitivity thresholds 710 may vary as a function of time. Such variation may occur slowly, for example, over a period of months or even years. Variables 712 that exceed one of the sensitivity thresholds 710 corresponding to a current sensitivity for at least the first individual, such as variable B 712-2 and sensitivity threshold 710-2, may trigger a migraine attack. Alternatively, combinations of variables 712, such as variable C 712-3 and variable F 712-6, may exceed a sensitivity threshold 710-3 and trigger a migraine. The combinations may be cumulative, may correspond to variables 712 that occur in close temporal proximity, may correspond to respective temporal sequences of variables 712, and/or may correspond to respective ordered temporal sequences of variables 712 during at least a portion of the data-collection time interval. While embodiment 700 illustrates seven variables 712, in some embodiments there may be fewer or more variables 712.

Other intricacies associated with migraines are so-called rebound and recurrence headaches. While analgesics are designed to relieve pain, if such pharmacological agents (both prescription and nonprescription) are overused (repetitive and chronic use), they can actually cause headaches. This is known as analgesic rebound headache (ARH) or "rebound headache." Headache sufferers taking analgesic medications every day, or even as infrequently as two times a week, may find that they must take ever-increasing dosages to achieve relief. With continued overuse the medication becomes less and less effective, with pain-free periods between headaches becoming shorter and shorter. The result can be a self-sustaining cycle of increasing pain and medication.

Recurrences headaches are associated with headaches returning after a pain-free period following treatment with one or more medicines. In essence, the migraine attack "outlasts" the treatment, so the headache returns when the medication wears off. Recurrence is commonly seen following treatment with a triptan. For example, a headache resolves within one to two hours after taking a triptan, only to return full blown (i.e., with full severity) within 24 hours. In some embodiments, a recurrence headache may be defined as any headache occurring after a headache-free state at 2 hours and within 12 hours after intake of an acute pharmacological agent. In some embodiments, a recurrence headache may be defined as any headache occurring after a headache-free state at 2 hours and within 24 hours after intake of an acute pharmacological agent. A recurrence headache may have different characteristics of intensity, severity and/or associated features than an original headache episode during a migraine attack. In some cases, a recurrence headache may be of migraine or tension-type. (Some characteristics of tension headaches are summarized in Table III.)

TABLE III

Some characteristics of tension headaches.

A. At least 2 of the following 4 headache features:
   1. Bilateral location;
   2. Pressing/tightening quality,
   3. Mild or moderate intensity;
   4. Not aggravated by routine physical activity.
B. Both of the following:
   1. No nausea or vomiting
   2. Not more than one of light or sound sensitivity.
C. Duration lasting from 30 minutes to 7 days.

In the context of the disclosed embodiments, the one or more events may be one or more migraines, and the one or more temporal onsets corresponding to the one or more events may be a respective onset time and/or a respective onset time interval for one or more migraines. Onset times for migraines may be determined in accordance with one or more premonitory symptoms (discussed further below with reference to FIG. 8A) that may be experienced by at least the first individual during the prodrome phase of a migraine attack, one or more migraine symptoms during the aura phase of a migraine attack, one or more migraine symptoms during the headache phase of a migraine attack, and/or an onset of head pain as indicated by at least the first individual.

In some embodiments, the one or more physiological monitors 372 (FIG. 3) may, at least in part, determine one or more onset times for migraines. Since migraines impact the hypothalamus, with consequences for the endocrine system, the limbic system and the autonomic nervous system, a variety of physiological changes may be observable in one or more migraine patients. These physiological changes may include changes in a circadian rhythm, changes in one or more vital signs (such as pulse, respiration, systolic blood pressure, and/or diastolic blood pressure), hormonal changes, emotional changes, changes in a pulse pressure (defined as a difference of the systolic blood pressure and the diastolic blood pressure), changes in skin electrical or thermal conductivity (such as perspiration), and/or changes in at least one reflex arc. The physiological changes may be bilateral or unilateral. In an exemplary embodiment, the pulse pressure may increase or decrease (relative to an average pulse pressure during the normal phase) by 1%, 3%, 5% or more than 10% during the prodrome phase. In some embodiments, the one or more physiological monitors 372 (FIG. 3) may determine a presence of cutaneous allodynia or 'skin pain' (such as a sensitive or painful scalp), a condition associated with central sensitization, which is indicative of a deeply entrench migraine attack. In some embodiments, the one or more physiological monitors 372 (FIG. 3) may provide a metric of chronic disease regulation, for example, a frequency, a duration and/or a severity of migraines.

The pre-determined questions in the questionnaire, such as the questionnaire 600 (FIG. 6A), may correspond to patterns of occurrence (including presence and absence information) of the set of variables that are potential migraine triggers. The one or more association variables may correspond to one or more migraine triggers, and/or one or more probable or putative migraine triggers. The one or more association variables may be patient-specific, may occur in one or more groups of migraine patients, and/or may occur in at least a plurality of migraine patients. The one or more association variables may at least in part induce a migraine in at least the first individual if at least the first individual is exposed to one or more of the association variables. In some embodiments, the one or more association variables may at least in part induce a migraine in at least the first individual if at least the first individual is exposed to an amount of the one or more of the association variables that is greater than a pre-define value during a time interval. In some embodiments, the one or more association variables may be the dominant migraine triggers, such as those migraine triggers associated with 10%, 25%, 33%, 50%, or more of the migraine attacks, for at least the first individual.

Variables that may be migraine triggers may include weather changes, allergens, compounds containing phenols (also referred to as phenolic compounds), pollution, hormonal fluctuations (such as during the menstrual cycle, pregnancy, post partum, and/or menopause), trauma, illness, hypoglycemia, sensory stimuli (such as lights, sounds, and/or smells), physical exertion, sexual activity, motion, travel, sleep patterns (when and/or how much sleep), intense emotion, withdrawal of intense emotion, stress, withdrawal of stress, certain pharmacological agents (such as MAO inhibitors, oral contraceptives, estrogen replacement therapy, recreational drugs, and/or tobacco products), dietary patterns (when food is consumed), and/or diet (what and/or how much is consumed). Dietary migraine triggers may include alcohol (for example, wine), sugar substitutes (such as Aspartame), caffeine (including caffeine withdrawal), food additives (such as monosodium glutamate or MSG), processed meats, one or more fruits, one or more vegetables, one or more spices, one or more nuts, fermented food (such as vinegar), foods containing amounts of certain amino acids (such as tyramine) that exceed one or more quantity thresholds, foods containing amounts of nitrites and/or nitrates that exceed a first quantity threshold, foods containing amounts of sulfites that exceed a second quantity threshold, and/or foods containing amounts of tannins that exceed a third quantity threshold. For example, dietary migraine triggers may include blue cheese, oranges, carrots, vinegar and caffeine.

Attention is now directed towards application of the embodiments of the questionnaire for collecting information associated with migraines, such as variables corresponding to potential or putative migraine triggers. It should be understood, however, that the description applies to numerous applications and embodiments, including non-medical applications.

Prior to or at the beginning of the data-collection time interval, at least the first individual may answer one or more questions in the optional initial survey. In some embodiments, the questions may be based on at least the first individual's medical history. The optional initial survey may confirm that at least the first individual meets any applicable entry criteria, determine one or more questionnaire modules (discussed further below with reference to FIG. 8A) that may be relevant for at least the first individual, and collect initial information, such any pharmacological agents that at least the first individual takes on a regular basis (for example, daily). In the case of migraines, entry criteria may include determining that the disease in a respective patient, such as at least the first individual, is sufficiently well controlled that migraine attacks are not occurring too often (such as every day) or too infrequently (such as once a year) to preclude determination of one or more migraine triggers. For migraines, pharmacological agents may include one or more acute therapies and/or one or more preventive therapies. The pharmacological agents may include other medicines (prescription and/or non-prescription), vitamins, herbs, supplements, and/or recreational drugs that at least the first individual takes on a regular basis. The initial information may include quantities and/or times when one or more of the pharmacological agents are used. As discussed further below with reference to FIG. 19, in some embodiments a biological sample from at least the first individual may be analyzed prior to or at the beginning of the data-collection time interval. Furthermore, in some embodiments a psychological profile is determined during the initial survey.

Figure 8A:
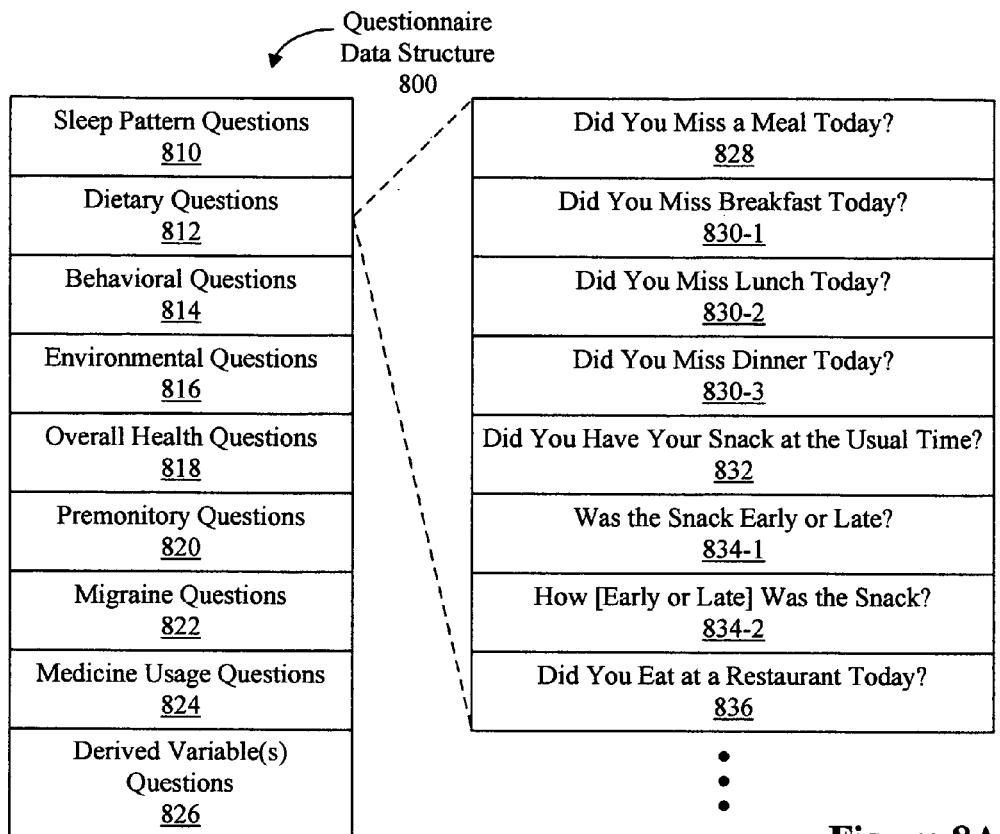
FIG. 8A is a block diagram illustrating an embodiment of a questionnaire data structure.

As noted above, pre-determined-questions in the questionnaire may be grouped into questionnaire modules. FIG. 8A is a block diagram illustrating an embodiment of a questionnaire data structure 800 including multiple pre-determined questions (such as the pre-determined questions 354 in FIG. 3) that are arranged in multiple questionnaire modules (such as the questionnaire modules 356 in FIG. 3). A corresponding questionnaire data structure is discussed below with reference to FIG. 22. The questionnaire data structure 800 may include sleep pattern questions 810 (including questions related to sleep apnea and/or insomnia), dietary questions 812 (such as dietary patterns and diet), behavioral questions 814 (such as hormonal fluctuations, physical exertion, sexual activity, motion, travel, exposure to intense emotion, withdrawal of intense emotion, exposure to stress, withdrawal of stress, and/or a use of tobacco products), environmental questions 816 (such as exposure to sensory stimuli, exposure to compounds containing phenols, and/or exposure to weather conditions such as strong wind), overall health questions 818 (such as pregnancy, a presence of trauma, illness, depression, and/or hypoglycemia), premonitory questions 820, migraine questions 822, medicine usage questions 824 (such as preventive therapies, vitamins, herbs, oral contraceptives, estrogen replacement therapy, recreational drugs, and/or pharmacological agents, including analgesics, other than migraine-specific drugs such as triptans), and/or derived variable(s) questions 826.

The premonitory questions 820 include symptoms that may be experienced and/or exhibited by at least the first individual during the prodrome phase of a migraine attack. Premonitory symptoms may include excitatory symptoms, inhibitory symptoms and/or localized pain (for example, in the head, neck and/or shoulders). Excitatory symptoms may include cravings (such as hunger and/or thirst), increased activity, sweating, a sense of well being, emotional changes (such as irritability), increased urination or bowel movements, and/or increased sensitivity to sensory stimuli. Inhibitory symptoms may include confusion, difficulty concentrating, depression, dizziness, fatigue, constricted circulation, yawning, and/or a lack of appetite.

The migraine questions 822 may include migraine occurrence information, migraine information (such as pain location, severity, quality or description, patterns, and/or temporal variation), use of medicines (including pharmacological agents such as one or more acute therapies), use of non-pharmacological treatments, a presence of visual disturbances, symptoms of cutaneous allodynia, and/or other migraines symptoms (such as nausea and/or vomiting). The migraine occurrence information may include one or more temporal onsets or onset times.

In some embodiments, at least the first individual may be asked the derived variable(s) questions 826. One or more answers to the derived variable(s) questions 826 may be determined in accordance with one or more answers to one or more pre-determined questions in one of the other questionnaire modules. For example, exposure to a food containing tyramine may be determined based on one or more answers to one or more pre-determined questions in the dietary questions module 812. One or more answers to the derived variable(s) questions 826 may be determined in accordance with a mapping operation performed on one or more answers to one or more pre-determined questions in the dietary questions module 812. For example, one or more foods consumed (such as mayonnaise) may be mapped to basic constituents (egg, vinegar, and/or mustard) and/or elemental constituents (minerals, fats, carbohydrates, and proteins).

As discussed below with reference to FIG. 20, the mapping may also be performed in the reverse direction (i.e., from one or more constituents to compound foods that contain these constituents), with a corresponding impact on the pattern(s) of occurrence. For example, a post-mapping pattern of occurrence for egg may include the pre-mapping pattern of occurrence for egg plus the post-mapping pattern of occurrence for mayonnaise, plus patterns of occurrence for other foods that include egg. For categorical data, entries in a respective post-mapping pattern of occurrence may be determined by performing a logical operation, such as an OR operation, on the corresponding entries in the patterns of occurrence that are combined to produce the respective post-mapping pattern of occurrence.

These mapping operations may be performed using tables of related information, such as one or more recipes and/or elemental constituent information. Elemental constituent information for some foods may be obtained in the National Nutrient Database on the United States Department of Agriculture's website at www.nal.usda.gov/fnic/foodcomp/Data.

One or more answers to the derived variable(s) questions 826 may also be determined in accordance with additional public information, such as weather (conditions and/or changes), altitude, allergen, and/or pollution information. For example, pollution information may be obtained from the United States Environmental Protection Agency's website at www.epa.gov/air/data. In some embodiments, one or more answers to the derived variable(s) questions 826 may be determined in accordance with at least the first individual's location(s) during the data-collection time interval, which may be provided or determined using the optional location module 370 (FIG. 3).

The pre-determined questions in one or more of the questionnaire modules may correspond to deviations from normal or usual behavior for at least the first individual. For example, deviations from normal sleep patterns for at least the first individual, deviations from normal behavior while at least the first individual is awake, and/or deviations from normal dietary behavior for at least the first individual.

In some embodiments, a respective questionnaire module, such as the dietary questions 812, may include primary questions, such as the primary questions 610 (FIG. 6A), and secondary questions, such as the secondary questions 620 (FIG. 6A). For example, the dietary questions 812 may include are primary questions such as pre-determined questions 828 ("Did you miss a meal today?"), 832 ("Did you have your snack at the usual time?") and 836 ("Did you eat at a restaurant today?"). Pre-determined question 830-1 (Did you miss breakfast today?"), pre-determined question 830-2 ("Did you miss lunch today?"), pre-determined questions 830-3 ("Did you miss dinner today?"), pre-determined question 834-1 ("Was the snack early or late?") and pre-determined question 834-2 ("How [Early or Late] was the snack?") may be secondary questions. Note that pre-determined (secondary) question 834-2 may depend on the answer to pre-determined (secondary) question 834-1.

At least some of the dietary questions 812 may be displayed using a format such as that illustrated in FIG. 6A. Other questions in one or more other questionnaire modules may be displayed using a format such as that illustrated in FIG. 6B. For example, medicine usage questions 824 and/or the use of medicines pre-determined questions in the migraine questions 822 may be displayed using the format in FIG. 6B. Pre-selected answers 616 (FIG. 6A) for some of the pre-determined questions may correspond to a usual or a normal behavior for at least the first individual in accordance with at least the first individual's answer history 360 (FIG. 3), the answer history 360 (FIG. 3) for one or more groups (such as men, women, an age group, a demographic group, groups of migraine patients, and/or groups of migraine patients having one or more migraine triggers in common), one or more answers to the optional initial survey, and/or one or more default answers 362 (FIG. 3).

Answers, be they pre-selected or not, to the pre-determined questions in the dietary questions 812, as well as in one or more other questionnaire modules, may be categorical, ordered categorical, and/or quantitative. For example, the answer to pre-determined question 828 may be 'yes' or 'no'. The answer to pre-determined (secondary) question 834-2 may be quantitative (a time in hours, minutes and/or seconds) and/or ordered categorical (between 0-1 hours, between 1-2 hours, etc.). Ordered categorical answers to some of the primary or secondary questions may include time intervals that correspond to a fraction of a day. In an exemplary embodiment, a presence or absence of a respective variable may be determined in accordance with a selection of a 'yes' answer to a primary question and a selection of one or more time intervals that correspond to a fraction of a day in answer to a related secondary question. The time intervals may include night, morning, afternoon and evening, where night is between 12 am and 5.59 am, morning is between 6 am and 11.59 am, afternoon is between 12 pm and 5.59 pm and evening is between 6 pm and 11.59 pm. In some embodiments, at least some questions in one or more of the questionnaire modules may have different ordered categorical time intervals associated with them than other questions in the one or more of the questionnaire modules.

The questionnaire data structure 800 may include fewer or additional questionnaire modules. One or more of the questionnaire modules may include one or more questions corresponding to feedback from at least the first individual and/or suggestions for additional variables to be tracked (information to be collected) and/or analyzed. Such feedback may allow a knowledge base to grow and improve as the approach is scaled to more individuals. Two or more questionnaire modules may be combined. Some pre-determined questions may be included in more than one questionnaire modules. One or more questionnaire modules may include fewer or more pre-determined questions. In some embodiments, one or more pre-determined questions may be moved from one questionnaire module to another.

As noted previously, the subset of pre-determined questions may be varied during the data-collection time interval, i.e., the questionnaire may be used dynamically. The varying may be in accordance with the configuration instructions 420 (FIG. 4), with providing of one or more pre-determined questions 354 in FIGS. 3 and 4 (for example, in a data stream that is transmitted and stored in the memory device 324 in FIG. 3), with providing of instructions corresponding to one or more pre-determined questions (such as in instructions corresponding to one or more web pages 412 in FIG. 4), and/or with providing of the optional memory device 524 in FIG. 5 containing one or more pre-determined questions 354.

In some embodiments, an initial phase of the data-collection time interval may, at least in part, correspond to a training phase, for at least the first individual (i.e., how to answer the pre-determined questions), for one or more of the apparatuses, and/or for one or more algorithms or techniques for implementing the questionnaire (for example, how best to determine the one or more temporal onsets for at least the first individual). During the training phase, the subset of pre-determined may initially include one or more pre-determined questions selected from the premonitory questions 820, the migraine questions 822 and/or the medicine usage questions 824.

The questionnaire, and the related statistical analysis (described below with reference to FIGS. 9-14), may be applied iteratively. For example, pre-determined questions in one or more of the questionnaire modules may be tree-based or hierarchical, ranging from general or broad in scope to narrow or specific in scope. General pre-determined questions may be asked one or more times during the data-collection time interval. Based on one or more answers to these general pre-determined questions, additional narrow pre-determined questions may be asked one or more times. In some embodiments, the subset of pre-determined questions may be asked, one or more association variables (for example, migraine triggers) may be identified and at least the first individual may exclude one or more of the identified association variables (for example, by modifying behavior, changing diet, etc.). This process of asking, identifying and excluding may be repeated one or more times until diminishing returns (for example, it may become difficult to readily and/or reliably identify one or more additional association variables).

Figure 8B:
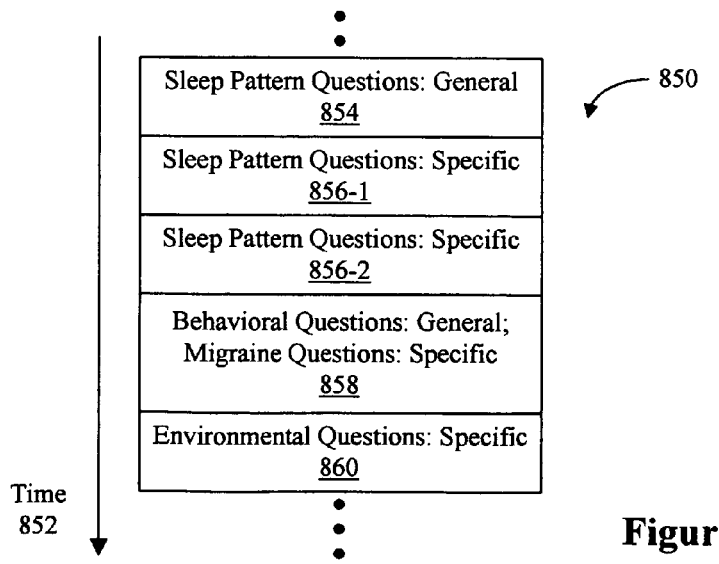
FIG. 8B is a block diagram illustrating an embodiment of a questionnaire.

FIG. 8B is a block diagram illustrating an embodiment of a questionnaire 850 that is dynamic and hierarchical. One or more pre-determined questions in question modules are included in the subset of predetermined questions as a function of time 852. General sleep pattern questions 854 may be included. Specific sleep pattern questions 856 may be included on two occasions. General behavioral questions and specific migraine questions 858 may be included. Specific environmental questions 860 may be included. The questionnaire 850 is meant to be illustrative of a dynamic questionnaire and is not indicative of a specific implementation. Thus, there may additional or fewer portions of question modules, additional or fewer question modules, an order or two or more of the question modules may be changed, at least a portion of two or more the question modules may be combined, and/or at least a portion of one or more additional question modules may be included at any instance in time.

In order to reduce or eliminate inaccuracies associated with memory or recall errors, in some embodiments at least the first individual may not be allowed to answer or modify answers in one or more subsets of pre-determined questions, such as those in the questionnaire 850, that were asked at previous instances in time that are greater than a pre-determined value, for example, one or more days prior to the current questionnaire.

Figure 9A:
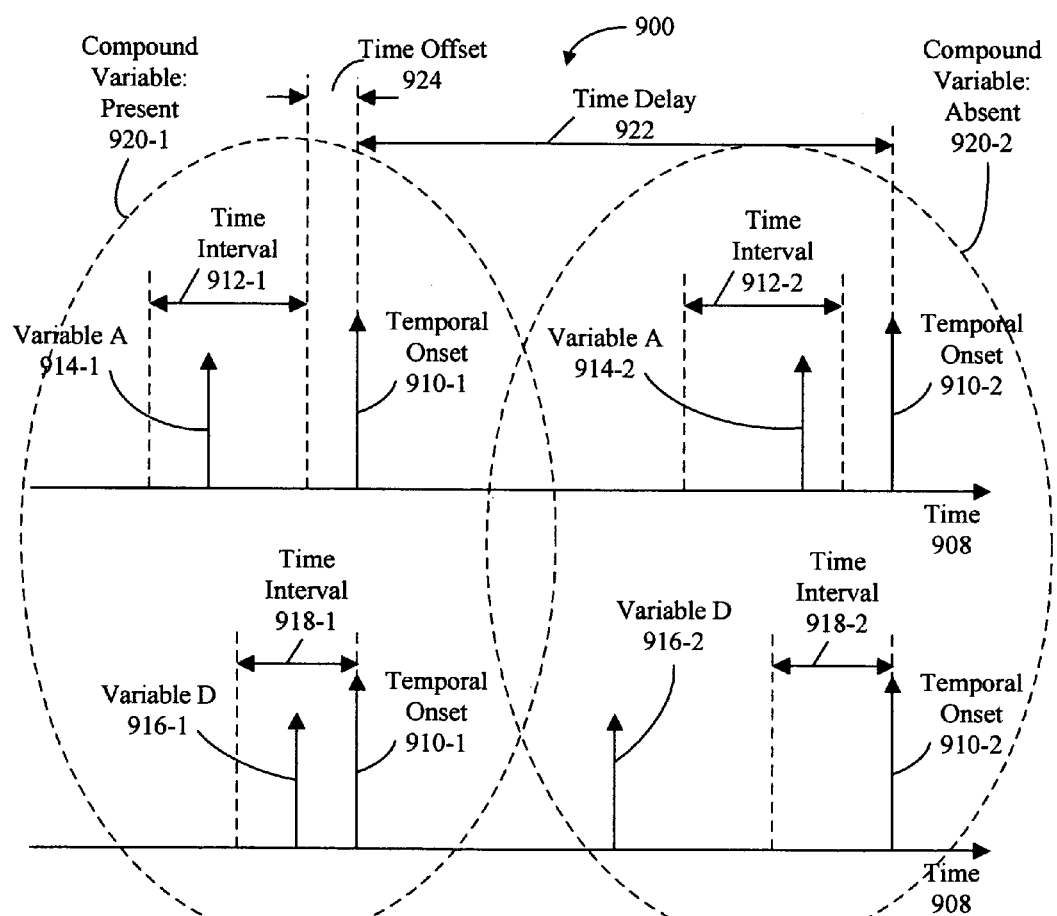
FIG. 9A is a block diagram illustrating an embodiment of determining a compound variable associated with events having different temporal onsets.

Attention is now directed towards embodiments of the statistical analysis, including the determination of one or more statistical relationships between one or more temporal onsets and one or more variables and/or one or more compound variables, and the identification of one or more association variables. The statistical analysis may include classification and/or regression (such as determining a model of the temporal onsets including one or more variables and/or one or more compound variables with corresponding weights). FIG. 9A is a block diagram illustrating an embodiment 900 of determining a compound variable 920 associated with events having different temporal onsets 910. In some embodiments, the events may be migraine attacks and the temporal onsets 910 may be onset times for migraine attacks. Temporal onsets 910 are shown as a function of time 908. The temporal onsets 910 may include one or more onset times and/or one or more onsets during one or more time windows or time intervals. There is a time delay 922 between temporal onset 910-1 and temporal onset 910-2. An inverse of the time delay 922 may correspond to a frequency of the events. Patterns of occurrence of variable A 914 and variable D 916, including instances or entries corresponding to presence information (illustrated by arrows) and corresponding to absence information (illustrated by absences of arrows), as function of time 908 are illustrated on separate but identical axes for clarity.

The compound variable 920 may correspond to at least a pattern of occurrence of variable A 914 during a first time interval 912 preceding the temporal onsets 910 and a pattern of occurrence of variable D 916 during a second time interval 918 preceding the temporal onsets 910. Note that in embodiment 900, the first time interval 912 may be offset 924 from the temporal onsets 910. In some embodiments, the first time interval 912, the second time interval 918, and/or additional time intervals corresponding to additional variables may have corresponding offsets from the temporal onsets 910. In some embodiments, a pattern of occurrence of at least one variable may be in accordance with one or more time intervals having a width that corresponds to a precision of a time measurement, i.e., the one or more time stamps that correspond to respective times.

In some embodiments, the first time interval 912, the second time interval 918, and/or other time intervals may have the same duration and/or offsets 924. In some embodiments, the first time interval 912, the second time interval 918, and/or other time intervals may have a different duration and/or offsets 924. In some embodiments, one or more of the time intervals may be adjustable. In exemplary embodiments, the time intervals may have a duration of a fraction of a day (such as 1, 2, 3, 4, 6, 12, and/or 18 hours), one day, two days, three days, more days, and/or combinations of these items. In some embodiments, offsets, such as offset 924, may be between 0 and up to 3, 5, and/or 10 or more days. In exemplary embodiments, the offset 924 may be a fraction of a day (such as 1, 2, 3, 4, 6, 12, and/or 18 hours), one day, two days, three days, more days, and/or combinations of these items.

A respective instance or entry for the compound variable 920, such as compound variable 920-1, may correspond to a presence if variable A is present during the first time interval 912-1 (a presence entry in the pattern of occurrence of variable A 914) and/or if variable D is present during the second time interval 918-1 (a presence entry in the pattern of occurrence of variable D 916). Alternatively, a respective instance or entry for the compound variable 920, such as compound variable 920-2, may correspond to an absence if variable A is absent during a first time interval 912-2 (an absence entry in the pattern of occurrence of variable A 914) and/or if variable D is absent during a second time interval 918-2 (an absence entry in the pattern of occurrence of variable D 916).

In an exemplary embodiment, entries for the pattern of occurrence of variable A 914 during the first time interval 912 and the pattern of occurrence of variable D 916 during the second time interval 918 may be categorical or may be converted from quantitative to categorical by partitioning using one or more thresholds. In some embodiments, different thresholds may be used for different variables. In some embodiments, one or more compound variables may be a weighted summation of one or more variables. The resulting one or more compound variables may be converted into categorical data using one or more thresholds and/or one or more quantitative variables may be converted into categorical data using one or more thresholds prior to generating one or more compound variables using a weighted summation.

Note that entries in the patterns of occurrence for categorical variables are typically represented by codes. For categorical variables having two classes or categories, a single binary digit may be used, such as 0 or 1, or −1 or 1. When there are more than two categories, such as with ordered categorical variables, a dummy variable having K values or bits may be used. In addition, in some embodiments an additional digit or symbol is used to indicate missing data (such as when at least the first individual fails to complete a questionnaire on one or more occasions). Entries for the compound variable 920 may determined by performing an operation and/or a logical operation on corresponding entries in the pattern of occurrence of the variable A 914 and the pattern of occurrence of the variable D 916. The operation may include multiplication. The logical operation may include a Boolean operation, such as AND. A wide variety of coding approaches, however, may be used in different embodiments for representing presence and absence information in the pattern of occurrence of variable A 914 and the pattern of occurrence of variable D 916. Therefore, in some embodiments the logical operation may include AND, OR, NOT, XOR, as well as combinations of these operations. Note that in those embodiments where the compound variable 920 includes cross-terms that correspond to the pattern of occurrence of the variable A 914 and the pattern of occurrence of the variable D 916 the resulting analysis includes nonlinear terms.

While FIG. 9A illustrates two variables, in some embodiments one, three or more variables may be used to determine the pattern of occurrence (including presence and absence information) for the compound variable 920. While a respective variable has a corresponding time interval and offset (which may be zero or finite), in some embodiments at least two variables may have time intervals having the same duration and/or the same offset. Similarly, while FIG. 9A illustrates two temporal onsets 910, in some embodiments there may be one temporal onset 910 or three or more temporal onsets 910, which may be used in determining the pattern of occurrence of the compound variable 920.

Figure 9B:
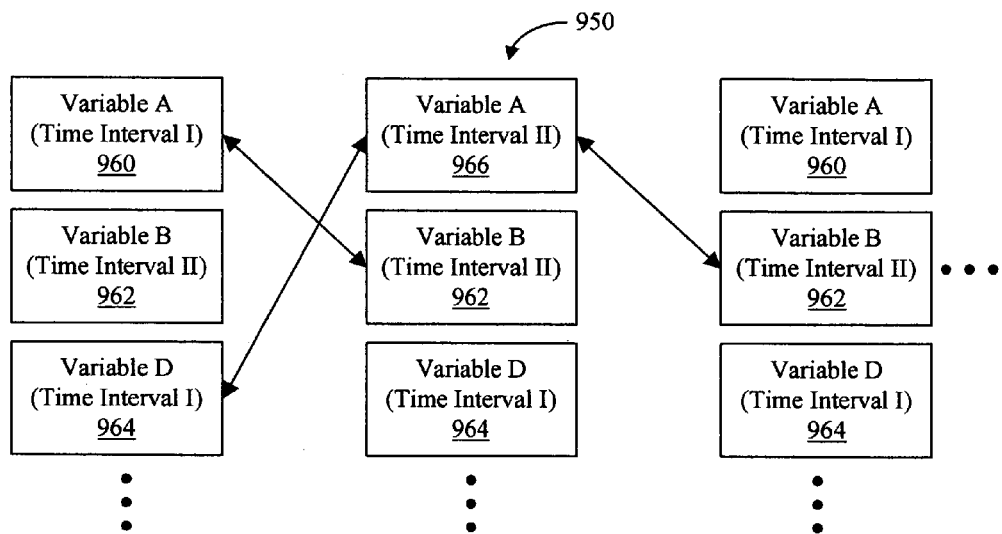
FIG. 9B is a block diagram illustrating an embodiment of determining compound variables.

FIG. 9B is a block diagram illustrating an embodiment 950 that summarizes the determining of compound variables. Logical operations are performed on the patterns of occurrence of one or more subsets of variables, such as variable A (during time interval I) 960 and variable B (during time interval II) 962, and variable D (during time interval I) 964, variable A (during time interval II) 966 and variable B (during time interval II) 962.

A number of variables included in determining a respective compound variable is henceforth referred to as an order n. FIG. 9B illustrates determination of a compound variable of order 2 and a compound variable of order 3. In some embodiments, a respective variable during a time interval, such as variable D (during time interval I) 964, may be included once in determining a respective compound variable, i.e., multiple instances of the respective variable during the time interval may not be included in determining the respective compound variable. However, the respective variable may be included more than once in determining the respective compound variable if different time intervals are used, such as variable A (during time interval I) 960 and variable A (during time interval II) 966. In some embodiments, there may be additional or fewer variables, i.e., the order may be 1 (a respective compound variable is merely a variable) or 4 or more. In some embodiments, time interval I may correspond to a duration of 24 hours with an offset 924 (FIG. 9A) of 0, 24 or 48, 72 and/or 96 hours from the temporal onsets 910 (FIG. 9A). Time interval II may correspond to a duration of 24 hours with an offset 924 (FIG. 9A) of 0, 24 or 48, 72 and/or 96 hours from the temporal offsets 910 (FIG. 9A). In some embodiments, there may be additional or fewer variables included in a respective compound variable, there may be fewer or additional time intervals, and/or there may be fewer or additional offsets.

Referring back to FIG. 9A, as discussed further below one or more statistical relationships between the patterns of occurrence of one or more compound variable, such as compound variable 920, and/or the pattern of occurrence of one or more of the variables, such as variable A 914, and the temporal onsets 910 may be determined. In the case of migraines, however, one or more temporal onsets 910 corresponding to one or more rebound headaches, one or more recurrence headaches, and/or one or more tension headaches may be excluded during the determining of the one or more statistical relationships. In some embodiments, one or more temporal onsets 910 may be excluded if there is missing data in one of the time intervals 912 and/or 918. For example, the first individual may not have logged data on one or more days during the data-collection time interval.

Excluding some of the temporal onsets 910 may improve the results of the statistical analysis. For example, the one or more rebound headaches may be identified in accordance with a medicine usage history for pharmacological agents, such as analgesics and/or triptans. In some embodiments, the one or more rebound headaches may be identified, at least in part, if there is no pain-free period between migraines attacks. In some embodiments, a subset of the temporal onsets 910 may be used in the calculations to increase a magnitude of the determined statistical relationship.

Figure 10:
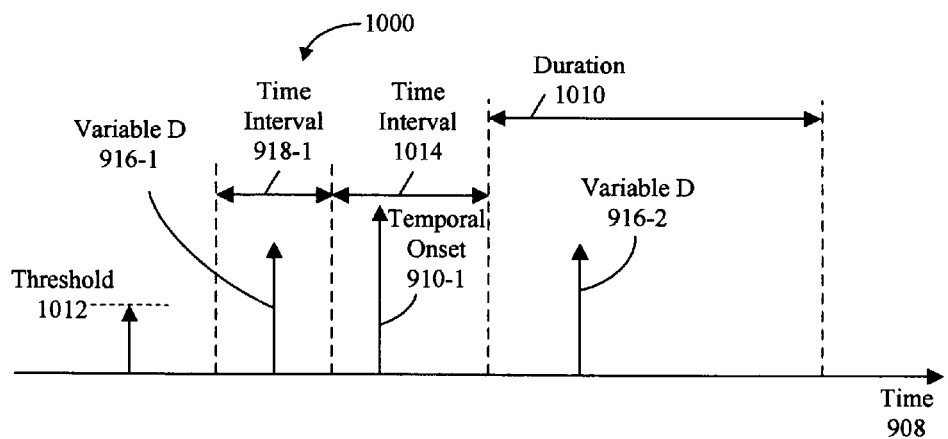
FIG. 10 is a block diagram illustrating an embodiment of a variable occurring during a duration of an event.

In addition, entries in the pattern of occurrence of one or more variables that occur during the duration of an event, such as a migraine, may be excluded in determining one or more compound variables and/or one or more statistical relationships. The reason for this exclusion operation may be that such entries, corresponding to the presence of one or more variables, may not trigger an event since an event is already occurring. Said differently, it may not be possible to initiate something that is already occurring. FIG. 10 is a block diagram illustrating an embodiment 1000 with a variable D 916-2 occurring during a duration 1010 of a migraine. As a consequence, the presence of variable D 916-2 may be excluded from the determining of compound variable 920 (FIG. 9A) and/or one or more statistical relationships, such as those between temporal onsets 910 and the pattern of occurrence of the compound variable 920 (FIG. 9A) and/or between temporal onsets 910 and the pattern of occurrence of variable D 916. Note that the temporal onset 910-1 is illustrated as occurring during a time interval 1014. In some embodiments, the temporal onset 910-1 corresponds to an onset time (i.e., a specific time). In alternate embodiments, the duration 1010 may be defined with respect to a beginning of the time interval 1014, a center of the time interval 1014, or the onset time corresponding to the temporal onset 910-1. Embodiment 1000 also illustrates a threshold 1012 that may be used to convert a quantitative variable into a categorical variable by partitioning. In other embodiments, one or more thresholds may include one or more geographic directions.

While embodiments 900 (FIG. 9A) and 1000 illustrate variables, such as the variable D 916, occurring in time intervals 912 (FIG. 9A) and 918 (FIG. 9A) preceding corresponding temporal onsets 910, in some embodiments occurrences of one or more variables and one or more temporal onsets 910 in one or more time intervals may be included when determining one or more of the statistical relationships. While the embodiment 1000 illustrates the exclusion of the presence of variable D 916-2, in some embodiments entries corresponding to an absence of one or more variables may be excluded from the determination of one or more statistical relationships. This may be separate from and/or in addition to the exclusion of the presence of the one or more variables.

A wide variety of computational techniques may be used to determine the one or more statistical relationships, including one or more parametric analysis techniques, one or more non-parametric analysis techniques, one or more supervised learning techniques and/or one or more unsupervised learning techniques. In some embodiments, one or more non-parametric analysis techniques may be used. As noted previously, non-parametric analysis techniques make few assumptions about an existence of a probability distribution function, such as a normal distribution, corresponding to a population from which samples or entries are obtained, or regarding independence of the variables and/or the compound variables. In general, non-parametric analysis techniques may use rank or naturally occurring frequency information in the data to draw conclusions about the differences between populations.

The one or more non-parametric analysis techniques may perform hypothesis testing, i.e., to test a statistical significance of a hypothesis. In particular, the one or more non-parametric analysis techniques may determine if the one or more temporal onsets and the one or more compound variables and/or one or more variables are statistically independent (or dependent) in accordance with a statistical significance criterion. One or more variables and/or one or more compound variables having a statistically significant relationship with the temporal onsets may be used to identify one or more association variables. In the case of migraines, the one or more association variables may be migraine triggers or potential migraine triggers.

In exemplary embodiments, the non-parametric analysis technique may include a chi-square analysis technique, a log-likelihood ratio analysis technique (also referred to as G-test), and/or a Fisher's exact probability analysis technique. In addition to their other advantages, these techniques may be well suited to analyzing an underdetermined problem (i.e., sparse sampling in a multi-dimensional variable space), in which there may be a plurality of variables and/or compound variables and a limited number of entries or samples.

The chi-square analysis technique, the log-likelihood ratio analysis technique, and the Fisher's exact probability analysis technique may be determined using a cross-tabulation or contingency tables (sometimes referred to as bivariate tables). The Fisher's exact probability analysis technique computes the sum of conditional probabilities of obtaining the observed frequencies in a respective contingency table and the conditional probabilities of obtaining exactly the same observed frequencies for any configuration that is more extreme (i.e., having a smaller conditional probability). The chi-square ($\chi^2$) may be determined using $$\chi^2 = \sum_i \frac{(O_i - E_i)^2}{E_i},$$

and the log-likelihood ratio (LLR) using $$LLR = \sum_i O_i \ln\left(\frac{O_i}{E_i}\right),$$

where the summation is over the entries in the respective contingency table, $O_i$ is the i-th observed frequency value, and $E_i$ is the i-th expected frequency value. The LLR tests the likelihood of one hypothesis (the alternate hypothesis) against another, more restrictive hypothesis (the null hypothesis). In an exemplary embodiment, the alternate hypothesis is that the conditional probabilities are different from 0.5 and the null hypothesis is that the conditional probabilities are 0.5. The following example illustrates an embodiment of determining a statistical relationship using the log-likelihood ratio.

Consider the data in Table IV. The first column contains the number of entries in the pattern of occurrence where a variable or compound variable is present during a time interval, such as the first time interval 912 (FIG. 9A), and a temporal onset is present after a time offset, such as the time offset 924 (FIG. 9A) (henceforth denoted by $X_{11}$) plus the number of entries in the pattern or occurrence where the variable or compound variable is absent during the time interval and a temporal onset is absent after the time offset (henceforth denoted by $X_{00}$). $X_{11}$ is sometimes referred to as a true-true and $X_{00}$ is sometimes referred to as a false-false. $X_{11}$ and $X_{00}$ are henceforth referred to as co-occurrences.

The second column contains the number of entries in the pattern of occurrence where the variable or compound variable is present during the time interval and a temporal onset is absent after the time offset (henceforth denoted by $X_{10}$) plus the number of entries in the pattern of occurrence where the variable or compound variable is absent during the time interval and a temporal onset is present after the time offset (henceforth denoted by $X_{01}$). $X_{10}$ is sometimes referred to as a true-false and $X_{01}$ is sometimes referred to as a false-true. $X_{10}$ and $X_{01}$ are henceforth referred to as cross occurrences.

TABLE IV

An embodiment of a contingency table.

| Number of Co-Occurrences ($X_{11} + X_{00}$) | Number of Cross Occurrences ($X_{10} + X_{01}$) |
|---|---|
| 46 | 11 |

If the variable or the compound variable and the temporal onsets are completely independent, the expected frequency values for each column, $E_1$ and $E_2$, would equal 28.5, one half of the conditional probability times the sum of the number of co-occurrences and cross-occurrences, i.e., the total number of observations (data points or samples) in Table IV. Therefore, for Table IV $$LLR = 2 \cdot 46 \ln\left(\frac{46}{28.5}\right) + 2 \cdot 11 \ln\left(\frac{11}{28.5}\right) = 44.04 - 20.94 = 23.10.$$

A one-sided minimal statistical significance confidence criterion of 5% ($\alpha$=0.05) or statistical confidence threshold, based on the 1 degree of freedom in this example, corresponds to an LLR of 3.841. Since the LLR for Table IV is greater than 3.841, the LLR, and thus the alternate hypothesis, is statistically significant. From a statistical significance perspective, therefore, the temporal onsets and the pattern of occurrence of the variable or compound variable in this example are dependent. Note that the determination of the statistical relationship for the temporal onsets and the variable or the compound variable in this embodiment uses presence and absence information in the pattern of occurrence of the variable or compound variable. In some embodiments, one or more of the statistical relationships may be determined using presence information, i.e., the presence of one or more variables or one or more compound variables during one or more time intervals, without using absence information. In some embodiments, a statistically significant LLR also has a number of co-occurrences greater than a number of cross-occurrences (i.e., it is related to migraines). And in some embodiments, a statistically significant LLR also has a number of cross-occurrences greater than a number of co-occurrences (i.e., it is anti-related to migraines). In this way, migraine variables and/or anti-migraine variables may be identified. In alternate embodiments, a wide variety of analysis techniques may be used to determine the one or more statistical relationships, including one or more non-parametric analysis techniques and one or more parametric analysis techniques.

In parametric analysis, a Pearson's product-moment correlation coefficient r may be useful in summarizing a statistical relationship. For some contingency tables, Cramer's phi $\varphi$, the square root of $\chi^2$ or the LLR divided by the number of observations N, may have a similar interpretation to r (although, it is known that Cramer's phi $\varphi$ may underestimate r). In the example illustrated in Table IV, $$\varphi = \sqrt{\frac{LLR}{N}} = \sqrt{\frac{23.1}{57}} = 0.64.$$

The chi-square analysis technique and the log-likelihood ratio analysis technique may have a maximal sensitivity for contingency tables based on patterns of occurrence of variables or compound variables having 50% presence entries and 50% absence entries. In addition, in embodiments where temporal onsets, such as temporal onsets 910 (FIG. 9A), correspond to onsets during one or more time windows or time intervals, maximal sensitivity may occur if 50% of these time windows or time intervals have a temporal onset (i.e., a presence entry). In some embodiments, one or more contingency tables may be generated to achieve approximately 50% presence entries for patterns of occurrence of one or more variables or one or more compound variables, and/or 50% temporal onsets by using a subset of the collected information or data. In an exemplary embodiment, one or more contingency tables may be generated by approximately randomly (including the use of a pseudo-random number generator or algorithm) selecting a subset of the temporal onsets, and/or approximately randomly selecting a subset of the presence or absence entries of one or more patterns of occurrence of one or more variables or one or more compound variables such that the one or more contingency tables may have approximately 50% presence entries and 50% absence entries distributed over $X_{00}$, $X_{11}$, $X_{10}$, and $X_{01}$. For infrequently occurring events, variables, and/or compound variables, there may be more absence entries than presence entries in the collected data or information. As a consequence, different sampling ratios may be used for presence and absence entries.

In some embodiments, boosting may be used when generating one or more contingency tables. The fraction of the collected information may be approximately randomly sampled to generate one or more contingency tables. A respective contingency table may be generated K times using approximate random sampling. Statistical relationships for at least M of these K contingency tables may be used (including combining and/or averaging) to determine whether or not the temporal onsets and the corresponding variable or compound variable are independent or dependent. In an exemplary embodiment, K may be 5, 10, 25, 50, 100 or more. M may be 50% (rounded to the nearest integer), 60%, 66%, 70%, 75%, 80% or more of K.

In some embodiments, there may be too few presence entries or too many presence entries in one or more patterns of occurrence of one or more variables or compound variables to reliably determine statistically significant independence (or dependence) from the temporal onsets. As a consequence one or more of these variables or one or more of these compound variables may be excluded when determining one or more statistical relationships. In an exemplary embodiment, one or more variables or one or more compound variables having patterns of occurrence with less than 10% presence entries or more than 85% presence entries may be excluded. In another exemplary embodiment, one or more variables or one or more compound variables having patterns of occurrence with less than 4 presence entries or less than 10 absence entries may be excluded. To assist in obtaining sufficient presence and absence entries, in some embodiments at least the first individual may be instructed to vary their activities and/or diet from day to day during the data collection time interval.

Figure 11:
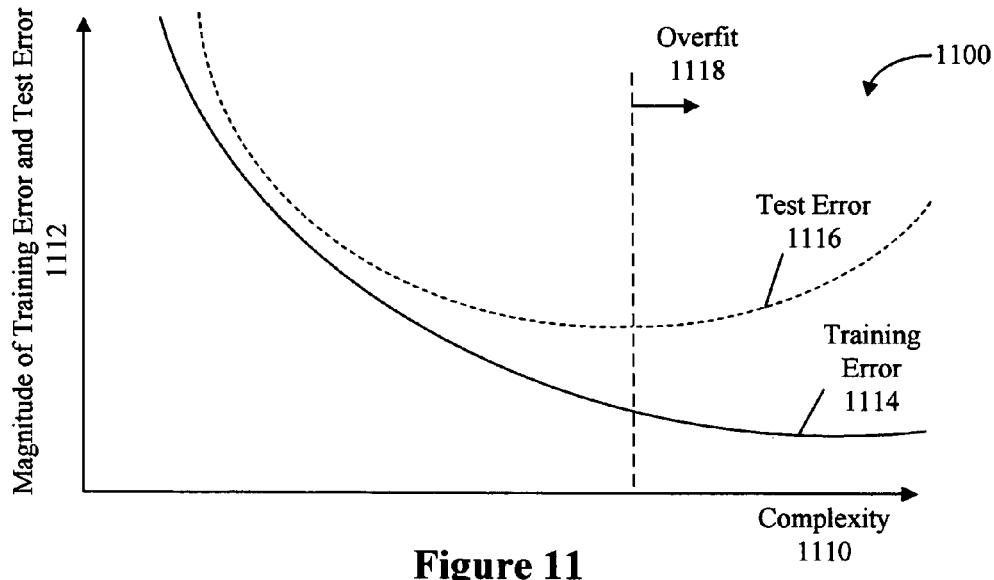
FIG. 11 is a block diagram illustrating an embodiment of determining model complexity.

Overfitting is a risk when developing a model in a statistical learning problem. In some embodiments, this risk may be addressed by using a fraction or percentage of the collected data or information (patterns of occurrence and temporal onsets) for training, i.e., to develop the model, and a remainder for testing the resulting model. This is illustrated in FIG. 11, which is a block diagram illustrating an embodiment 1100 of determining model complexity. In some embodiments, the model complexity may correspond to a number of variables or compound variables that have statistically significant dependence on the temporal onsets. In some embodiments, the model complexity may, at least in part, correspond to a number of variables included in a respective compound variable, i.e. the order n. Embodiment 1100 shows a magnitude of a training and/or a test error 1112 as a function of model complexity 1110. A training error 1114 typically decreases as the model complexity 1110 increases (the model better fits or predicts a training set of data). A test error 1116 typically exhibits a minimum. Additional model complexity 1110 beyond this point does not generalize well (the model offers a poorer fit or prediction for a test set of data). Beyond this point, therefore, the training set of data may be overfit 1118. In exemplary embodiments, the percentage of the collected information used for training may be 70%, 75%, 80%, 85% or 90%.

An additional metric of the model complexity may be determined. This metric may be used in conjunction with or independently of the training set of data and the test set of data. The additional metric is described below. In some problems and/or embodiments, determining one or more statistical relationships for one or more variables (or, said differently, one or more compound variables of order 1) may not be sufficient to determine statistically significant independence (or dependence) with respect to the temporal onsets. For example, in multi-dimensional problems, where exposure to two or more variables in at least close temporal proximity may be necessary to initiate a temporal onset (such as a migraine), a value of the Fisher's exact probability, $\chi^2$, LLR for a compound variable of order 1, and/or another metric of statistical relationship may be reduced since there is a penalty for the presence of the cross occurrences, $X_{10}$ and $X_{01}$.

More generally, the value of the Fisher's exact probability, $\chi^2$, LLR, and/or another metric of statistical relationship may be reduced if the order n of one or more compound variables is less than an intrinsic order of the multi-dimensional problem. In the case of $X_{10}$, a temporal onset may or may not occur unless a certain number of variables or a set of variables (which may be inter-operative) are present in close temporal proximity. And in the case of $X_{01}$, more than one set of variables may be present, i.e., one or more variables in another set of variables may have triggered the corresponding temporal onsets. As illustrated in FIG. 7, in the embodiments for migraines there may also be variations in a patient's sensitivity threshold to a variable or one or more sets of variables as a function of time.

To assess whether or not the model has sufficient complexity, i.e., whether or not one or more compound variables have been determined to sufficient order n, a ratio R may be determined. R is defined as $X_{11}$ divided by the total number of occurrences of the variable or compound variable of order n, i.e., $$R = \frac{X_{11}}{(X_{11} + X_{10})}.$$

An increasing value of R, and/or Cramer's phi φ, as statistical analysis is performed to higher order (i.e., n+1) may be metrics of goodness, i.e., it may indicate that the higher order does a better job determining statistically significant independence or dependence between one or more compound variables and the temporal onsets. In some embodiments, contingency tables for one or more compound variables may be generated for progressively higher orders. Once the ratio R is close to or equal to one, i.e., $X_{10}$ is close to or equal to zero, further increases in the order of one or more compound variables may not be needed, i.e., the model has sufficient complexity.

One or more variables and/or compound variables having statistically significant statistical relationships with the temporal onsets may be identified as one or more association variables. For a respective compound variable or order n having a significant statistical relationships with the temporal onsets, the n constituent variables may be identified as n association variables and/or as a set of association variables. In some embodiments, one or more statistically significant compound variables of order n having the ratio R approximately equal to 1 may be identified as one or more association variables. In the embodiments for migraines, one or more association variables may be one or more migraine triggers or one or more probable migraine triggers for at least the first individual.

In some embodiments, one or more compound variables of order n and/or one or more constituent variables in the one or more compound variables of order n may be ranked in accordance with the corresponding determined statistical relationships that are statistically significant. In some embodiments, a ranking of a respective statistically significant constituent variable and/or a respective compound variable is in accordance with a number of associated migraine onsets. In some embodiments, a ranking of a respective constituent variable is in accordance with a number of occurrences of the respective constituent variable in one or more compound variables of order n having statistical relationships that are statistically significant. Furthermore, in some embodiments one or more of the ranking techniques described above may include multiplicative weights. For example, a ranking may be in accordance with a product of the number of occurrences of the respective constituent variable times an average number of associated migraine onsets that correspond to these occurrences.

Ranking may be performed as the statistical significance confidence criterion (α) is progressively increased. A respective ranking corresponding to a respective statistical significance criterion α may be meaningful if a total number of variables and/or compound variables S used in the analysis times a number of variables and/or compound variables having statistical relationships greater than α is greater than α times S.

In exemplary embodiments, α may be 0.05 or lower. For a respective ranking, a pareto corresponding to at least a subset of the respective ranking may be defined. The pareto may correspond to variables or compound variables having a statistical relationship or a number of occurrences exceeding a threshold. In some embodiments, a top 10, 20, 50 or 100 variables or compound variables may be used, or a plurality of the top 10, 20, 50 or 100 variables or compound variables may be used. For compound variables of order n, approximate stability of the pareto as the statistical significance confidence criterion is increased may be used to identify a noise floor. Approximately stability may include an approximately unchanged order n in the ranking or a presence of approximately the same variables (for example, more than 70% of them) in the ranking. In exemplary embodiments, the noise floor may correspond to an α of 0.01 or lower, an α of 0.001 or lower, or an α of 0.0001 or lower. In some embodiments, for a respective statistical significance criterion α a noise floor in a ranking may correspond to an uncertainty in the statistical relationships for one or more variables and/or one or more compound variables that is associated with missing data during the data-collection time interval (such as data that was not logged for one or more days). One or more variables and/or one or more compound variables in paretos corresponding to one or more statistical significance confidence criteria that exceed a noise floor may be identified as association variables.

In some embodiments, a background ranking that corresponds to noise in the data may be determined. In an exemplary embodiment, the background ranking may be determined using temporal onsets that are randomly or pseudo-randomly selected. In another exemplary embodiment, the background ranking may correspond to one or more variables and/or one or more compound variables that do not have a statistic relationship with the temporal onsets (for example, an LLR of infinity). The background ranking may be subtracted from one of the previously described rankings to correct the results for a background contribution. This may be useful since in some embodiments the analysis technique described above with reference to FIGS. 9-10 is a form of nonlinear analysis (which is sometimes referred to as nonlinear feature extraction). As such, contributions corresponding to intermodulation products may occur in the statistical relationships between the temporal onsets and the one or more variables and/or the one or more compound variables. Furthermore, a ratio of a number of absence entries to a number of presence entries in the pattern of occurrence that is used in a respective contingency table may also increase the background contribution. For migraines, as this ratio is increased, the previously described rankings may increasingly correspond to a background contribution. Subtracting the background contribution may, therefore, reduce and/or eliminate such effects from the results.

In some embodiments, one or more variables and/or one or more compound variables in paretos corresponding to one or more statistical significance confidence criteria that exceed the noise floor may be used as a seed set in a subsequent statistical analysis. The subsequent statistical analysis may determine statistical relationships for compound variables of a higher order. In some embodiments, the subsequent analysis may utilize an analysis technique such as SVM or CART. These and other analysis techniques are discussed further below.

Figure 12:
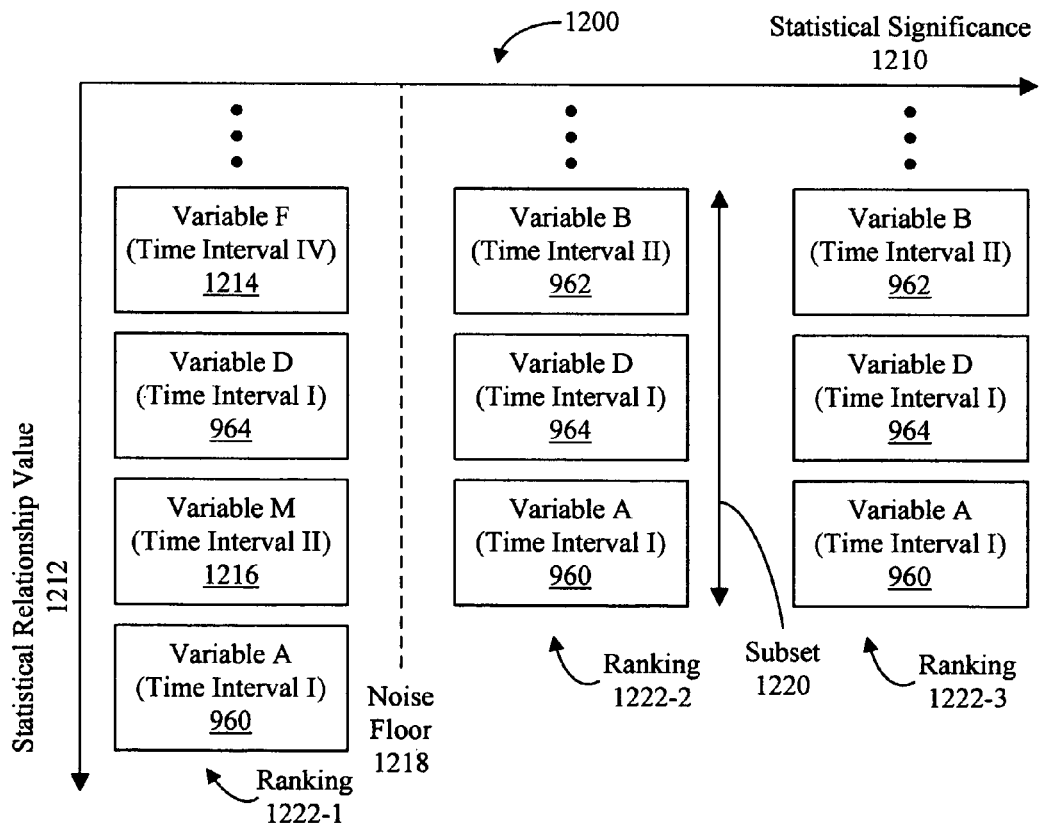
FIG. 12 is a block diagram illustrating an embodiment of ranking variables.

FIG. 12 is a block diagram illustrating an embodiment of ranking variables 1200. Statistical relationship value 1212 is plotted as a function of statistical significance 1210, such as the statistical significance confidence criteria. Several rankings 1222 are illustrated. Ranking 1222-1, including variable F (during time interval IV) 1214 and variable M (during time interval II) 1216, is below a noise floor 1218. Ranking 1222-2 and ranking 1222-3 are above the noise floor 1218. A subset 1220 of ranking 1222-2 and ranking 1222-3 is stable. The subset 1220 may identified as the pareto.

In an exemplary embodiment for migraines, the noise floor 1218 corresponds to an α of approximately 0.001. At least 8 of the top-10 variables in paretos for more stringent statistical significance confidence criteria than that corresponding to the noise floor 1218 are present even when an approximately random subset corresponding to 80% of the patterns of occurrence and the temporal onset data is used. Excluding probable recurrence headaches, rebound headaches and tension headaches increases the statistical relationship values 1212 for compound variables having an order n corresponding to the pareto. Compound variables of at least order 4 have ratio R values approximately equal to 1.

Having identified one or more association variables for at least the first individual, one or more additional association variables may be identified. For example, if one or more groups of association variables have been previously determined for one or more other individuals, the one or more association variables identified for at least the first individual may be used to associate at least the first individual with one or more of these groups. In this way, one or more of the association variables in one or more of the groups may be identified as additional association variables for at least the first individual. For example, the one or more additional association variables may be groups of migraine triggers and at least the first individual may be associated (classified) with one or more of these groups in accordance with one or more identified migraine triggers for at least the first individual.

Alternatively, additional association variables may be identified by associating the identified one or more association variables for at least the first individual with previously determined groups of variables. For example, the identified one or more association variables for at least the first individual may be foods and additional association variables may be identified by associating the foods with corresponding food groups, such as pine-apple, mushroom, melon, cashew, banana, or citrus, or groups determined based on an amount of constituent elements (minerals, fats, carbohydrates, and/or proteins) in foods. For example, if an identified association variable is in the beet family or the citrus family, other members of the beet or citrus families may be identified as association variables.

Figure 13:
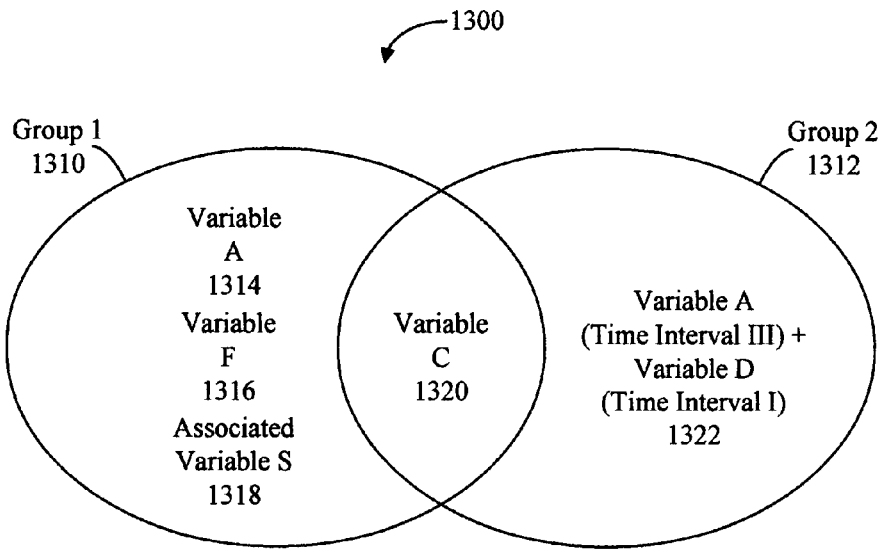
FIG. 13 is a block diagram illustrating an embodiment of associating one or more variables with one or more groups of variables.

FIG. 13 is a block diagram illustrating an embodiment 1300 of associating one or more variables with one or more groups of variables. Group I 1310 may include variable A 1314, variable F 1316, associated variable S 1318, and variable C 1320. Group II 1312 may include variable C 1320 and a compound variable 1322, including variable A (during time interval III) plus variable D (during time interval I). If a variable, such as variable A 1314, is determined or identified, one or more of the other variables in group I 1310 may be identified. In some embodiments, there may be additional groups, there may or may not be overlap (such as variable C 1320) between two or more of the groups, and/or a respective group may include fewer or more variables, fewer or more associated variables, and/or fewer or more compound variables.

Having identified one or more association variables in accordance with one or more statistical relationships, rankings, and/or associated groups of associated variables, one or more recommendations and/or one or more reports may be provided to at least the second individual and/or at least the first individual. In an exemplary embodiment, the one or more recommendations may include a listing of one or more migraine triggers and/or one or more probable migraine triggers for at least the first individual. The one or more recommendations may include one or more variables for which the statistical analysis was unable to determine a statistically significant relationship. In some embodiments, the one or more recommendations may indicate one or more migraine triggers and/or one or more probable migraine triggers that at least the first individual may wish to modify (such as for behaviors) and/or avoid. The one or more recommendations may indicate additional analysis that may be advisable in accordance with one or more of the statistical relationships and/or the one or more association variables. One or more corresponding reports may include the one or more recommendations. The one or more reports may include a summary for at least the first individual. The summary may include a health overview for at least the first individual during at least a portion of the data-collection time interval. In the case of migraines, the health overview (also referred to as a migraine diary) may include a summary of migraine frequency, migraine duration, migraine severity and/or the use of one or more pharmacological agents, such as one or more acute therapies and/or one or more preventive therapies.

In some embodiments, the one or more recommendations may include placebo information, for example, placebo migraine triggers. After this placebo information is provided to at least the first individual (possibly via an intermediary such as at least the second individual), an impact on at least the first individual may be determined. For example, migraine frequency, migraine duration, migraine severity, and/or use of pharmacological agents during a subsequent time interval may be determined. An efficacy of the identified association variables may be determined by comparing these metrics with those that occur when non-placebo information is used, i.e., when actual association variables are provided to at least the first individual. The difference of these two metrics can be used to define a therapeutic gain. In some embodiments, the therapeutic gain may be determined by averaging results for two or more individuals such as at least the first individual.

Attention is now given to other techniques of performing statistical analysis, such as determining the one or more statistical relationships. As discussed previously, one or more variables or one or more compound variables determined during the statistical analysis, for example, in one or more paretos, may be used in subsequent analysis. In some embodiments, the subsequent analysis may utilize a non-parametric analysis technique as an initial or first stage. In other embodiments, the subsequent analysis may not utilize a non-parametric analysis technique. The subsequent analysis may be used as the initial or first stage, to refine the model (including adding or removing one or more variables and/or one or more compound variables), and/or identify one or more association variables. The subsequent analysis may include classification and/or regression (such as determining a model of the temporal onsets including one or more variables and/or one or more compound variables with corresponding weights). As with the initial statistical analysis, a wide variety of techniques may be used in the subsequent analysis. Two such techniques, SVM and CART, are described further below.

Embodiments of SVM are instances of supervised learning techniques that may be applied to classification and regression problems. For binary classification, a set of binary labeled data points (training data or examples) is provided. SVMs may be used to determine an optimal separation boundary, defined by the variables and/or compound variables, between two classes of data points. A separation boundary is optimal if using it as a decision rule to classify future data points minimizes an expected classification error. For linearly separable data sets (i.e., a class of absences, which may be indicated by −1, and a class of presences, which may be indicated by +1, may be separated by a line in 2 dimensions, or a so-called hyperplane in higher dimensions), SVMs may be used to determine a maximal margin hyperplane. For the maximal margin hyperplane, a linear decision boundary may be positioned such that it separates both classes and such that the distance to the closest point from each class is maximized. For non-linearly separable data sets, some training data points may be allowed on the opposite or "wrong" side of the hyperplane, i.e., a classification error on the training data set may be allowed and may be minimized, while the margin, measured between points on the "correct" side of the hyperplane, is maximized.

If a linear decision boundary is not sufficiently complicated to model the separation between classes accurately, the corresponding linear model may be transformed into a non-linear model by non-linearly transforming the variables and/or compound variables into a possibly higher dimensional Euclidean space. A linear decision boundary constructed in such a higher dimensional Euclidean space may correspond to a non-linear decision boundary in the original space of variables and/or compound variables. This approach is referred to as kernel SVM.

Depending on how the margin and training error are measured, and how a trade-off between maximizing the margin and minimizing the training error is established, different types of SVMs may be obtained. In some embodiments, SVM may include standard 1-norm SVM (measuring the margin using Euclidean distance, i.e., a $L_2$-norm, and the training error using a $L_1$-norm), standard 2-norm SVM (measuring the margin using Euclidean distance, i.e., the $L_2$-norm, and the training error using the $L_1$-norm), and/or LP-SVM (measuring the margin using the $L_1$-norm and the training error using the $L_1$-norm). Each of these 3 types of SVM may be a C-type or $\eta$-type SVM. These two varieties correspond to different ways of trading-off maximizing the margin against minimizing the training error. The 1-norm SVM, standard 2-norm SVM, and/or LP-SVM may be a C+/C− or $\eta+/\eta-$ type (when errors on positive (+1) labeled training data are weighted differently than errors on negative (−1) labeled training data).

The principle for binary classification described above may be extended to regression, for example, by copying the regression data twice, shifting both copies in opposite directions (over a distance epsilon) with respect to the continuous output dimension or variable and establishing a regression surface as a decision boundary between the two shifted copies that may be regarded as two classes for binary classification. As a consequence, in some embodiments, regression versions of SVMs corresponding to previously described SVMs may be used.

The decision boundary determined using one or more SVMs may be used to discriminate between temporal onsets and non-temporal onsets. For binary classification, measures of goodness for the resulting model include a prediction accuracy that is better than predicting 50% of the positive data (i.e., occurrences, which may be indicated by a +1) as positive (i.e., true positive predictions) and better than predicting 50% of the negative data (i.e., absences, which may be indicated by a −1) as negative (i.e., true negative predictions). Doing better than 50/50 corresponds to doing better than random. In an exemplary embodiment, the resulting model successfully predicts at least 80-85% of the true-false ($X_{10}$) and false-false events ($X_{00}$), i.e., the true negatives, while predicting significantly more than 50% of the true positives correctly, i.e., false-true (false-true ($X_{01}$) and true-true events ($X_{11}$)).

CART is a non-parametric multivariate analysis technique. It involves the determination of a binary decision tree using the training set of data. Predictions based on the resulting tree may be compared to the test set of data (cross validation). A decision tree provides a hierarchical representation of the feature space in which explanatory variables are allocated to classes (such as temporal onsets or non-temporal onsets) according to the result obtained by following decisions made at a sequence of nodes at which branches of the tree diverge. Branches or divisions of the tree may be chosen to provide the greatest reduction in the entropy of the variables (for a classification tree based on categorical data), such as a small or zero standard deviation, or the greatest reduction in the deviation between the variables (and/or compound variables) and one or more variables being fit (for a regression tree based on quantitative data). A tree stops growing when no significant additional reduction can be obtained by division. A node that is not further sub-divided is a terminal node. It is associated with a class. A desirable decision tree is one having a relatively small number of branches, a relatively small number of intermediate nodes from which these branches diverge, terminal nodes with a non-zero number of entries, and high prediction power (correct classifications at the terminal nodes). In some embodiments, CART may be used in conjunction with a gradient boosting algorithm, where each boosted tree is combined with its mates using a weighted voting scheme. Gradient boosting may be used to force the binary decision tree to classify data that was previously misclassified.

As noted above, a wide variety of statistical analysis techniques may be used to determine the one or more statistical relationships. These may include one or more supervised learning techniques, one or more unsupervised learning techniques, one or more parametric analysis techniques (such as a Pearson's product-moment correlation coefficient r or an inner product), and/or one or more non-parametric analysis techniques. Non-parametric analysis techniques may include a Wilcoxon matched pairs signed-rank test (for ordinal or ranked data), a Kolmogorov-Smirnov one-sample test (for ordinal or ranked data), a dependent t-test (for interval or ratio data), a Pearson chi-square, a chi-square test with a continuity correction (such as Yate's chi-square), a Mantel Heanszel chi-square test, a linear-by-linear association test, a maximum likelihood test, a risk ratio, an odds ratio, a log odds ratio, a Yule Q, a Yule Y, a phi-square, a Kappa measure of agreement, a McNemar change test, a Mann Whitney U-test, a Spearman's rank order correlation coefficient, a Kendall's rank correlation, a Krushcal-Wallis One-Way Analysis of Variance, and a Turkey's quick test.

Supervised learning techniques may include least-squares regression (including correlation), ridge regression, partial least-squares (also referred to as partial correlation), a perceptron algorithm, a Winnow algorithm, linear discriminant analysis (LDA), Fisher discriminant analysis (FDA), logistic regression (LR), a Parzen windows classifier, a (k−) nearest-neighbor classification, multivariate adaptive regression splines (MARS), multiple additive regression trees (MART), SVM, LASSO (a regularized linear regression technique like ridge regression, but with $L_1$-norm regularization of the coefficients), least angle regression (LARS), decision trees (such as CART, with and without gradient boosting, such as ID3 and C4.5), bagging, boosting (such as, adaboost) of simple classifiers, kernel density classification, a minimax probability machine (MPM), multi-class classification, multi-label classification, a Gaussian Process classification and regression, Bayesian statistical analysis, a Naive Bayes classifier, and neural networks for regression and classification. While some of these supervised learning algorithms are linear, it should be understood that one or more additional non-linear versions may be derived using the same "kernel-methodology", as previously described for the SVM, leading to a spectrum of kernel-based learning methods, for example, kernel FDA, kernelized logistic regression, the kernelized perceptron algorithm, etc. One or more of these non-linear versions may be used to perform the statistical analysis.

Unsupervised learning techniques may include a kernel density estimation (using, for example, Parzen windows or k-nearest neighbors), more general density estimation techniques, quantile estimation, clustering, spectral clustering, k-means clustering, Gaussian mixture models, an algorithm using hierarchical clustering, dimensionality reduction, such as principal component analysis or PCA, multi-dimensional scaling (MDS), isomap, local linear embedding (LLE), self-organizing maps (SOM), novelty detection (also referred to as single-class classification, such as single-class SVM or single-class MPM), canonical correlation analysis (CCA), independent component analysis (ICA), factor analysis, and/or non-parametric Bayesian techniques like Dirichlet processes. As noted above for the supervised learning techniques, one or more additional non-linear versions of one or more linear unsupervised learning techniques may be used to perform the statistical analysis, such as kernel PCA, kernel CCA and/or kernel ICA.

In some embodiments, at least a portion of the statistical analysis, such as determination of one or more statistical relationships and/or identification of one or more association variables may include spectral analysis. For example, a Fourier transform or a discrete Fourier transform may be performed on the temporal onsets, one or more patterns of occurrence of one or more variables, and/or one or more patterns of occurrence of one or more compound variables. Analysis in the frequency domain may allow patterns in at least some of the data, such an impact of a woman's menstrual cycle, to be determined.

In some embodiments, determination of one or more statistical relationships and/or identification of one or more association variables may include the use of design of experiments. For example, at least the first individual may be exposed to a set of variables and/or compound variables in accordance with a temporal sequence that corresponds to an orthogonal array.

In some embodiments, at least a portion of the statistical analysis and/or identification of one or more association variables may be implemented using one or more filters, including analog filters, digital filters, adaptive filters (using, for example, a least square error or gradient approach, such as steepest decent), and/or neural networks. The one or more filters may be implemented using one or more DSPs. In some embodiments, the statistical analysis and/or identification of one or more association variables may be implemented in hardware, for example, using one or more ASICs, and/or software.

Figure 14:
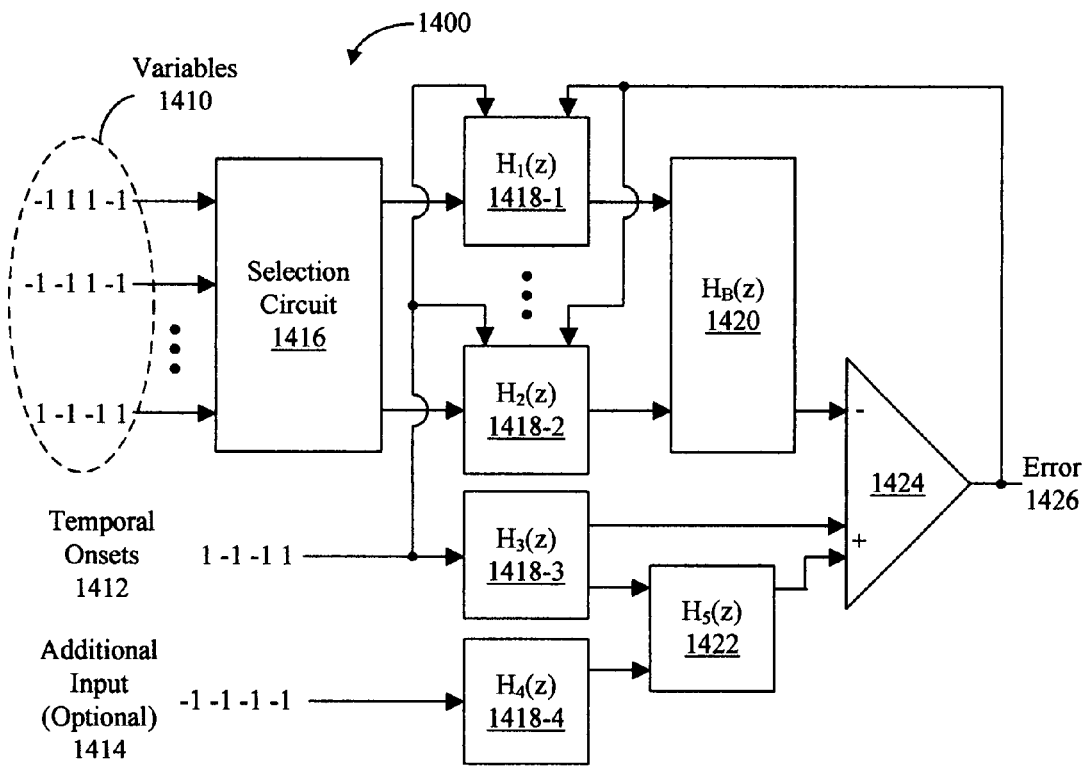
FIG. 14 is a block diagram illustrating an embodiment of a signal processing circuit.

FIG. 14 is a block diagram illustrating an embodiment of a signal processing circuit 1400 for determining one or more statistical relationships and/or identifying one or more association variables. Presence (coded with 1s) and absence information (coded with −1s) for one or more variables 1410 are selectively coupled using selection circuit 1416 to one or more filters $H_i$ 1418. The selection circuit 1416 may be a multiplexer. The filters $H_i$ 1418 may perform spectral modification, such as limiting one or more of the variables 1410 to one or more time intervals, or one or more sequences of time intervals. The filters $H_i$ 1418 may convert the presence and absence information for one or more of the variables 1410 into one or more patterns of occurrence.

The filters $H_i$ 1418 may be adaptive. The adaptation may be in accordance with temporal onsets 1412 and/or an error 1426. The adaptation may include one or more time intervals, such as the first time intervals 912 (FIG. 9A), and/or one or more offsets, such as the offset 924 (FIG. 9A). In some embodiments, the adaptation may minimize or reduce the error 1426 or a portion of the error 1426. In the embodiments for migraine, for example, the adaptation may reduce a predicted number of migraines, a predicted severity, a predicted duration, and/or a predicted frequency.

Outputs from one or more of the filters $H_i$ 1418 may be coupled to filter $H_B$ 1420. The filter $H_B$ 1420 may perform additional spectral modification. As a consequence, an arbitrary filtering operation may be implemented using one or more of the filters $H_i$ 1418 and/or the filter $H_B$ 1420. The filter $H_B$ 1420 may determine a pattern of occurrence for one or more variables 1410 and/or one or more compound variables.

The temporal onsets 1412 may be filtered using filter $H_3$ 1418-3. Comparisons between an output of filter $H_3$ 1418-3 and an output of the filter $H_B$ 1420 may be performed using statistical analysis element 1424. In some embodiments, the statistical analysis element 1424 may be a comparator. Statistical analysis element may implement one or more statistical analysis techniques, such as the log likelihood ratio. The statistical analysis element 1424 may generate the error 1426. The error 1426 may be a scalar, a vector, or a matrix. In some embodiments, the statistical analysis element 1424 may perform a relative time shifting of the output of filter $H_3$ 1418-3 and the output of the filter $H_B$ 1420. In an exemplary embodiment, the statistical analysis element 1424 may determine one or more statistical relationships between the temporal onsets 1412 and one or more patterns of occurrence of one or more variables and/or one or more compound variables. The one or more statistical relationships may be determined sequentially and/or substantially concurrently. The error 1426 may correspond to the one or more statistical relationships.

In some embodiments, one or more optional additional inputs, such as optional additional input 1414, may be filtered using one or more filters, such as filter $H_4$ 1418-4, and/or combined with the temporal onsets 1412 using a filter, such as filter/combiner $H_5$ 1422. An output from the filter/combiner $H_5$ 1422 may be included in the analysis performed by the statistical analysis element 1424. The one or more optional additional inputs may allow inclusion of cross-terms. In some embodiments, the one or more optional additional inputs may include other disease symptoms and/or disease conditions.

While a single output is shown for the filter $H_B$ 1420, there may be additional outputs that are used by the statistical analysis element 1424. Similarly, there may be additional outputs from the filter/combiner $H_5$ 1422 that are used by the statistical analysis element 1424. While embodiment 1400 uses presence and absence information in the one or more variables 1410, the temporal onsets 1412, and the optional additional input 1414, in some embodiments one or more of these items may only use presence information. Embodiment 1400 may include fewer elements or additional elements, a position of at least an element may be changed, and/or functions of two or more elements may be combined into a single element.

Figure 15:
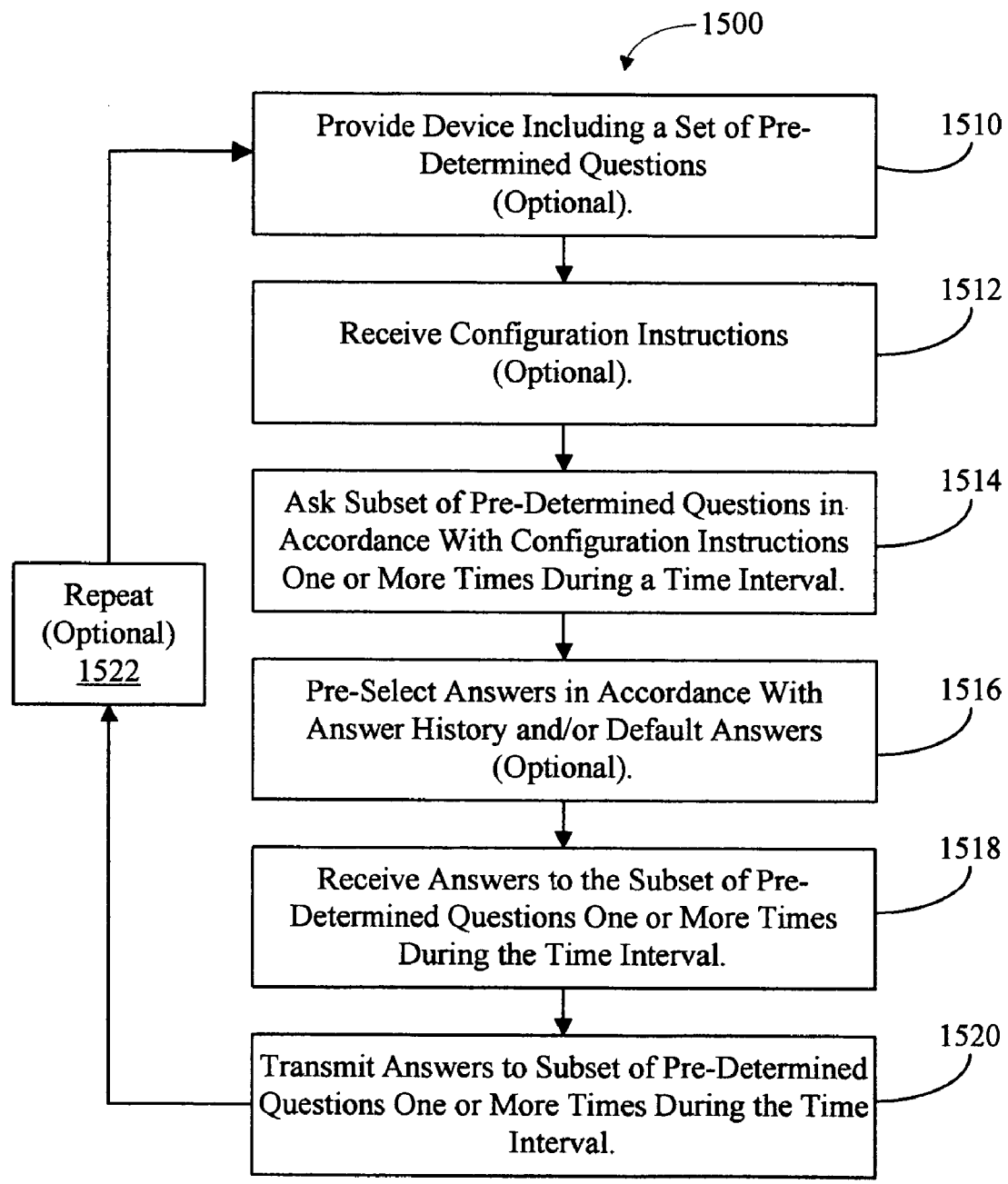
FIG. 15 is a flow diagram illustrating an embodiment of a process for collecting information.

Attention is now directed to embodiments of processes for implementing the collection of information during the data-collection time interval, the determining of one or more statistical relationships, the identification of one or more association variables, and/or the providing of recommendations to at least the first individual and/or at least the second individual. FIG. 15 is a flow diagram illustrating an embodiment 1500 of a process for collecting information. A device including a set of predetermined questions may be optionally provided (1510). Configuration instructions may be optionally received (1512). A subset of pre-determined questions may be asked, one or more times during a time interval, in accordance with the configuration instructions (1514). Answers may be optionally pre-selected in accordance with an answer history and/or default answers (1516). Answers to the subset of pre-determined questions may be received one or more times during the time interval (1518). Answers to the subset of pre-determined questions may be transmitted one or more times during the time interval (1520). Operations in embodiment 1500 may be optionally repeated, one or more times (1522). The process in embodiment 1500 may include fewer operations or additional operations. A position of at least one operation may be changed. Two or more operations may be combined into a single operation.

Figure 16:
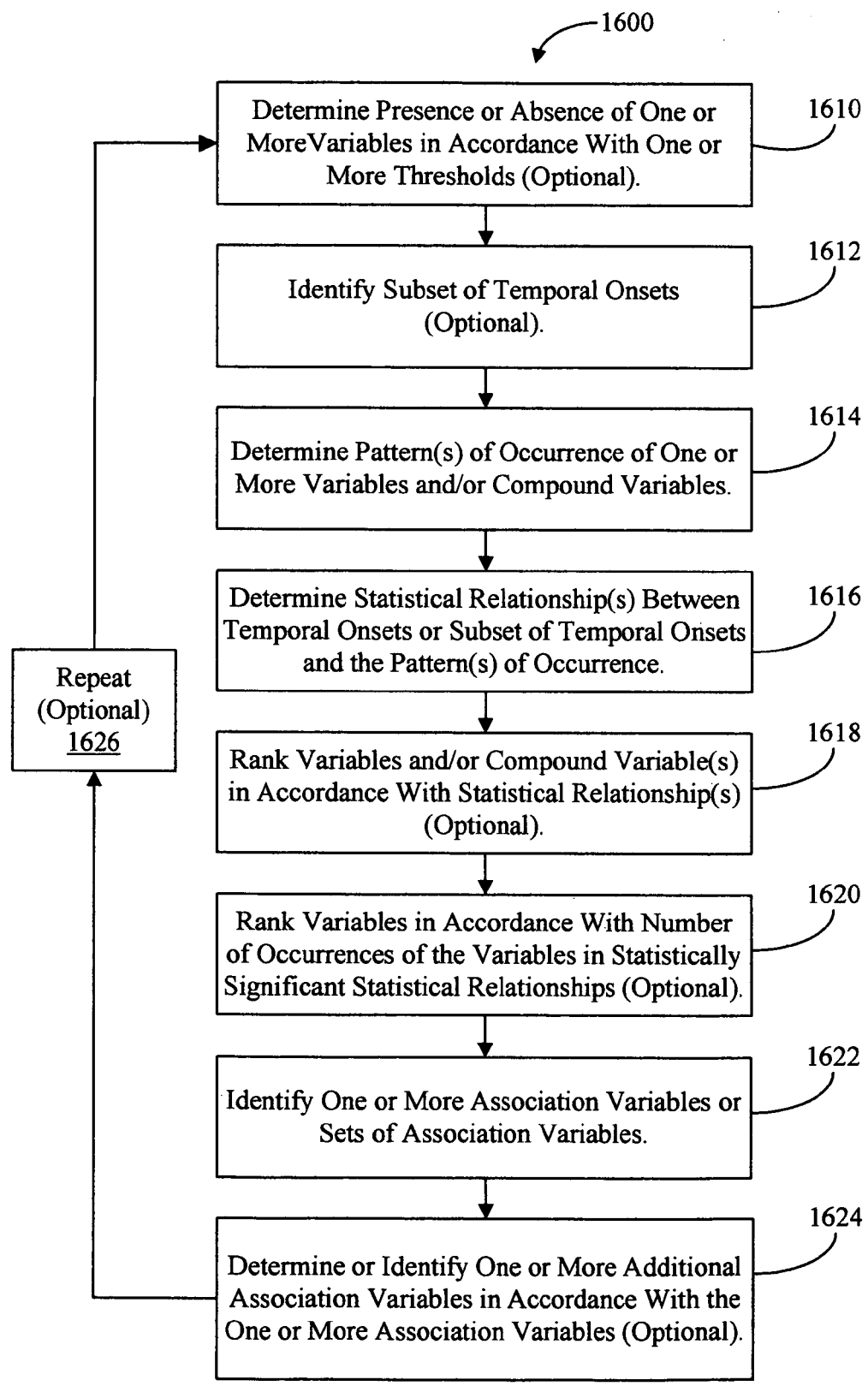
FIG. 16 is a flow diagram illustrating an embodiment of a process for determining one or more association variables.

FIG. 16 is a flow diagram illustrating an embodiment 1600 of a process for determining one or more association variables. Presence or absence of one or more variables may be optionally determined in accordance with one or more thresholds (1610). A subset of temporal onsets may be optionally identified (1612). Pattern(s) of occurrence of one or more variables and/or one or more compound variables may be determined (1614). Statistical relationship(s) between temporal onsets or the subset of temporal onsets and the pattern(s) of occurrence may be determined (1616). The variable(s) and/or the compound variable(s) may be optionally ranked in accordance with the statistical relationship(s) (1618). The variables may be optionally ranked in accordance with a number of occurrences of the variables in statistically significant statistical relationships (1620). One or more association variables and/or sets of association variables may be identified (1622). One or more additional association variables may be optionally determined or identified in accordance with the one or more association variables (1624). Operations in embodiment 1600 may be optionally repeated one or more times (1626). The process in embodiment 1600 may include fewer operations or additional operations, a position of at least one operation may be changed, and/or two or more operations may be combined into a single operation.

Figure 17:
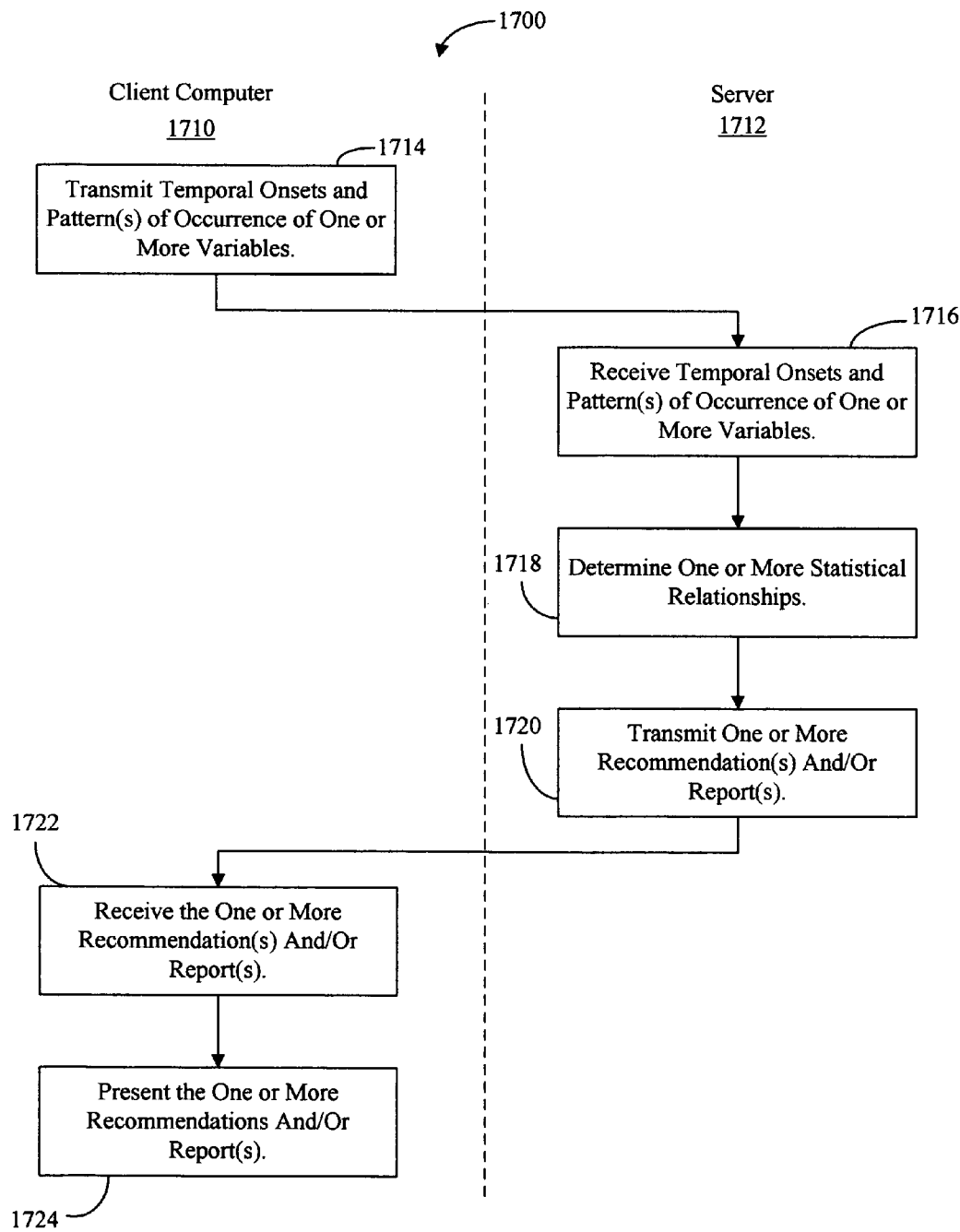
FIG. 17 is a flow diagram illustrating an embodiment of a process for providing recommendation(s) and/or report(s).

FIG. 17 is a flow diagram illustrating an embodiment 1700 of a process for providing recommendation(s) and/or report(s). Temporal onsets and pattern(s) of occurrence of one or more variables may be transmitted (1714) from a client computer 1710 to a server computer 1712. The temporal onsets and the pattern(s) of occurrence of one or more variables may be received (1716). One or more statistical relationships may be determined (1718). One or more recommendation(s) and/or report(s) may be transmitted (1720) from the server 1712 to the client computer 1710. The one or more recommendation(s) and/or report(s) may be received (1722). The one or more recommendations and/or report(s) may be presented (1724).

In some embodiments, the one or more recommendations and/or report(s) may include information corresponding to a first variable during a first set of time intervals and the second variable during a second set of time intervals. A respective time interval in a respective set of time intervals may precede each of the temporal onsets in the one or more temporal onsets. The first variable and the second variable may be associated with a medical condition, i.e., they may be association variables. For example, the first variable and the second variable may be migraine triggers, and at least the first individual may be advised to avoid exposure to at least one of these variables during a given time interval (such as one, two or three days). A data structure that includes respective variables associated with a medical condition is discussed further below with reference to FIG. 25.

The process in embodiment 1700 may include fewer operations or additional operations, a position of at least one operation may be changed, and/or two or more operations may be combined into a single operation.

Figure 18:
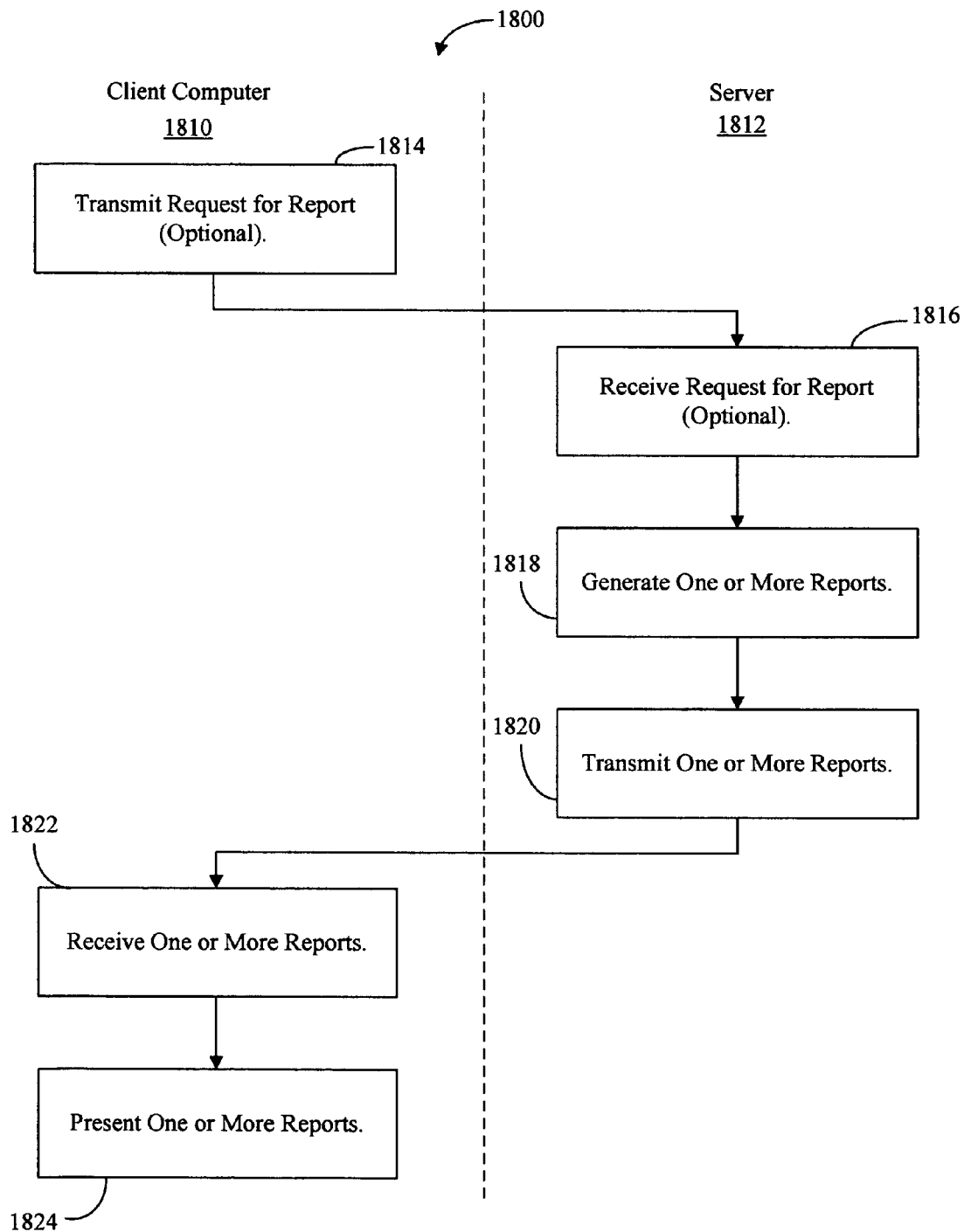
FIG. 18 is a flow diagram illustrating an embodiment of a process for providing one or more reports.

FIG. 18 is a flow diagram illustrating an embodiment 1800 of a process for providing one or more reports. A request for a report may be optionally transmitted (1814) from a client computer 1810 to a server computer 1812. The request for the report may be optionally received (1816). One or more reports may be generated (1818). The one or more reports may be transmitted (1820) from the server 1812 to the client computer 1810. The one or more reports may be received (1822). The one or more reports may be presented (1824). The process in embodiment 1800 may include fewer operations or additional operations, a position of at least one operation may be changed, and/or two or more operations may be combined into a single operation.

Figure 19:
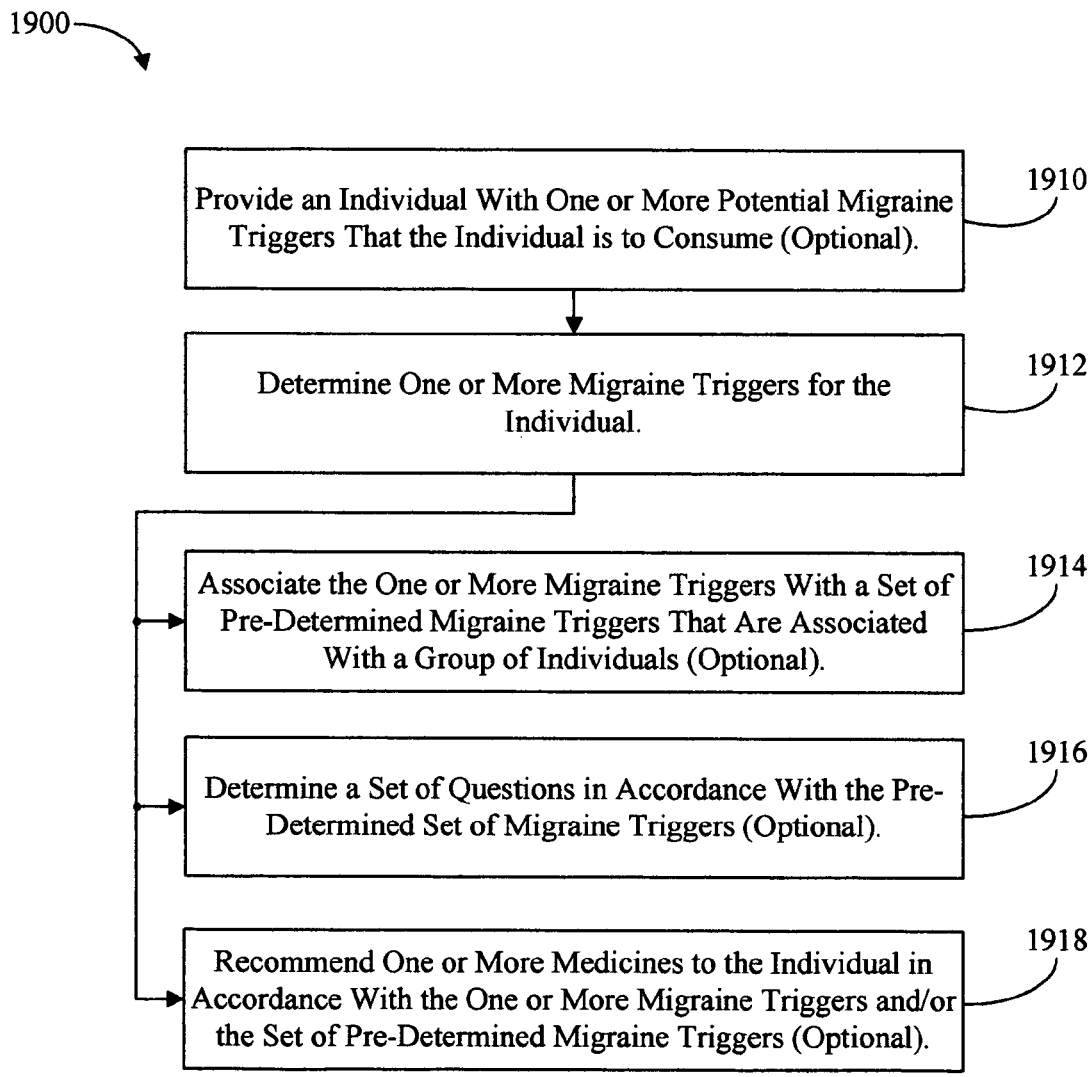
FIG. 19 is a flow diagram illustrating an embodiment of a process.

FIG. 19 is a flow diagram illustrating an embodiment 1900 of a process. An individual, such as at least the first individual, may be optionally provided with one or more potential migraine triggers that the individual is to consume (1910). One or more migraine triggers may be determined for the individual (1912). This determining may include the analysis techniques described previously and/or analysis of an occurrence (including a presence and/or an absence) of one or more markers (such as deoxyribonucleic acid and/or ribonucleic acid) in one or more biological samples taken from the individual (as described further below). For example, the one or more markers may correspond to a migraine trigger associated with one or more receptors for estrogen or one or more receptors for a protein associated with egg white.

As previously discussed with reference to FIG. 13, the one or more migraine triggers may be optionally associated with a set of pre-determined migraine triggers that are associated with a group of individuals (1914). A set of questions may be optionally determined in accordance with the pre-determined set of migraine triggers (1916). The configuration instructions may correspond to the set of questions. Furthermore, one or more medicines may be optionally recommended to the individual in accordance with the one or more migraine triggers and/or the set of pre-determined migraine triggers (1918). For example, an antihistamine (such as periactin or its generic equivalent) may be prescribed for at least the first individual if an allergy or a food sensitivity is determined to be a migraine trigger for at least the first individual. The process in embodiment 1900 may include fewer operations or additional operations. Furthermore, a position of at least one operation may be changed, and/or two or more operations may be combined into a single operation.

As discussed previously, in some embodiments one or more foods consumed (such as mayonnaise) may be mapped to basic constituents (egg, vinegar, and/or mustard) and/or elemental constituents (minerals, fats, carbohydrates, and proteins). Alternatively, the mapping may be used in reverse (i.e., from one or more constituents to compound foods that contain these constituents) to determine the pattern of occurrence for a variable, such as mayonnaise, that occurs in many foods or dishes. These mappings may use a data structure such as that discussed below with reference to FIG. 24.

Figure 20:
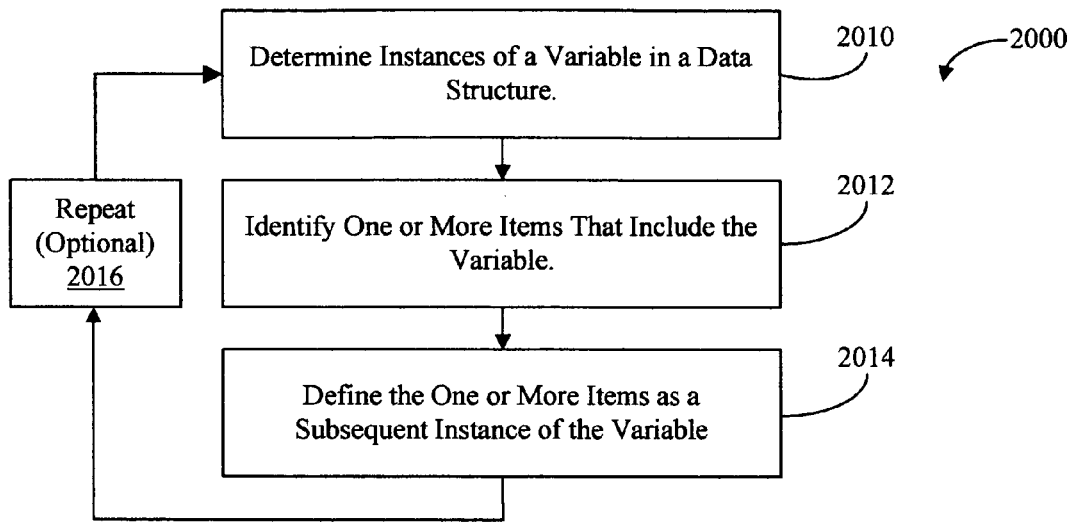
FIG. 20 is a flow diagram illustrating an embodiment of a process for determining items that include a variable.

One or more mapping operations may utilize the technique shown in FIG. 20, which illustrates an embodiment 2000 of a process for determining items that include a variable. Instances of the variable may be determined in a data structure (2010). One or more items that include the variable may be identified (2012). The one or more items may be defined as a subsequent version of the variable (2014). Operations in embodiment 2000 may be optionally repeated one or more times (2016), for example, until a number of iterations are performed, a probability associated with items identified in operation 2012 in a given iteration is less than a pre-determined value, or no instances of items are identified in operation 2012 in the given iteration.

The process in embodiment 2000 may include fewer operations or additional operations, a position of at least one operation may be changed, and/or two or more operations may be combined into a single operation.

Figure 24:
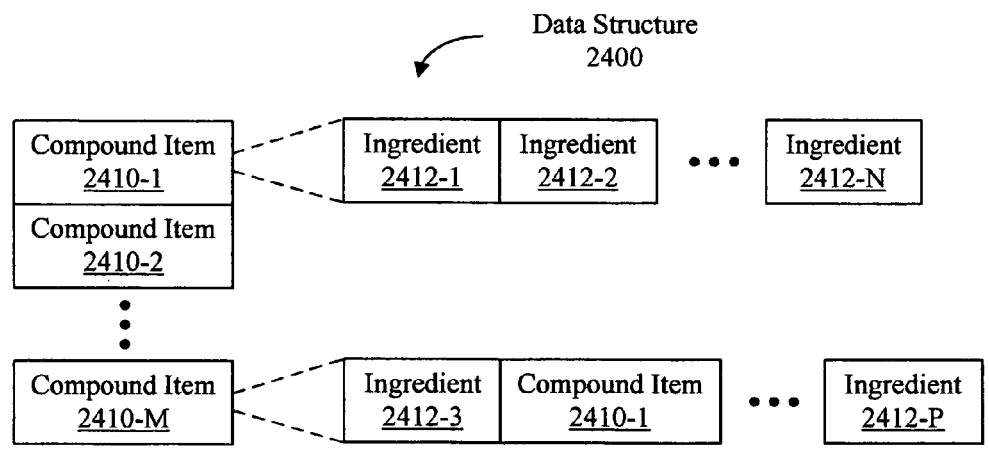
FIG. 24 is a block diagram illustrating an embodiment of a data structure.

The embodiment 2000 of the process may be better understood in the context of FIG. 24, which is a block diagram illustrating an embodiment of a data structure 2400. The data structure 2400 includes a plurality of compound items 2410. A respective compound item, such as compound item 2410-1, may include a plurality of constituent items or ingredients 2412. For example, mayonnaise may include egg, vinegar, and/or mustard. Some compound items, such as compound item 2410-M, may also include one or more compound items, such as the compound item 2410-1, as ingredients. In some embodiments, one or more ingredients 2412 have associated probabilities (not shown) that indicate an uncertainty in the presence of the one or more ingredients 2412 in the compound items 2410. For example, a certain ingredient may occur in a fraction of the recipes for a dish. The data structure 2400 may include fewer or additional elements, a position of one or more elements may be changes, and/or two or more elements may be combined into a single element.

Referring back to FIG. 20, instances of ingredient 2412-1 may be determined (2010). The compound item 2410-1 that includes the ingredient 2412-1 may be identified (2012). The compound item 2410-1 may be defined as a subsequent version of the variable (2014). The operations may be repeated (2016), which will identify the compound item 2410-M as including the compound item 2410-1. The operations may be repeated until one or more of the tree branches in the hierarchy terminate (for example, the operation 2012 does not identify any additional compound items). In some embodiments, a respective branch may terminate if a probability associated with an instance of the variable is less than a pre-determined value. As described previously, one or more ingredients 2412 may have associated probabilities that are less than 1. As the operations are repeated (2016), a product of the probabilities for the ingredients 2412 and/or compound items 2410 in a respective branch may be determined (for example, by multiplying the probabilities of the identified ingredients 2412 and/or compound items 2410 in the respective branch), and if the total probability is less than the pre-determined value (such as 50%), the respective branch may be terminated.

The set of identified compound items (including the compound items 2410-1 and 2410-M) are the foods, dishes or beverages that include the ingredient 2412-1. As discussed previously, this set may be used to determine the pattern of occurrence for the ingredient 2412-1 and/or for a compound variable. In some embodiments, duplicate entries may be excluded from the set of identified compound items. In some embodiments, duplicates may be excluded after each iteration (2016) of the operations in the process.

For some medical conditions, food products (including foods, dishes and/or beverages) may be developed in accordance with the association variables that are determined for one or more groups of individuals. The recommendations provided to at least the first individual may, therefore, include one or more food products in a category of food products that at least the first individual may purchase and/or consume to reduce and/or eliminate one or more symptoms associated with such a medical condition. In some diseases, such as migraines, there may be two or more categories of food products. Food products in a respective category may correspond to one or more groups of individuals that have respective migraine triggers (such as group I 1310 in FIG. 13). As discussed previously with reference to FIG. 13, there may be overlap in the migraine triggers for at least two groups. In some embodiments, therefore, food products in at least two of the categories may be developed in accordance with at least some of the migraine triggers that are common. In some embodiments, however, food products in at least some of the categories may be developed in accordance with unique migraine triggers, i.e., there may not be overlap in the migraine triggers for at least some of the categories.

In some embodiments, the respective food product may exclude at least some of the respective migraine triggers and/or one or more items related to at least one or more of the respective migraine triggers (such as a food in the same food groups as one of the respective migraine triggers). In some embodiments, the respective food product may include amounts or quantities of at least some of the respective migraine triggers and/or amounts or quantities of one or more items related to at least one or more of the respective migraine triggers that are less than corresponding pre-determined values (for example, 1, 2, 5, 10, 25 and/or 50%, by weight, of the respective food product). The respective migraine triggers and/or one or more items related to at least one or more of the respective migraine triggers may include foods, chemicals, and/or ingredients in foods. The respective migraine triggers and/or one or more items related to at least one or more of the respective migraine triggers may include an amino acid, an enzyme and/or a protein. Food products in the two or more categories may include substitutes for the respective migraine triggers and/or one or more items related to at least one or more of the respective migraine triggers. Some of these alternatives are illustrated in Table V. For a respective migraine trigger, none, one, or more than one substitute ingredient may be used.

TABLE V

Migraine triggers and substitute ingredients for use in food products.

| Migraine Triggers | Substitute Ingredients |
|---|---|
| Apple | Pear, Water chestnuts |
| Bacon | Textured soy protein, Mycoprotein |
| Basil | Fennel and Coriander seed |
| Beef; Chicken | Textured soy protein |
| Blueberry | Raspberry |
| Broccoli | Cauliflower |
| Butter | Margarine |
| Carrot | Sweet potato |
| Celery | Celeriac (celery root) |
| Champagne; Red wine | Ver jus (unfermented grape juice) |
| Cheese | Cheese food, Soy cheese |
| Chocolate | Carob |
| Citric acid | Malic acid (apple acid) |
| Clementine | Mandarin |
| Coffee | Chicory |
| Crab | Surimi |
| Cream | Non-dairy creamer |
| Cream cheese; Goat cheese; Yogurt | Tofu (soft) |
| Cucumber | Honeydew |
| Green onion | Chive |
| Jelly | Flavored gelatin, Pectin gel |
| Lettuce | Cabbage, Kale, Spinach, Beet Greens |
| Milk | Soy milk (non-dairy) |
| Monosodium glutamate | Ribotide ™, salt |
| Mustard | Powdered reconstituted mustard |
| Oregano | Epazote |
| Peas | Legumes (kidney, cannellini, garbanzo, etc.) |
| Rice milk | Soy milk (non-dairy) |
| Salad dressing | Soy-based non-acidified sauce |
| Strawberry | Watermelon |
| Sweet potato | Yucca, Plantain |

In some embodiments, the respective food product may include an amount of one or more additional items or compounds that is greater than a pre-determined value. The one or more additional items or compounds may reduce an efficacy of the one or more migraine triggers to induce a migraine in at least the first individual. The one or more additional items or compounds may include an amino acid, an enzyme and/or a protein. In an exemplary embodiment, the respective migraine triggers include tannins. The one or more additional items or compounds may, therefore, include praline. Praline may chemically interact with tannins to produce compounds that are less effective as migraine triggers and/or that are not migraine triggers. The amount or quantity or praline may be selected such that there is sufficient praline to neutralize tannins in the respective food product.

Figure 21:
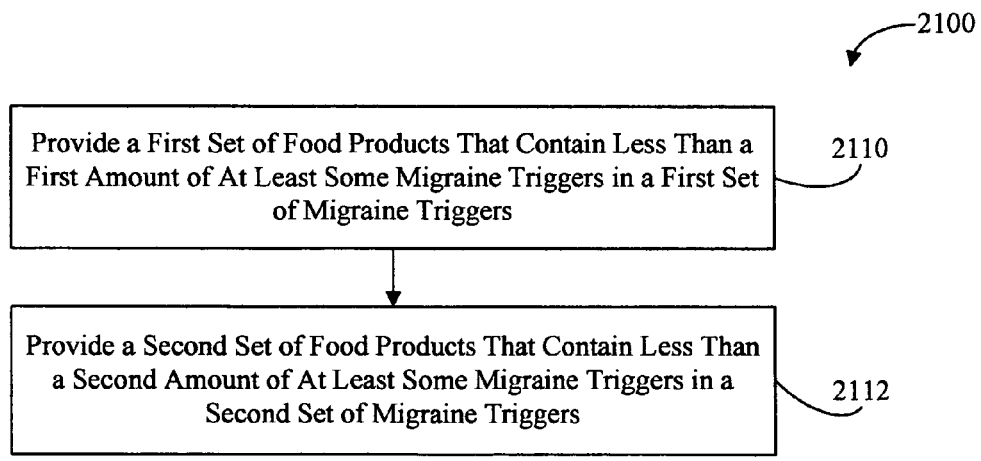
FIG. 21 is a flow diagram illustrating an embodiment of a process for providing food products.

FIG. 21 is a flow diagram illustrating an embodiment 2100 of a process for providing food products. A first set or category of food products that contain less than a first amount of at least some migraine triggers in a first set of migraine triggers are provided (2110). The first set or category of food products may be intended for consumption by members of a first group of individuals that respond to the first set of migraine triggers. For example, one or more migraine triggers in the first set of migraine triggers may, at least in part, induce a migraine in one or more members of the first group of individuals. A second set or category of food products that contain less than a second amount of at least some migraine triggers in a second set of migraine triggers are provided (2112). The second set or category of food products may be intended for consumption by members of a second group of individuals that respond to the second set of migraine triggers. The process in embodiment 2100 may include fewer operations or additional operations, a position of at least one operation may be changed, and/or two or more operations may be combined into a single operation.

Attention is now directed towards alternative applications for the embodiments of the process and apparatus for collecting information, determining one or more statistical relationships, identifying one or more association variables, and providing one or more recommendations and/or one or more reports. In some embodiments, one or more fees may be charged for offering the service of collecting the information and/or identifying one or more association variables (such as one or more migraine triggers) for at least the first individual. In some embodiments, the one or more fees may be in accordance with a cost savings associated with a reduced usage of one or more pharmacological agents (such as one or more acute and/or preventive therapies). The one or more fees may be collected from at least the first individual, at least the second individual, and/or one or more insurance providers. In some embodiments, information associated with the one or more identified association variables may be sold to third parties. In some embodiments, advertising may be presented to at least the first individual and/or at least the second individual during the collection of information, the providing of one or more recommendations and/or the providing of one or more reports. Fees may be charged to advertisers for such services.

In some embodiments, at least the first individual may be associated with one or more groups, such as one or more groups of migraine patients, in accordance with one or more identified association variables (such as migraine triggers). A respective group may be analyzed to determine one or more existing or new acute and/or preventive therapies that may provide improved efficacy for the respective group. Using migraine as an exemplary embodiment, improved efficacy may include a reduction in migraine frequency, a reduction in migraine severity, a reduction in migraine duration, a reduction in recurrence, a reduction in one or more adverse reactions or side effects, a reduction in the use of one or more pharmacological agents, and/or an improved efficacy in aborting one or more migraine attacks relative to other acute and/or preventive therapies.

In some embodiments, association with one or more groups and/or analysis of the respective group may include statistical analysis and/or determining a presence or an absence of one or more biological markers in at least the first individual, including genetic material, deoxyribonucleic acid, ribonucleic acid (such as messenger ribonucleic acid), one or more genes, one or more proteins, and/or one or more enzymes that may be common to the respective group and/or two or more groups. The one or more biological markers may correspond to estrogen, one or more enzymes that assist in the digestion of food (for example, Lactase enzyme), one or more proteins, one or more peptides or polypeptides that include up to 4 or 5 amino acids or more, histamine, one or more antigens, and/or a blood-brain barrier carrier-mediated transporter (such as those for glucose and/or amino acids). The one or more biological markers may be determined by testing one or more biological samples, including a blood sample, a urine sample, a stool sample, a saliva sample, a sweat sample, a mucus sample, a skin scrapping, and/or a tear. The one or more biological samples may be analyzed using chemical analysis, genetic analysis (such as genetic sequencing), nuclear quadrapole resonance, nuclear magnetic resonance, and/or electron spin resonance. In some embodiments, one or more patients that have been diagnosed with a respective disease, such as migraine, may be tested for the one or more biological markers to associate the one or more patients with one or more of the groups of patients, and to recommend one or more pharmacological agents (such as one or more acute pharmacological agents, for example, a respective family of triptans, and/or one or more preventive therapies) that may offer improved efficacy relative to other pharmacological agents for the one or more patients. Such a test or tests, based on the one or more biological markers, may reduce or eliminate the current approach of trial and error in searching for one or more pharmacological agents for patients, such as one or more effective acute and/or preventive therapies, which results in delays in patient treatment and additional expense. In some embodiments, such a test may be used in conjunction with or independently of the previously described embodiments of determining association variables.

In some embodiments, the information collected during the data-collection time interval may be analyzed to determine one or more subgroups within a population of patients, such as the group of migraine patients mentioned above. The one or more subgroups may be determined based on the one or more identified association variables (such as migraine triggers), an efficacy of one or more pharmacological agents (such as one or more acute and/or preventive therapies), side effects or adverse reactions to one or more pharmacological agents, and/or patient symptoms (such as migraine severity, migraine duration, and/or migraine frequency). The subgroups may be determined using statistical analysis and/or determining a presence or an absence of the one or more biological markers. In some embodiments, the one or more subgroups may be used to study drug interactions in a real-world setting and patient population. In some embodiments, the one or more subgroups may be indicative of underlying polymorphism in a genetic basis for a respective disease. Information corresponding to the one or more subgroups may be sold to a third party, for example, for use in molecular biology studies of the respective disease, the development of one or more pharmacological agents, and/or a management of costs associated with the disease.

In an exemplary embodiment, genetic polymorphism for migraine may be determined. Migraine is a genetically heterogeneous (polygenetic) disorder. While there is a strong familial aggregation of migraine (it runs in families) and there is increased concordance for the disease in mono-zygote twins over di-zygote twins, suggesting that it has a significant genetic component, in part it may be explained by environmental determinants. Thus, heritability estimates are calculated to be between 40 and 60%. The complex genetics of migraine (heterogeneity) may have hampered gene identification. Grouping migraine patients into one or more subgroups (i.e., classifying the patients) based on identified migraine triggers may aid in the identification of one or more genetic bases of and/or in the determination of genetic information for this disease.

While embodiments of apparatuses and related methods for determining one or more association variables have been described, the apparatuses and related methods may be applied generally to determine statistical relationships between one or more temporal onsets corresponding to one or more events and patterns of occurrence of one or more variables and/or one or more compound variables in a wide variety of statistical learning problems, in medicine, psychology, statistics, engineering, applied mathematics and operations research. In other embodiments, the apparatuses and related methods may be applied generally to determine statistical relationships between an independent variable (a result) and one or more dependent variables that are time independent or stationary over at least a time interval, such as the data collection time interval.

Figure 22:
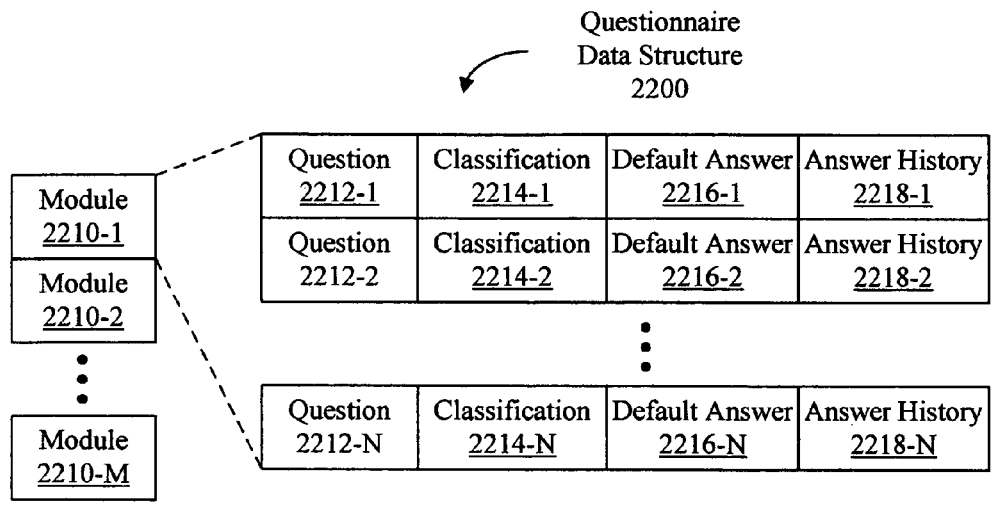
FIG. 22 is a block diagram illustrating an embodiment of a questionnaire data structure.

Attention is now directed to embodiments of data structures that may be used in implementing the collection of information during the data-collection time interval, the determining of one or more statistical relationships, the identification of one or more association variables, and/or the providing of one or more recommendations and/or one or more reports to at least the first individual and/or at least the second individual. FIG. 22 is a block diagram illustrating an embodiment of a questionnaire data structure 2200. The questionnaire data structure 2200 may include one or more modules 2210. A respective module, such as module 2210-1, may include entries for one or more questions 2212, one or more classifications 2214 for the questions 2212 (such as primary or secondary, or general or specific), one or more default answers 2216, and/or one or more answer histories 2218. The questionnaire data structure 2200 may include fewer or addition modules and/or entries. A position of at least a module and/or a position of at least an entry may be changed. Furthermore, two or more modules may be combined into a single module, and/or two or more entries may be combined into a single entry.

Figure 23:
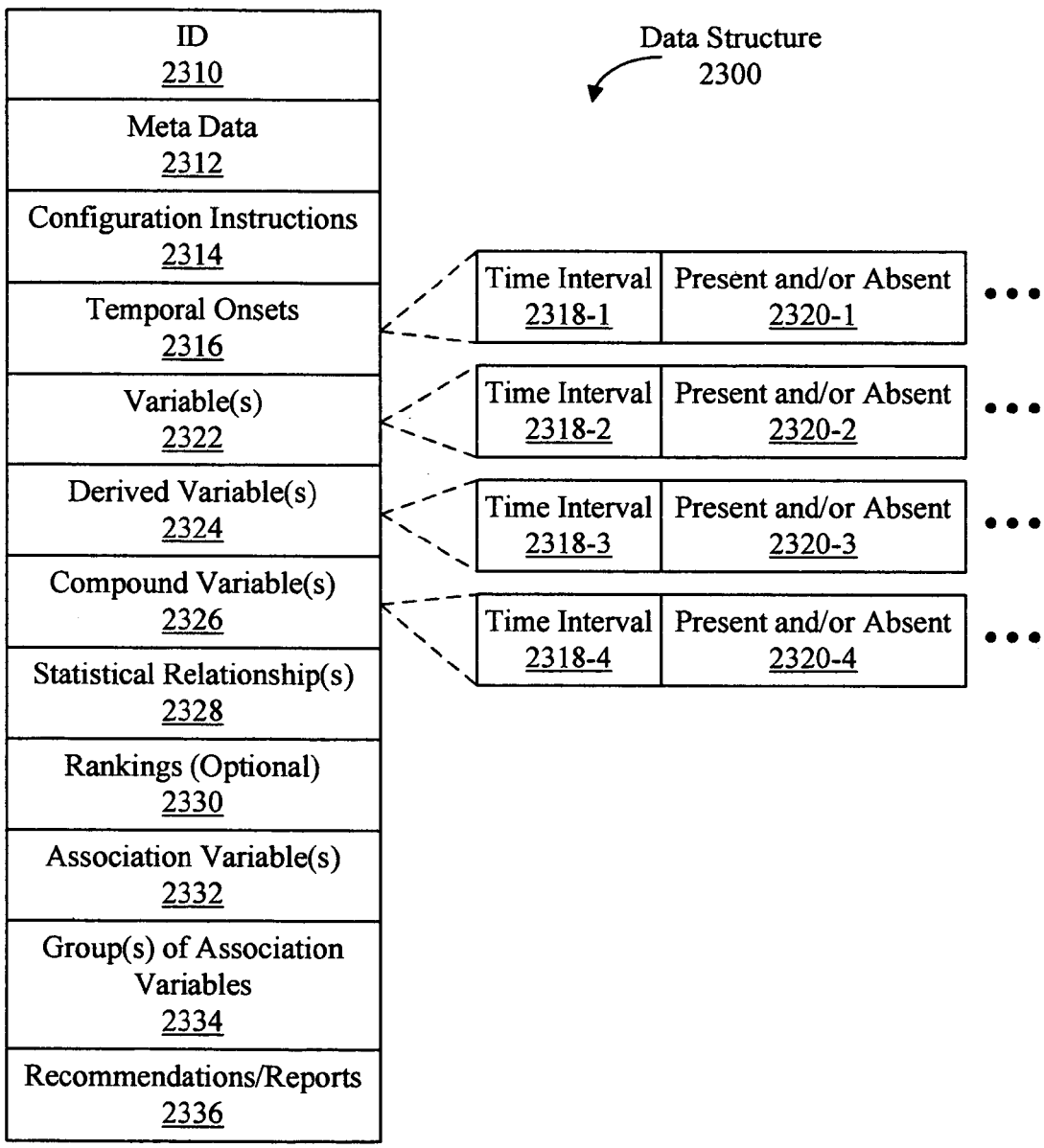
FIG. 23 is a block diagram illustrating an embodiment of a data structure.

FIG. 23 is a block diagram illustrating an embodiment of a data structure 2300. At least a portion of the data structure 2300 may be included in the server computer 300 (FIG. 3), the computer 400 (FIG. 4), and/or the device 500 (FIG. 5). The data structure 2300 may include one or more sets of categories. A respective set of categories may correspond to at least the first individual. The respective set of categories may include identification 2310 for at least the first individual, meta data 2312 (such as relevant demographic, billing and/or medical history data for at least the first individual), configuration instructions 2314, temporal onsets 2316, variable(s) 2322, derived variable(s) 2324, compound variable(s) 2326, statistical relationships 2328, optional rankings 2330, association variable(s) 2332, group(s) of association variables 2334 and/or recommendations/reports 2336. The temporal onsets 2316, the variable(s) 2322, the derived variable(s) 2324, and/or the compound variable(s) 2326 may include one or more entries including time intervals 2318 and corresponding presence and/or absence information 2320. The data structure 2300 may include fewer or addition categories and/or entries, and two or more categories may be combined into a single category. Furthermore, a position of at least a category and/or a position of at least an entry may be changed, and/or two or more entries may be combined into a single entry.

Figure 25:
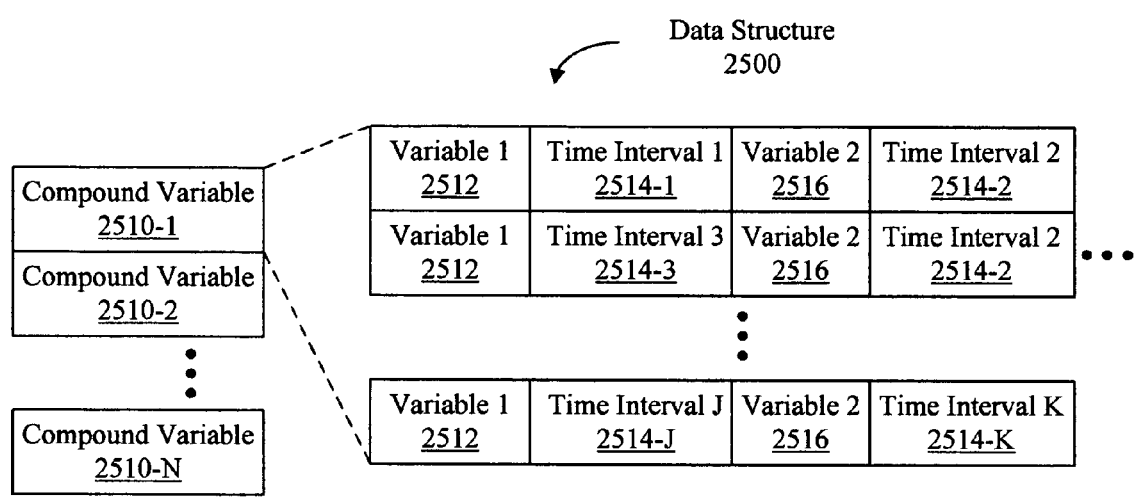
FIG. 25 is a block diagram illustrating an embodiment of a data structure.

FIG. 25 is a block diagram illustrating an embodiment of a data structure 2500. The data structure 2500 may be used in conjunction with the analysis described above with reference to FIGS. 9 and 10, the association with groups described above with reference to FIG. 13, and/or the providing of recommendations and/or reports described above with reference to FIGS. 17 and 18. The data structure may include a plurality of compound variables 2510. A respective compound variable, such as compound variable 2510-1, may include two or more variables, such as variables 2512 and 2516, and corresponding time intervals 2514. The compound variables 2510 may include association variables for one or more medical conditions. While the data structure 2500 includes two variables for each compound vector, in other embodiments respective compound variables may include one, two or more variables.

In an exemplary embodiment, the compound variables 2510 include association variables for migraines, such as migraine triggers, for one or more individuals including at least the first individual. In an illustrative embodiment, the variable 2512 is tomato, time interval 2514-1 is 48-72 hours prior to a migraine onset, the variable 2514 is salad dressing, and the time interval 2514-2 is 0-72 hours prior to the migraine onset. Thus, a migraine may, at least in part, be induced if at least the first individual consumes a quantity of tomato (such as a normal or usual amount consumed by at least the first individual) 48-72 hours earlier and if at least the first individual consumes a quantity of salad dressing (such as a normal or usual amount consumed by at least the first individual) 0-72 hours earlier. In another illustrative embodiment, the variable 2512 is a barometric pressure change of ±8 mm Hg in a 6 hour time interval, time interval 2514-1 is 48-72 hours prior to a migraine onset, the variable 2514 is an orange, and the time interval 2514-2 is 24-72 hours prior to the migraine onset. Thus, a migraine may, at least in part, be induced if at least the first individual is exposed to a barometric pressure change of ±8 mm Hg in a 6 hour time interval 48-72 hours earlier and if at least the first individual consumes a quantity of an orange (such as a normal or usual amount consumed by at least the first individual) 24-72 hours earlier.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purposes of illustration and description. They are not intended to be exhaustive or to limit the invention to the precise forms disclosed. Obviously many modifications and variations are possible in view of the above teachings. The embodiments were chosen and described in order to best explain the principles of the invention and its practical applications, the thereby enable others skilled in the art to best utilize the invention and various embodiments with various modifications as are suited to the particular use contemplated. It is intended that the scope of the invention be defined by the following claims and their equivalents.

What is claimed:

1. An apparatus to determine one or more migraine triggers associated with migraines, comprising:

at least one processor;

at least one memory configured to store information associated with a set of temporal onsets that is associated with headaches experienced by at least one individual, and information associated with a pattern of occurrence of a variable associated with at least the one individual; and at least one program module, the program module stored in the memory and configurable to be executed by the processor, the program module including:

instructions for selecting a subset of temporal onsets in the set of temporal onsets based on one or more characteristics of different types of headaches, wherein the different types of headaches include migraine and recurrence migraine, wherein the subset of temporal onsets includes one or more onsets corresponding to one or more migraines in the headaches experienced by at least the one individual, wherein the set of temporal onsets includes the subset of temporal onsets and one or more temporal onsets corresponding to one or more additional headaches in the headaches experienced by at least the one individual, wherein the one or more additional headaches include one or more recurrence migraines, wherein the one or more characteristics of recurrence migraine include that a given recurrence migraine corresponds to a given temporal onset in a given group of two or more temporal onsets in the set of temporal onsets that is within a predetermined time interval after an initial temporal onset in the given group of two or more temporal onsets, and wherein the group of two or more temporal onsets can be associated with a single migraine attack;

instructions for determining a statistical relationship between the subset of temporal onsets and the pattern of occurrence of the variable in an underdetermined problem in which there are more variables than temporal onsets in the set of temporal onsets, wherein a severity of the underdetermined problem is increased by excluding the one or more temporal onsets corresponding to one or more additional headaches; and instructions for identifying the variable as a migraine trigger in accordance with the statistical relationship.

2. The apparatus of claim 1, wherein the statistical relationship includes contributions from presence and absence information in the pattern of occurrence of the variable.

3. The apparatus of claim 1, wherein the one or more additional headaches include one or more tension headaches.

4. The apparatus of claim 1, further comprising instructions for excluding at least one of the temporal onsets in the set of temporal onsets from the subset of temporal onsets due to missing data in the pattern of occurrence of the variable that was not reported by at least the one individual.

5. The apparatus of claim 1, wherein the pattern of occurrence of the variable is during a set of time intervals, and wherein a respective time interval in the set of time intervals precedes a corresponding respective temporal onset in the subset of temporal onsets.

6. The apparatus of claim 5, wherein time intervals in the set of time intervals are offset in time from temporal onsets in the subset of temporal onsets.

7. The apparatus of claim 1, the program module further including instructions for receiving information including the set of temporal onsets and the pattern of occurrence of the variable.

8. The apparatus of claim 1, the program module further including instructions for providing recommendations to one or more individuals in accordance with the migraine variable.

9. The apparatus of claim 1, wherein the determining uses a non-parametric statistical analysis technique selected from a group consisting of a chi-square analysis technique, a log-likelihood ratio analysis technique and a Fisher's exact probability analysis technique.

10. The apparatus of claim 1, wherein the determining uses a supervised learning technique selected from a group consisting of a support vector machines (SVM) analysis technique, a Lasso analysis technique and a classification and regression tree (CART) analysis technique.

11. The apparatus of claim 1, wherein the predetermined time interval is less than or equal to 24 hours.

12. The apparatus of claim 1, the program module further including instructions for determining statistical relationships for a plurality of variables in the underdetermined problem.

13. The apparatus of claim 12, the program module further including instructions for determining a first ranking of the plurality of variables based on at least a subset of the statistical relationships, wherein the first ranking is based on the number of occurrences of the variables in the at least the subset of the statistical relationships.

14. The apparatus of claim 13, the program module further including instructions for subtracting a second ranking from the first ranking, wherein the second ranking corresponds to a background signal.

15. The apparatus of claim 1, wherein a respective entry in a pattern of occurrence of the variable is considered present if the respective entry approximately exceeds a threshold.

16. The apparatus of claim 1, wherein the migraine trigger at least in part induces a migraine in at least the one individual if at least the one individual is exposed to the migraine trigger.

17. The apparatus of claim 16, the program module further including instructions for identifying one or more additional migraine triggers of at least the one individual based on the presence of the identified migraine trigger in one or more groups of migraine triggers that were previously determined for one or more other individuals.

18. The apparatus of claim 1, wherein entries in the pattern of occurrence of the variable during time intervals associated with ongoing durations of each of the migraines corresponding to the subset of temporal onsets are excluded when the statistical relationship is determined.

19. A non-transitory computer-program product for use in conjunction with a computer system, the computer-program product comprising a computer-readable storage medium and a computer-program mechanism embedded therein for determining one or more migraine triggers associated with migraines, the computer-program mechanism including:

instructions for selecting a subset of temporal onsets in a set of temporal onsets that is associated with headaches experienced by at least one individual based on one or more characteristics of different types of headaches, wherein the different types of headaches include migraine and recurrence migraine, wherein the subset of temporal onsets includes one or more onsets corresponding to one or more migraines in the headaches experienced by at least the one individual, wherein the set of temporal onsets includes the subset of temporal onsets and one or more temporal onsets corresponding to one or more additional headaches in the headaches experienced by at least the one individual, wherein the one or more additional headaches include one or more recurrence migraines, wherein the one or more characteristics of recurrence migraine include that a given recurrence migraine corresponds to a given temporal onset in a given group of two or more temporal onsets in the set of temporal onsets that is within a predetermined time interval after an initial temporal onset in the given group of two or more temporal onsets, and wherein the group of two or more temporal onsets can be associated with a single migraine attack;

instructions for determining a statistical relationship between the subset of temporal onsets and a pattern of occurrence of a variable associated with at least the one individual in an underdetermined problem in which there are more variables than temporal onsets in the set of temporal onsets, wherein a severity of the underdetermined problem is increased by excluding the one or more temporal onsets corresponding to one or more additional headaches; and instructions for identifying the variable as a migraine trigger in accordance with the statistical relationship.

20. An apparatus to determine one or more migraine triggers associated with migraines, comprising:

means for computing;

means for storing information associated with a set of temporal onsets that is associated with headaches experienced by at least one individual, and information associated with a pattern of occurrence of a variable associated with at least the one individual; and at least one program module mechanism, the program module mechanism stored in at least the means for storing and configurable to be executed by at least a computing means, at least the program module mechanism including:

instructions for selecting a subset of temporal onsets in the set of temporal onsets based on one or more characteristics of different types of headaches, wherein the different types of headaches include migraine and recurrence migraine, wherein the subset of temporal onsets includes one or more onsets corresponding to one or more migraines in the headaches experienced by at least the one individual, wherein the set of temporal onsets includes the subset of temporal onsets and one or more temporal onsets corresponding to one or more additional headaches in the headaches experienced by at least the one individual, wherein the one or more additional headaches include one or more recurrence migraines, wherein the one or more characteristics of recurrence migraine include that a given recurrence migraine corresponds to a given temporal onset in a given group of two or more temporal onsets in the set of temporal onsets that is within a predetermined time interval after an initial temporal onset in the given group of two or more temporal onsets, and wherein the group of two or more temporal onsets can be associated with a single migraine attack;

instructions for determining a statistical relationship between the subset of temporal onsets and the pattern of occurrence of the variable in an underdetermined problem in which there are more variables than temporal onsets in the set of temporal onsets, wherein a severity of the underdetermined problem is increased by excluding the one or more temporal onsets corresponding to one or more additional headaches; and instructions for identifying the variable as a migraine trigger in accordance with the statistical relationship.

* * * * *